US007799518B2

(12) United States Patent
Endege et al.

(10) Patent No.: US 7,799,518 B2
(45) Date of Patent: Sep. 21, 2010

(54) NUCLEIC ACID MOLECULES AND PROTEINS FOR THE IDENTIFICATION, ASSESSMENT, PREVENTION, AND THERAPY OF OVARIAN CANCER

(75) Inventors: Wilson O. Endege, Norwood, MA (US); Donna Ford, Plainville, MA (US); Manjula Gannavarapu, Acton, MA (US); Karen Glatt, Natick, MA (US); Sebastian Hoersch, Arlington, MA (US); Shubhangi Kamatkar, Newton, MA (US); John E. Monahan, Walpole, MA (US); Robert Schlegel, Auburndale, MA (US); Yong Yao Xu, Belmont, MA (US); Xumei Zhao, Wayland, MA (US)

(73) Assignees: Millennium Pharmaceuticals, Inc., Cambridge, MA (US); Board of Regents, University of Texas System, Austin, TX (US)

( * ) Notice: Subject to any disclaimer, the term of this patent is extended or adjusted under 35 U.S.C. 154(b) by 749 days.

(21) Appl. No.: 10/961,139

(22) Filed: Oct. 7, 2004

(65) Prior Publication Data
US 2005/0153313 A1 Jul. 14, 2005

Related U.S. Application Data

(60) Provisional application No. 60/509,171, filed on Oct. 7, 2003.

(51) Int. Cl.
*C12Q 1/00* (2006.01)
*C12Q 1/68* (2006.01)
*G01N 33/53* (2006.01)
*G01N 33/574* (2006.01)
(52) U.S. Cl. .............................. 435/4; 435/6; 435/7.1; 435/7.23
(58) Field of Classification Search ............... None
See application file for complete search history.

(56) References Cited

U.S. PATENT DOCUMENTS

| 6,335,170 | B1 | 1/2002 | Orntoft et al. |
| 6,936,417 | B2 | 8/2005 | Orntoft et al. |
| 2004/0219579 | A1 | 11/2004 | Aziz et al. |
| 2006/0019256 | A1* | 1/2006 | Clarke et al. ................ 435/6 |
| 2007/0008334 | A1 | 1/2007 | Takeuchi |

FOREIGN PATENT DOCUMENTS

| WO | WO-00/52151 A2 | 9/2000 |
| WO | WO-01/12662 A2 | 2/2001 |
| WO | WO01/12674 * | 2/2001 |
| WO | WO-01/34767 A2 | 5/2001 |
| WO | WO-02/071928 A2 | 9/2002 |
| WO | WO-03/042661 A2 | 5/2003 |

OTHER PUBLICATIONS

Wang et al., Am. J. Hum. Genet. vol. 71, p. 66-73, 2002.*
Donninger et al., Oncogene, vol. 23, p. 81065-8077, 2004.*
Li et al., PNAS, vol. 104, p. 18636-18641, 2007.*
Sequence search result.*
Mesh word search.*
Kuery et al., Nat Genet, 31, 239-240. 2002.*
Kury et al, Human Mutation, mutation in brief, #649, vol. 22, p. 337-8, published online, Aug. 2003.*
Equence comparision, viriant 1 and 2.*
GenBank Accession No. NP_060237, Mao, X. et al., "A histidine-rich cluster mediates the ubiquitination and degradation of the human zinc transporter, hZIP4, and protects against zinc cytotoxicity," *J. Biol. Chem.*, vol. 282(10):6992-7000 (2007).
Bast, R.C., Jr., et al., "Early detection of ovarian cancer: promise and reality," *Cancer Treat. Res.*, vol. 107:61-97 (2002).
Hellström, Ingegerd et al, "The HE4 (WFDC2) Protein is a Biomarker for Ovarian Carcinoma," *Cancer Research*, vol. 63:3695-3700 (2003).
Yousef, George M. et al, "Parallel Overexpression of Seven Kallikrein Genes in Ovarian Cancer," *Cancer Research*, vol. 63:2223-2227 (2003).
European Search Report for Application No. 04794501.9-1223, dated Jan. 10, 2008.

* cited by examiner

*Primary Examiner*—Larry R. Helms
*Assistant Examiner*—Lei Yao
(74) *Attorney, Agent, or Firm*—McCarter & English, LLP; Maria Laccotripe Zacharakis; Marcie B. Clarke

(57) ABSTRACT

The invention relates to newly discovered nucleic acid molecules and proteins associated with ovarian cancer. Compositions, kits, and methods for detecting, characterizing, preventing, and treating human ovarian cancers are provided.

27 Claims, No Drawings

NUCLEIC ACID MOLECULES AND PROTEINS FOR THE IDENTIFICATION, ASSESSMENT, PREVENTION, AND THERAPY OF OVARIAN CANCER

RELATED APPLICATIONS

This Application claims the benefit of U.S. Provisional Application Ser. No. 60/509,171 filed Oct. 7, 2003, the entire content of which is hereby incorporated by reference.

FIELD OF THE INVENTION

The field of the invention is ovarian cancer, including diagnosis, characterization, management, and therapy of ovarian cancer.

BACKGROUND OF THE INVENTION

Ovarian cancer is responsible for significant morbidity and mortality in populations around the world. Ovarian cancer is classified, on the basis of clinical and pathological features, in three groups, namely epithelial ovarian cancer (EOC; >90% of ovarian cancer in Western countries), germ cell tumors (circa 2-3% of ovarian cancer), and stromal ovarian cancer (circa 5% of ovarian cancer; Ozols et al., 1997, *Cancer Principles and Practice of Oncology*, 5th ed., DeVita et al., Eds. pp. 1502). Relative to EOC, germ cell tumors and stromal ovarian cancers are more easily detected and treated at an early stage, translating into higher/better survival rates for patients afflicted with these two types of ovarian cancer.

There are numerous types of ovarian tumors, some of which are benign, and others of which are malignant. Treatment (including non-treatment) options and predictions of patient outcome depend on accurate classification of the ovarian cancer. Ovarian cancers are named according to the type of cells from which the cancer is derived and whether the ovarian cancer is benign or malignant. Recognized histological tumor types include, for example, serous, mucinous, endometrioid, and clear cell tumors. In addition, ovarian cancers are classified according to recognized grade and stage scales.

In grade I, the tumor tissue is well differentiated. In grade II, tumor tissue is moderately well differentiated. In grade III, the tumor tissue is poorly differentiated. This grade correlates with a less favorable prognosis than grades I and II. Stage I is generally confined within the capsule surrounding one (stage IA) or both (stage IB) ovaries, although in some stage I (i.e. stage IC) cancers, malignant cells may be detected in ascites, in peritoneal rinse fluid, or on the surface of the ovaries. Stage II involves extension or metastasis of the tumor from one or both ovaries to other pelvic structures. In stage IIA, the tumor extends or has metastasized to the uterus, the fallopian tubes, or both. Stage IIB involves extension of the tumor to the pelvis. Stage IIC is stage IIA or IIB in which malignant cells may be detected in ascites, in peritoneal rinse fluid, or on the surface of the ovaries. In stage III, the tumor comprises at least one malignant extension to the small bowel or the omentum, has formed extrapelvic peritoneal implants of microscopic (stage IIIA) or macroscopic (<2 centimeter diameter, stage IIIB; >2 centimeter diameter, stage IIIC) size, or has metastasized to a retroperitoneal or inguinal lymph node (an alternate indicator of stage IIIC). In stage IV, distant (i.e. non-peritoneal) metastases of the tumor can be detected.

The durations of the various stages of ovarian cancer are not presently known, but are believed to be at least about a year each (Richart et al., 1969, *Am. J. Obstet. Gynecol.* 105: 386). Prognosis declines with increasing stage designation. For example, 5-year survival rates for patients diagnosed with stage I, II, III, and IV ovarian cancer are 80%, 57%, 25%, and 8%, respectively.

Despite being the third most prevalent gynecological cancer, ovarian cancer is the leading cause of death among those afflicted with gynecological cancers. The disproportionate mortality of ovarian cancer is attributable to a substantial absence of symptoms among those afflicted with early-stage ovarian cancer and to difficulty diagnosing ovarian cancer at an early stage. Patients afflicted with ovarian cancer most often present with non-specific complaints, such as abnormal vaginal bleeding, gastrointestinal symptoms, urinary tract symptoms, lower abdominal pain, and generalized abdominal distension. These patients rarely present with paraneoplastic symptoms or with symptoms which clearly indicate their affliction. Presently, less than about 40% of patients afflicted with ovarian cancer present with stage I or stage II. Management of ovarian cancer would be significantly enhanced if the disease could be detected at an earlier stage, when treatments are much more generally efficacious.

Ovarian cancer may be diagnosed, in part, by collecting a routine medical history from a patient and by performing physical examination, x-ray examination, and chemical and hematological studies on the patient. Hematological tests which may be indicative of ovarian cancer in a patient include analyses of serum levels of proteins designated CA125 and DF3 and plasma levels of lysophosphatidic acid (LPA). Palpation of the ovaries and ultrasound techniques (particularly including endovaginal ultrasound and color Doppler flow ultrasound techniques) can aid detection of ovarian tumors and differentiation of ovarian cancer from benign ovarian cysts. However, a definitive diagnosis of ovarian cancer typically requires performing exploratory laparotomy of the patient.

Potential tests for the detection of ovarian cancer (e.g., screening, reflex or monitoring) may be characterized by a number of factors. The "sensitivity" of an assay refers to the probability that the test will yield a positive result in an individual afflicted with ovarian cancer. The "specificity" of an assay refers to the probability that the test will yield a negative result in an individual not afflicted with ovarian cancer. The "positive predictive value" (PPV) of an assay is the ratio of true positive results (i.e. positive assay results for patients afflicted with ovarian cancer) to all positive results (i.e. positive assay results for patients afflicted with ovarian cancer+positive assay results for patients not afflicted with ovarian cancer). It has been estimated that in order for an assay to be an appropriate population-wide screening tool for ovarian cancer the assay must have a PPV of at least about 10% (Rosenthal et al., 1998, *Sem. Oncol.* 25:315-325). It would thus be desirable for a screening assay for detecting ovarian cancer in patients to have a high sensitivity and a high PPV. Monitoring and reflex tests would also require appropriate specifications.

Owing to the cost, limited sensitivity, and limited specificity of known methods of detecting ovarian cancer, screening is not presently performed for the general population. In addition, the need to perform laparotomy in order to diagnose ovarian cancer in patients who screen positive for indications of ovarian cancer limits the desirability of population-wide screening, such that a PPV even greater than 10% would be desirable.

Prior use of serum CA125 level as a diagnostic marker for ovarian cancer indicated that this method exhibited insufficient specificity for use as a general screening method. Use of a refined algorithm for interpreting CA125 levels in serial retrospective samples obtained from patients improved the specificity of the method without shifting detection of ovarian cancer to an earlier stage (Skakes, 1995, *Cancer* 76:2004). Screening for LPA to detect gynecological cancers including ovarian cancer exhibited a sensitivity of about 96% and a specificity of about 89%. However, CA125-based screening methods and LPA-based screening methods are hampered by the presence of CA125 and LPA, respectively, in the serum of patients afflicted with conditions other than ovarian cancer. For example, serum CA125 levels are known to be associated with menstruation, pregnancy, gastrointestinal and hepatic conditions such as colitis and cirrhosis, pericarditis, renal disease, and various non-ovarian malignancies. Serum LPA is known, for example, to be affected by the presence of non-ovarian gynecological malignancies. A screening method having a greater specificity for ovarian cancer than the current screening methods for CA125 and LPA could provide a population-wide screening for early stage ovarian cancer.

Presently greater than about 60% of ovarian cancers diagnosed in patients are stage III or stage IV cancers. Treatment at these stages is largely limited to cytoreductive surgery (when feasible) and chemotherapy, both of which aim to slow the spread and development of metastasized tumor. Substantially all late stage ovarian cancer patients currently undergo combination chemotherapy as primary treatment, usually a combination of a platinum compound and a taxane. Median survival for responding patients is about one year. Combination chemotherapy involving agents such as doxorubicin, cyclophosphamide, cisplatin, hexamethylmelamine, paclitaxel, and methotrexate may improve survival rates in these groups, relative to single-agent therapies. Various recently-developed chemotherapeutic agents and treatment regimens have also demonstrated usefulness for treatment of advanced ovarian cancer. For example, use of the topoisomerase I inhibitor topectan, use of amifostine to minimize chemotherapeutic side effects, and use of intraperitoneal chemotherapy for patients having peritoneally implanted tumors have demonstrated at least limited utility. Presently, however, the 5-year survival rate for patients afflicted with stage III ovarian cancer is 25%, and the survival rate for patients afflicted with stage IV ovarian cancer is 8%.

In summary, the earlier ovarian cancer is detected, the aggressiveness of therapeutic intervention and the side effects associated with therapeutic intervention are minimized. More importantly, the earlier the cancer is detected, the survival rate and quality of life of ovarian cancer patients is enhanced. Thus, a pressing need exists for methods of detecting ovarian cancer as early as possible. There also exists a need for methods of detecting recurrence of ovarian cancer as well as methods for predicting and monitoring the efficacy of treatment. There further exists a need for new therapeutic methods for treating ovarian cancer. The present invention satisfies these needs.

DESCRIPTION OF THE INVENTION

The invention relates to cancer markers (hereinafter "markers" or "markers of the inventions"), which are listed in Table 1. The invention provides nucleic acids and proteins that are encoded by or correspond to the markers (hereinafter "marker nucleic acids" and "marker proteins," respectively). The invention further provides antibodies, antibody derivatives and antibody fragments which bind specifically with such proteins and/or fragments of the proteins.

In one aspect, the invention relates to various diagnostic, monitoring, test and other methods related to ovarian cancer detection and therapy. In one embodiment, the invention provides a diagnostic method of assessing whether a patient has ovarian cancer or has higher than normal risk for developing ovarian cancer, comprising the steps of comparing the level of expression of a marker of the invention in a patient sample and the normal level of expression of the marker in a control, e.g., a sample from a patient without ovarian cancer. A significantly higher level of expression of the marker in the patient sample as compared to the normal level is an indication that the patient is afflicted with ovarian cancer or has higher than normal risk for developing ovarian cancer.

In a preferred embodiment of the diagnostic method, the marker is over-expressed by at least two-fold in at least about 20% of stage I ovarian cancer patients, stage II, ovarian cancer patients, stage III ovarian cancer patients, stage V. ovarian cancer patients, grade I ovarian cancer patients, grade II ovarian cancer patients, grade III ovarian cancer patients, epithelial ovarian cancer patients, stromal ovarian cancer patients, germ cell ovarian cancer patients, malignant ovarian cancer patients, benign ovarian cancer patients, serous neoplasm ovarian cancer patients, mucinous neoplasm ovarian cancer patients, endometrioid neoplasm ovarian cancer patients and/or clear cell neoplasm ovarian cancer patients.

The diagnostic methods of the present invention are particularly useful for patients with an identified pelvic mass or symptoms associated with ovarian cancer. The methods of the present invention can also be of particular use with patients having an enhanced risk of developing ovarian cancer (e.g., patients having a familial history of ovarian cancer, patients identified as having a mutant oncogene, and patients at least about 50 years of age).

In a preferred diagnostic method of assessing whether a patient is afflicted with ovarian cancer (e.g., new detection ("screening"), detection of recurrence, reflex testing), the method comprises comparing the level of expression of a marker of the invention in a patient sample, and the normal level of expression of the marker in a control non-ovarian cancer sample. A significantly higher level of expression of the marker in the patient sample as compared to the normal level is an indication that the patient is afflicted with ovarian cancer.

The invention also provides diagnostic methods for assessing the efficacy of a therapy for inhibiting ovarian cancer in a patient. Such methods comprise comparing expression of a marker of the invention in a first sample obtained from the patient prior to providing at least a portion of the therapy to the patient, and expression of the marker in a second sample obtained from the patient following provision of the portion of the therapy. A significantly lower level of expression of the marker in the second sample relative to that in the first sample is an indication that the therapy is efficacious for inhibiting ovarian cancer in the patient.

It will be appreciated that in these methods the "therapy" may be any therapy for treating ovarian cancer including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the diagnostic methods of the present invention are directed to therapy using a chemical or biologic agent. These methods comprise comparing expression of a marker of the invention in a first sample obtained from the patient and maintained in the presence of the chemical or biologic agent, and expression of the marker in a second sample obtained from the patient and maintained in the absence of the agent. A significantly lower level of expression of the marker in the first sample relative to that in the second sample is an indication that the agent is efficacious for inhibiting ovarian cancer in the patient. In one embodiment, the first and second samples can be portions of a single sample obtained from the patient or portions of pooled samples obtained from the patient.

The invention additionally provides a monitoring method for assessing the progression of ovarian cancer in a patient, the method comprising detecting in a patient sample at a first time point, the expression of a marker of the invention; repeating the detection at a subsequent time point in time; and comparing the level of expression detected, and therefrom monitoring the progression of ovarian cancer in the patient. A significantly higher level of expression of the marker in the sample at the subsequent time point from that of the sample at the first time point is an indication that the ovarian cancer has progressed, whereas a significantly lower level of expression is an indication that the ovarian cancer has regressed.

The invention further provides a diagnostic method for determining whether ovarian cancer has metastasized or is likely to metastasize in the future, the method comprising comparing the level of expression of a marker of the invention in a patient sample, and the normal level (or non-metastatic level) of expression of the marker in a control sample. A significantly higher level of expression in the patient sample as compared to the normal level (or non-metastatic level) is an indication that the ovarian cancer has metastasized or is likely to metastasize in the future.

The invention moreover provides a test method for selecting a composition for inhibiting ovarian cancer in a patient. This method comprises obtaining a sample comprising cancer cells from the patient; separately maintaining aliquots of the sample in the presence of a plurality of test compositions; comparing expression of a marker of the invention in each of the aliquots; and then selecting one of the test compositions which significantly reduces the level of expression of the marker in the aliquot containing that test composition, relative to the levels of expression of the marker in the presence of the other test compositions.

The invention additionally provides a test method of assessing the ovarian carcinogenic potential of a compound. This method comprises maintaining separate aliquots of ovarian cells in the presence and absence of the compound; and comparing expression of a marker of the invention in each of the aliquots. A significantly higher level of expression of the marker in the aliquot maintained in the presence of the compound, relative to that of the aliquot maintained in the absence of the compound, is an indication that the compound possesses ovarian carcinogenic potential.

In addition, the invention further provides a method of inhibiting ovarian cancer in a patient. This method comprises obtaining a sample comprising cancer cells from the patient; separately maintaining aliquots of the sample in the presence of a plurality of compositions; then comparing expression of a marker of the invention in each of the aliquots; and lastly administering to the patient at least one of the compositions which significantly lowers the level of expression of the marker in the aliquot containing that composition, relative to the levels of expression of the marker in the presence of the other compositions.

In the aforementioned methods, the samples or patient samples comprise cells obtained from the patient. The cells may be found in an ovarian tissue sample collected, for example, by an ovarian tissue biopsy or histology section. In one embodiment, the patient sample is an ovary-associated body fluid. Such fluids include, for example, blood fluids, lymph, ascites fluids, gynecological fluids, cystic fluids, urine, and fluids collected by peritoneal rinsing. In another embodiment, the sample comprises cells obtained from the patient. In this embodiment, the cells may be found in a fluid selected from the group consisting of a fluid collected by peritoneal rinsing, a fluid collected by uterine rinsing, a uterine fluid, a uterine exudate, a pleural fluid, and an ovarian exudate. In a further embodiment, the patient sample is in vivo.

According to the invention, the level of expression of a marker of the invention in a sample can be assessed, for example, by detecting the presence in the sample of:

the corresponding marker protein (e.g., a protein having one of the sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID. NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44) or a fragment of the protein (e.g. by using a reagent, such as an antibody, an antibody derivative, an antibody fragment or single-chain antibody, which binds specifically with the protein or protein fragment);

the corresponding marker nucleic acid (e.g., a nucleic acid having one of the sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43 or a fragment of the nucleic acid (e.g. by contacting transcribed polynucleotides obtained from the sample with a substrate having affixed thereto one or more nucleic acids having the entire or a segment of the sequence or a complement thereof); or a metabolite which is produced directly (i.e., catalyzed) or indirectly by the corresponding marker protein.

According to the invention, any of the aforementioned methods may be performed using a plurality (e.g. 2, 3, 5, or 10 or more) of ovarian cancer markers, including ovarian cancer markers known in the art. In such methods, the level of expression in the sample of each of a plurality of markers, at least one of which is a marker of the invention, is compared with the normal or control level of expression of each of the plurality of markers in samples of the same type obtained from control humans not afflicted with ovarian cancer. A significantly altered (i.e., increased or decreased as specified in the above-described methods using a single marker) level of expression in the sample of one or more markers of the invention, or some combination thereof, relative to that marker's corresponding normal levels, is an indication that the patient is afflicted with ovarian cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having the sequence of any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44; or a fragment of the protein. The invention also provides methods for making such antibody, antibody derivative, and antibody fragment. Such methods may comprise immunizing a mammal with a protein or peptide comprising the entirety, or a segment of 10 or more amino acids or more, of a marker protein, wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein (e.g., a protein having the sequence of any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44; or a fragment of the protein.

In another aspect, the invention relates to various diagnostic and test kits. In one embodiment, the invention provides a kit for assessing whether a patient is afflicted with ovarian cancer. The kit comprises a reagent for assessing expression of a marker of the invention. In another embodiment, the invention provides a kit for assessing the suitability of a chemical or biologic agent for inhibiting an ovarian cancer in a patient. Such kit comprises a reagent for assessing expression of a marker of the invention, and may also comprise one or more of such agents. In a further embodiment, the invention provides kits for assessing the presence of ovarian cancer cells or treating ovarian cancers. Such kits comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention also provides a kit for assessing the presence of ovarian cancer cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, the invention relates to methods for treating a patient afflicted with ovarian cancer or at risk of developing ovarian cancer. Such methods may comprise reducing the expression and/or interfering with the biological function of a marker of the invention. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an antisense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having the sequence of any of the markers listed in Table 1, or a fragment of such a protein.

It will be appreciated that the methods and kits of the present invention may also include known cancer markers including known ovarian cancer markers. It will further be appreciated that the methods and kits may be used to identify cancers other than ovarian cancer.

In another aspect the invention features nucleic acid molecules which encode marker proteins or marker polypeptides, e.g., a biologically active portion of the marker protein. In a preferred embodiment, the isolated nucleic acid molecules encode marker polypeptides having the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44. In other embodiments, the invention provides isolated marker nucleic acid molecules having the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID. NO: 43. In still other embodiments, the invention provides nucleic acid molecules that are substantially identical (e.g., naturally occurring allelic variants) to the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43. In other embodiments, the invention provides nucleic acid molecules which hybridize under stringent hybridization condition as described herein to nucleic acid molecules comprising the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43, wherein the nucleic acid encodes a full length marker protein or an active fragment thereof.

In a related aspect, the invention further provides nucleic acid constructs which include marker nucleic acid molecules described herein. In certain embodiments, the nucleic acid molecules of the invention are operatively linked to native or heterologous regulatory sequences. Also included are vectors and host cells containing marker nucleic acid molecules of the invention e.g., vectors and host cells suitable for producing polypeptides.

In another related aspect, the invention provides nucleic acid fragments suitable as primers or hybridization probes for the detection of marker-encoding nucleic acids.

In still another related aspect, isolated nucleic acid molecules that are antisense to a marker encoding nucleic acid molecule are provided.

In other embodiments, the invention provides marker polypeptides, e.g., marker polypeptide having the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44; an amino acid sequence that is substantially identical to the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44; or amino acid sequences encoded by nucleic acid molecules having a nucleotide sequence which hybridizes under a stringent hybridization condition as described herein to nucleic acid molecules comprising the nucleotide sequences of SEQ ID NO:(nts), wherein the nucleic acid encodes a full length marker protein or an active fragment thereof.

In a related aspect, the invention further provides nucleic acid constructs which include marker nucleic acid molecule described herein.

In a related aspect, the invention provides marker polypeptides or fragments operatively linked to non-marker polypeptides to form fusion proteins.

In another aspect, the invention features antibodies and antigen-binding fragments thereof, that react with, or more preferably specifically or selectively bind marker polypeptides.

rian cancer in a patient. Methods are provided for detecting the presence of ovarian cancer in a sample, the absence of ovarian cancer in a sample, the stage of an ovarian cancer, assessing whether a breast cancer has metastasized, predicting the likely clinical outcome of a breast cancer patient and with other characteristics of ovarian cancer that are relevant to prevention, diagnosis, characterization, and therapy of ovarian cancer in a patient. Methods of treating ovarian cancer are also provided.

Table 1 lists all of the markers of the invention, which are over-expressed in ovarian cancer cells compared to normal (i.e., non-cancerous) ovarian cells. In this Table the markers are identified with a name ("Marker"), the name the gene is commonly known by, if applicable ("Gene Name"), the Sequence Listing identifier of the cDNA sequence of a nucleotide transcript encoded by or corresponding to the marker ("SEQ ID NO (nts)"), the Sequence Listing identifier of the amino acid sequence of a protein encoded by the nucleotide transcript ("SEQ ID NO (AAs)"), and the location of the protein coding sequence within the cDNA sequence ("CDS").

TABLE 1

Ovarian Cancer Markers

| Marker | Gene Name | SEQ ID NO (nts) | SEQ ID NO (AAs) | CDS |
|---|---|---|---|---|
| M138 | CTHRC1: collagen triple helix repeat containing 1 | 1 | 2 | 27 . . . 863 |
| M437 | FLJ10546: hypothetical protein FLJ10546 | 3 | 4 | 28 . . . 1815 |
| M445 | FLJ23499: hypothetical protein FLJ23499 | 5 | 6 | 21 . . . 473 |
| M452A | IMP-2: IGF-II mRNA-binding protein 2, variant 1 | 7 | 8 | 65 . . . 1735 |
| M712 | IMP-2: IGF-II mRNA-binding protein 2, variant 2 | 9 | 10 | 65 . . . 1603 |
| OV32A | KLK10: kallikrein 10 | 11 | 12 | 220 . . . 1050 |
| OV33A | KLK6: kallikrein 6 (neurosin, zyme) | 13 | 14 | 246 . . . 980 |
| M472 | MAL2: T-cell differentiation protein 2 | 15 | 16 | 88 . . . 618 |
| M590 | FLJ90687: hypothetical protein FLJ90687 | 17 | 18 | 21 . . . .404 |
| OV52A | MMP7: matrix metalloproteinase 7 (matrilysin, uterine) | 19 | 20 | 48 . . . 851 |
| OV51A | PTGS1: prostaglandin-endoperoxide synthase 1 (prostaglandin G/H synthase and cyclooxygenase), transcript variant 1 | 21 | 22 | 136 . . . 1935 |
| M713 | PTGS1: prostaglandin-endoperoxide synthase 1 (prostaglandin G/H synthase and cyclooxygenase), transcript variant 2 | 23 | 24 | 136 . . . 1824 |
| OV55 | S100A1: S100 calcium-binding protein A1 | 25 | 26 | 114 . . . 398 |
| M458 | SCGB2A1: secretoglobin, family 2A, member 1 | 27 | 28 | 65 . . . 352 |
| M714 | SLC39A4: solute carrier family 39 (zinc transporter), member 4, variant 1 | 29 | 30 | 101 . . . 2044 |
| M715 | SLC39A4: solute carrier family 39 (zinc transporter), member 4, variant 2 | 31 | 32 | 101 . . . 1762 |
| M185A | SLPI: secretory leukocyte protease inhibitor (antileukoproteinase) | 33 | 34 | 23 . . . 421 |
| OV65 | SPON1: VSGP/F-spondin | 35 | 36 | 25 . . . 2448 |
| M476 | TACSTD2: tumor-associated calcium signal transducer 2 | 37 | 38 | 616 . . . 1587 |
| M716 | WFDC2: WAP four-disulfide core domain 2, variant 1 | 39 | 40 | 28 . . . 402 |
| M717 | WFDC2: WAP four-disulfide core domain 2, variant 2 | 41 | 42 | 67 . . . 288 |
| M724 | MGC13057: hypothetical protein MGC13057 | 43 | 44 | 339 . . . 626 |

The invention relates to newly discovered markers, identified in Table 1 that are associated with the cancerous state of ovarian cells. It has been discovered that the higher than normal level of expression of any of these markers or combination of these markers correlates with the presence of ova- Definitions As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids can include DNA (e.g., cDNA) comprising the entire or a partial sequence of any of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43. The marker nucleic acids also can include RNA comprising the entire or a partial sequence corresponding to any of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43, or the complement of such a sequence, wherein all thymidine residues are replaced with uridine residues. A "marker protein" is a protein encoded by or corresponding to a marker of the invention. A marker protein comprises the entire or partial sequence of any of SEQ ID NO: 2, SEQ ID NO: 4, SEQ ID NO: 6, SEQ ID NO: 8, SEQ ID NO: 10. SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, or SEQ ID NO: 44. The terms "protein" and "polypeptide' are used interchangeably.

A "marker set" is a group of more than one marker.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

"Ovarian cancer" as used herein includes carcinomas, (e.g., carcinoma in situ, invasive carcinoma, metastatic carcinoma) and pre-malignant conditions.

An "ovary-associated" body fluid is a fluid which, when in the body of a patient, contacts or passes through ovarian cells or into which cells or proteins shed from ovarian cells e.g., ovarian epithelium, are capable of passing. Exemplary ovary-associated body fluids include blood fluids, lymph, ascites, gynecological fluids, cystic fluid, urine, and fluids collected by peritoneal rinsing.

A "sample" or "patient sample" comprises cells obtained from the patient, e.g., a lump biopsy, body fluids including blood fluids, lymph and cystic fluids, as well as nipple aspirates. In a further embodiment, the patient sample is in vivo.

The "normal" level of expression of a marker is the level of expression of the marker in ovarian cells of a human subject or patient not afflicted with ovarian cancer.

An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, ovarian cancer is also "inhibited" if recurrence or metastasis of the cancer is reduced, slowed, delayed, or prevented.

A kit is any manufacture (e.g. a package or container) comprising at least one reagent, e.g. a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and: derivatives of all of the foregoing, which fragments and derivatives have at least an antigenic binding site. Antibody derivatives may comprise a protein or chemical moiety conjugated to an antibody moiety.

The present invention is based, in part, on newly identified markers which are over-expressed in ovarian cancer cells as compared to their expression in normal (i.e. non-cancerous) ovarian cells. The enhanced expression of one or more of these markers in ovarian cells is herein correlated with the cancerous state of the tissue. The invention provides compositions, kits, and methods for assessing the cancerous state of ovarian cells (e.g. cells obtained from a human, cultured human cells, archived or preserved human cells and in vivo cells) as well as treating patients afflicted with ovarian cancer.

The compositions, kits, and methods of the invention have the following uses, among others: assessing whether a patient is afflicted with ovarian cancer; assessing the stage of ovarian cancer in a human patient; assessing the grade of ovarian cancer in a patient; assessing the benign or malignant nature of ovarian cancer in a patient; assessing the metastatic potential of ovarian cancer in a patient; determining if breast cancer has metastasized; predicting the clinical outcome of a breast cancer patient; assessing the histological type of neoplasm (e.g. serous, mucinous, endometroid, or clear cell neoplasm) associated with ovarian cancer in a patient; making antibodies, antibody fragments or antibody derivatives that are useful for treating ovarian cancer and/or assessing whether a patient is afflicted with ovarian cancer; assessing the presence of ovarian cancer cells; assessing the efficacy of one or more test compounds for inhibiting ovarian cancer in a patient; assessing the efficacy of a therapy for inhibiting ovarian cancer in a patient; monitoring the progression of ovarian cancer in a patient; selecting a composition or therapy for inhibiting ovarian cancer in a patient; treating a patient afflicted with ovarian cancer; inhibiting ovarian cancer in a patient; assessing the ovarian carcinogenic potential of a test compound; and preventing the onset of ovarian cancer in a patient at risk for developing ovarian cancer.

The invention thus includes a method of assessing whether a patient is afflicted with ovarian cancer which includes assessing whether the patient has pre-metastasized ovarian cancer. This method comprises comparing the level of expression of a marker of the invention (listed in Table 1) in a patient sample and the normal level of expression of the marker in a control, e.g., a non-ovarian cancer sample. A significantly higher level of expression of the marker in the patient sample as compared to the normal level is an indication that the patient is afflicted with ovarian cancer.

Gene delivery vehicles, host cells and compositions (all described herein) containing nucleic acids comprising the entirety, or a segment of 15 or more nucleotides, of any of the sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, or SEQ ID NO: 43 or the complement of such sequences, and polypeptides comprising the entirety, or a segment of 10 or more amino acids, of any of the sequences of SEQ ID NO: 2, SEQ ID NO: 4, SEQ ID NO: 6, SEQ ID NO: 8, SEQ ID NO: 10. SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 are also provided by this invention.

As described herein, ovarian cancer in patients is associated with an increased level of expression of one or more markers of the invention. While, as discussed above, some of these changes in expression level result from occurrence of the ovarian cancer, others of these changes induce, maintain, and promote the cancerous state of ovarian cancer cells. Thus, ovarian cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an antisense oligonucleotide can be provided to the ovarian cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein.

The expression and/or function of a marker may also be inhibited by treating the ovarian cancer cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit ovarian cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in ovarian cancer cells and the level of expression of the same marker in normal ovarian cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal ovarian tissue.

It is recognized that certain marker proteins are secreted from ovarian cells (i.e. one or both of normal and cancerous cells) to the extracellular space surrounding the cells. These markers are preferably used in certain embodiments of the compositions, kits, and methods of the invention, owing to the fact that such marker proteins can be detected in an ovary-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques.

It is a simple matter for the skilled artisan to determine whether any particular marker protein is a secreted protein. In order to make this determination, the marker protein is expressed in, for example, a mammalian cell, preferably a human ovarian cell line, extracellular fluid is collected, and the presence or absence of the protein in the extracellular fluid is assessed (e.g. using a labeled antibody which binds specifically with the protein).

The following is an example of a method which can be used to detect secretion of a protein. About $8 \times 10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE™ (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-$^{35}$S™ reagent (ICN Catalog no. 51006) are added to each well. The wells are maintained under the 5% $CO_2$ atmosphere described above and incubated at 37° C. for a selected period.

Following incubation, 150 microliters of conditioned medium is removed and centrifuged to remove floating cells and debris. The presence of the protein in the supernatant is an indication that the protein is secreted.

Examples of ovary-associated body fluids include blood fluids (e.g. whole blood, blood serum, blood having platelets removed therefrom, etc.), lymph, ascitic fluids, gynecological fluids (e.g. ovarian, fallopian, and uterine secretions, menses, vaginal douching fluids, fluids used to rinse ovarian cell samples, etc.), cystic fluid, urine, and fluids collected by peritoneal rinsing (e.g. fluids applied and collected during laparoscopy or fluids instilled into and withdrawn from the peritoneal cavity of a human patient). In these embodiments, the level of expression of the marker can be assessed by assessing the amount (e.g. absolute amount or concentration) of the marker protein in an ovary-associated body fluid obtained from a patient. The fluid can, of course, be subjected to a variety of well-known post-collection preparative and storage techniques (e.g. storage, freezing, ultrafiltration, concentration, evaporation, centrifugation, etc.) prior to assessing the amount of the marker in the fluid.

Many ovary-associated body fluids (i.e. usually excluding urine) can have ovarian cells, e.g. ovarian epithelium, therein, particularly when the ovarian cells are cancerous, and, more particularly, when the ovarian cancer is metastasizing. Cell-containing fluids which can contain ovarian cancer cells include, but are not limited to, peritoneal ascites, fluids collected by peritoneal rinsing, fluids collected by uterine rinsing, uterine fluids such as uterine exudate and menses, pleural fluid, and ovarian exudates. Thus, the compositions, kits, and methods of the invention can be used to detect expression of marker proteins having at least one portion which is displayed on the surface of cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods (e.g. the SIGNALP program; Nielsen et al., 1997, *Protein Engineering* 10:1-6) may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the cell (e.g. using a labeled antibody which binds specifically with a cell-surface domain of the protein).

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) or derivative which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with several marker nucleic acids are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal ovarian cells and cancerous ovarian cells.

It is understood that by routine screening of additional patient samples using one or more of the markers of the invention, it will be realized that certain of the markers are over-expressed in cancers of various types, including specific ovarian cancers, as well as other cancers such as breast cancer, cervical cancer, etc. For example, it will be confirmed that some of the markers of the invention are over-expressed in most (i.e. 50% or more) or substantially all (i.e. 80% or more) of ovarian cancer. Furthermore, it will be confirmed that certain of the markers of the invention are associated with ovarian cancer of various stages (i.e. stage I, II, III, and IV ovarian cancers, as well as subclassifications IA, IB, IC, IIA, IIB, IIC, IIIA, IIIB, and IIIC, using the FIGO Stage Grouping system for primary carcinoma of the ovary; 1987, *Am. J. Obstet. Gynecol.* 156:236), of various histologic subtypes (e.g. serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Müllerian) mixed tumor, mesonephroid tumor, malignant carcinoma, Brenner tumor, mixed epithelial tumor, and undifferentiated carcinoma, using the WHO/FIGO system for classification of malignant ovarian tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue}). In addition, as a greater number of patient samples are assessed for altered expression of the markers of the invention and the outcomes of the individual patients from whom the samples were obtained are correlated, it will also be confirmed that alteredexpression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of ovarian cancer in patients. In addition, these compositions, kits, and methods can be used to detect and differentiate epithelial, stromal, and germ cell ovarian cancers.

When the compositions, kits, and methods of the invention are used for characterizing one or more of the stage, grade, histological type, and benign/malignant nature of ovarian cancer in a patient, it is preferred that the marker or panel of markers of the invention is selected such that a positive result is obtained in at least about 20%, and preferably at least about 40%, 60%, or 80%, and more preferably in substantially all patients afflicted with an ovarian cancer of the corresponding stage, grade, histological type, or benign/malignant nature. Preferably, the marker or panel of markers of the invention is selected such that a positive predictive value (PPV) of greater than about 10% is obtained for the general population (more preferably coupled with an assay specificity greater than 99.5%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with ovarian cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-ovarian origin in a patient sample), it is preferable that the marker of the invention used therein be a marker which has a restricted tissue distribution, e.g. normally not expressed in a non-epithelial tissue, and more preferably a marker which is normally not expressed in a non-ovarian tissue.

Only a small number of markers are known to be associated with ovarian cancers (e.g. AKT2, Ki-RAS, ERBB2, c-MYC, RB1, and TP53; Lynch, supra). These markers are not, of course, included among the markers of the invention, although they may be used together with one or more markers of the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing ovarian cancer and their medical advisors. Patients recognized as having an enhanced risk of developing ovarian cancer include, for example, patients having a familial history of ovarian cancer, patients identified as having a mutant oncogene (i.e. at least one allele), and patients of advancing age (i.e. women older than about 50 or 60 years).

The level of expression of a marker in normal (i.e. non-cancerous) human ovarian tissue can be assessed in a variety of ways. In one embodiment, this normal level of expression is assessed by assessing the level of expression of the marker in a portion of ovarian cells which appears to be non-cancerous and by comparing this normal level of expression with the level of expression in a portion of the ovarian cells which is suspected of being cancerous. For example, when laparoscopy or other medical procedure, reveals the presence of a lump on one portion of a patient's ovary, but not on another portion of the same ovary or on the other ovary, the normal level of expression of a marker may be assessed using one or both or the non-affected ovary and a non-affected portion of the affected ovary, and this normal level of expression may be compared with the level of expression of the same marker in an affected portion (i.e. the lump) of the affected ovary. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer afflicted patient, from a patient sample obtained from a patient before the suspected onset of ovarian cancer in the patient, from archived patient samples, and the like.

The invention includes compositions, kits, and methods for assessing the presence of ovarian cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of ovarian cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal ovarian cells, a sample of ovarian cancer cells, and the like.

The invention also includes a method of making an isolated hybridoma which produces an antibody useful for assessing whether patient is afflicted with an ovarian cancer. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting ovarian cancer cells. As described above, differences in the level of expression of the markers of the invention correlate with the cancerous state of ovarian cells. Although it is recognized that changes in the levels of expression of certain of the markers of the invention likely result from the cancerous state of ovarian cells, it is likewise recognized that changes in the levels of expression of other of the markers of the invention induce, maintain, and promote the cancerous state of those cells. Thus, compounds which inhibit an ovarian cancer in a patient will cause the level of expression of one or more of the markers of the invention to change to a level nearer the normal level of expression for that marker (i.e. the level of expression for the marker in non-cancerous ovarian cells).

This method thus comprises comparing expression of a marker in a first ovarian cell sample and maintained in the presence of the test compound and expression of the marker in a second ovarian cell sample and maintained in the absence of the test compound. A significantly reduced expression of a marker of the invention in the presence of the test compound is an indication that the test compound inhibits ovarian cancer. The ovarian cell samples may, for example, be aliquots of a single sample of normal ovarian cells obtained from a patient, pooled samples of normal ovarian cells obtained from a patient, cells of a normal ovarian cell line, aliquots of a single sample of ovarian cancer cells obtained from a patient, pooled samples of ovarian cancer cells obtained from a patient, cells of an ovarian cancer cell line, or the like. In one embodiment, the samples are ovarian cancer cells obtained from a patient and a plurality of compounds known to be effective for inhibiting various ovarian cancers are tested in order to identify the compound which is likely to best inhibit the ovarian cancer in the patient.

This method may likewise be used to assess the efficacy of a therapy for inhibiting ovarian cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention then the therapy is efficacious for inhibiting ovarian cancer. As above, if samples from a selected patient are used in this method, then alternative therapies can be assessed in vitro in order to select a therapy most likely to be efficacious for inhibiting ovarian cancer in the patient.

As described above, the cancerous state of human ovarian cells is correlated with changes in the levels of expression of the markers of the invention. The invention includes a method for assessing the human ovarian cell carcinogenic potential of a test compound. This method comprises maintaining separate aliquots of human ovarian cells in the presence and absence of the test compound. Expression of a marker of the invention in each of the aliquots is compared. A significantly higher level of expression of a marker of the invention in the aliquot maintained in the presence of the test compound (relative to the aliquot maintained in the absence of the test compound) is an indication that the test compound possesses human ovarian cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid-molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3'untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6): 569-84; Helene (1992) *Ann. N.Y. Acad. Sci.* 660:27-36; and Maher (1992) *Bioassays* 14(12): 807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17): 3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17): 3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequences listed in Table 1. Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM 120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its-amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3): 327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum.*

*Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of single polypeptides. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in an ovary-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention may also be used as therapeutic agents in treating cancers. In a preferred embodiment, completely human antibodies of the invention are used for therapeutic treatment of human cancer patients, particularly those having an ovarian cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Armon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.,* 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Recombinant Expression Vectors and Host Cells

Another aspect of the invention pertains to vectors, preferably expression vectors, containing a nucleic acid encoding a marker protein (or a portion of such a protein). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g.; polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic- and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells intowhich a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the a marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced. Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out"

vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein. Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283, 317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an ovarian cancer marker protein identified herein, the known binding partner and/or substrate of same, and the test compound. Test compounds can be supplied from any source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtiter plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibitor enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J. Mol. Recognit.* 11:141-148; Hage and Tweed, 1997, *J. Chromatogr. B. Biomed. Sci. Appl.,* 699:499-525). Gel electrophoresis may also be employed to separate complexed molecules from unbound species (see, e.g., Ausubel et al (eds.), as described in: Current Protocols in Molecular Biology, J. Wiley & Sons, New York. 1999). In this technique, protein or nucleic acid complexes are separated based on size or charge, for example. In order to maintain the binding interaction during the electrophoretic process, non-denaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the ovarian epithelium). A method for lipidation of antibodies is described by Cruikshank et al. (1997) *J. Acquired Immune Deficiency Syndromes and Human Retrovirology* 14:193.

The invention also provides vaccine compositions for the prevention and/or treatment of ovarian cancer. The invention provides ovarian cancer vaccine compositions in which a protein of a marker of Table 1, or a combination of proteins of the markers of Table 1, are introduced into a subject in order to stimulate an immune response against the ovarian cancer. The invention also provides ovarian cancer vaccine compositions in which a gene expression construct, which expresses a marker or fragment of a marker identified in Table 1, is introduced into the subject such that a protein or fragment of a protein encoded by a marker of Table 1 is produced by transfected cells in the subject at a higher than normal level and elicits an immune response.

In one embodiment, an ovarian cancer vaccine is provided and employed as an immunotherapeutic agent for the prevention of ovarian cancer. In another embodiment, an ovarian, cancer vaccine is provided and employed as an immunotherapeutic agent for the treatment of ovarian cancer.

By way of example, an ovarian cancer vaccine comprised of the proteins of the markers of Table 1, may be employed for the prevention and/or treatment of ovarian cancer in a subject by administering the vaccine by a variety of routes, e.g., intradermally, subcutaneously, or intramuscularly. In addition, the ovarian cancer vaccine can be administered together with adjuvants and/or immunomodulators to boost the activity of the vaccine and the subject's response. In one embodiment, devices and/or compositions containing the vaccine, suitable for sustained or intermittent release could be, implanted in the body or topically applied thereto for the relatively slow release of such materials into the body. The ovarian cancer vaccine can be introduced along with immunomodulatory compounds, which can alter the type of immune response produced in order to produce a response which will be more effective in eliminating the cancer.

In another embodiment, an ovarian cancer vaccine comprised of an expression construct of the markers of Table 1, may be introduced by injection into muscle or by coating onto microprojectiles and using a device designed for the purpose to fire the projectiles at high speed into the skin. The cells of the subject will then express the protein(s) or fragments of proteins of the markers of Table 1 and induce an immune response. In addition, the ovarian cancer vaccine may be introduced along with expression constructs for immunomodulatory molecules, such as cytokines, which may increase the immune response or modulate the type of immune response produced in order to produce a response which will be more effective in eliminating the cancer.

The marker nucleic acid molecules of the present invention can also be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing ovarian cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit ovarian cancer or to treat or prevent any other disorder {i.e. in order to understand any ovarian carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. an ovary-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELI-SAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6): 141-8; Hage, D. S., and Tweed, S. A. *J Chromatogr B Biomed Sci Appl* 1997 Oct. 10; 699(1-2): 499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from ovarian cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from ovarian cancer or from non-ovarian cancer cells of ovarian tissue. The choice of the cell source is dependent on the use of the relative expression level. Using expression found in normal tissues as a mean expression score aids in validating whether the marker assayed is ovarian specific (versus normal cells). In addition, as more data is accumulated, the mean expression value can be revised, providing improved relative expression values based on accumulated data. Expression data from ovarian cells provides a means for grading the severity of the ovarian cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivatives thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from ovarian cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether ovarian cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e.g. an ovary-associated body fluid such as a urine sample). Such kits can be used to determine if a subject is suffering from or is at increased risk of developing ovarian cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

Agents or modulators which have a stimulatory or inhibitory effect on expression of a marker of the invention can be administered to individuals to treat (prophylactically or therapeutically) ovarian cancer in the patient. In conjunction with such treatment, the pharmacogenomics (i.e., the study of the relationship between an individuals genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the level of expression of a marker of the invention in an individual can be determined to thereby select appropriate agent(s) for therapeutic or prophylactic treatment of the individual.

Pharmacogenomics deals with clinically significant variations in the response to drugs due to altered drug disposition and abnormal action in affected persons. See, e.g., Linder (1997) *Clin. Chem.* 43(2): 254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for ovarian cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of marker gene(s) during the course of treatment may indicate ineffective dosage and the desirability of increasing the dosage. Conversely, decreased expression of the marker gene(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has ovarian cancer or a pre-disposition to ovarian cancer, wherein the method comprises the steps of determining the presence or absence of a marker and based on the presence or absence of the marker, determining whether the subject has ovarian cancer or a pre-disposition to ovarian cancer and/or recommending a particular treatment for ovarian cancer or pre-ovarian cancer condition.

The present invention further provides in an electronic system and/or in a network, a method for determining whether a subject has ovarian cancer or a pre-disposition to ovarian cancer associated with a marker wherein the method comprises the steps of determining the presence or absence of the marker, and based on the presence or absence of the marker, determining whether the subject has ovarian cancer or a pre-disposition to ovarian cancer, and/or recommending a particular treatment for the ovarian cancer or pre-ovarian cancer condition. The method may further comprise the step of receiving phenotypic information associated with the subject and/or acquiring from a network phenotypic information associated with the subject.

The present invention also provides in a network, a method for determining whether a subject has ovarian cancer or a pre-disposition to ovarian cancer associated with a marker, said method comprising the steps of receiving information associated with the marker receiving phenotypic information associated with the subject, acquiring information from the network corresponding to the marker and/or ovarian cancer, and based on one or more of the phenotypic information, the marker, and the acquired information, determining whether the subject has a ovarian cancer or a pre-disposition to ovarian cancer. The method may further comprise the step of recommending a particular treatment for the ovarian cancer or pre-ovarian cancer condition.

The present invention also provides a business method for determining whether a subject has ovarian cancer or a pre-disposition to ovarian cancer, said method comprising the steps of receiving information associated with the marker, receiving phenotypic information associated with the subject, acquiring information from the network corresponding to the marker and/or ovarian cancer, and based on one or more of the phenotypic information, the marker, and the acquired information, determining whether the subject has ovarian cancer or a pre-disposition to ovarian cancer. The method may further comprise the step of recommending a particular treatment for the ovarian cancer or pre-ovarian cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis df their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of ovarian cancer, progression of ovarian cancer, and processes, such a cellular transformation associated with ovarian cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

E. Surrogate Markers

The markers of the invention may serve as surrogate markers for one or more disorders or disease states or for conditions leading up to disease states, and in particular, ovarian cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

EXAMPLE 1

Identification of Ovarian Cancer Markers by cDNA and Tissue Microarrays

Materials and Methods

Sample Collection and RNA Preparation

Ovarian tissues were collected and snap frozen in liquid nitrogen. The histology and cellular composition of tissues were confirmed before RNA extraction was performed. Total RNA was extracted from the frozen tissues using Trizol Reagent (Life Technologies) followed by a secondary clean up step with Qiagen's RNeasy kit to increase RNA probe labeling efficiency (Qiagen, Valencia Calif. Only RNA with a 28S/18S ribosomal RNA ratio of at least 1.0, calculated from ethidium staining of the RNA after electrophoresis on agarose gels, was used in this study.

cDNA Microarray Hybridization cDNA microarrays containing 30,732 Unigene clones from Research Genetics (Hunstville, Ala.) were generated on nylon filters. A total of 4-6 ug of total RNA was used as template to generate radioactively labeled cDNA by reverse transcription with $^{33}$P-dCTP, oligo dT-30 primer and Superscript II Reverse Transcriptase (Life Technologies). $^{33}$P-labeled first strand cDNA was pre-annealed with cot-1 DNA and poly-dA 40-60 (Pharmacia, Peapack, N.J.) to reduce non-specific hybridization. Each filter was hybridized at 65° C. for 16 hours with approximately $6 \times 10^6$ counts of labeled probe in a buffer containing 7% sodium dodecyl sulfate (SDS), 250 mM $Na_3PO_4$ (pH 7.2), 1 mM EDTA, 0.5% Casein Hammerstein and 0.1 mg/ml of denatured salmon sperm DNA. After the filters were washed with 4% and 1% SDS wash buffer (20 mM $Na_3PO_4$ (pH 7.2), 1 mM EDTA and 4% or 1% SDS), they were exposed to Fuji Phosphoimager screens and scanned using a Fuji scanner BAS 2500. Spots were quantitated using an automated array analysis program, Grid Guru v1.0, developed at Millennium Pharmaceuticals, Inc.

Marker Scoring Algorithm and Data Analysis

To correct for differences in hybridization efficiency, the digitized data from each microarray filter was normalized by the median intensity of all spots on that filter. Both array-based and gene-based hierarchical clustering was performed and visualized using Stanford's Gene Cluster and Tree View software. Differentially expressed genes were ranked by calculating the Marker Score for each gene.

To compute Marker Score, the samples were divided into control and tester groups. The starting point for the Marker Score is average fold change (ratio) of the tester samples above the control samples. The score was designed to reflect both the degree of change (the expression ratio) and the number of tester samples showing differential expression, while not being dominated by a small fraction of tester samples with very high values. To reduce this "outlier" effect, genes were treated with expression ratios greater than 10 as not meaningfully different from those with ratios of 10. This desired performance from a Marker Score was accomplished by transforming the tester:control expression ratio using an asymptotic compression function before taking the average fold-change across tester samples. A Marker Score has a value of 1 when the testers do not appear to be expressed more highly than the controls and a value greater than 1 otherwise. A Marker Score cannot exceed a value of 10 for any gene.

The Marker Score $S_g$ for gene g is therefore computed as the average of the ratios of weighted intensities of the individual testers and a control level as follows:

$$S_g = (\Sigma S_{gs})/N_{tester}$$

$S_{gs} = C(x_{gs}/(k + x_g^Q))$, where $S_{gs}$ represents the Marker Score for gene g and the sample s, $C(r)$ is the compression function $C(r) = A(1 - e^{-r/A})$ for $r>1$, and $C(r) = 1$ for $r<1$, A is an upper asymptote on the fold-change value (we used 10), $x_{gs}$ is the expression value of gene g on sample s, $x_g^Q$ is the Qth percentile of the control samples' expression value; typically Q=50, k is a constant reflecting the additive noise in the data, i.e., the fixed component of the variance in repeated measurements. A value of 0.25 was derived for this parameter from calibration experiments using microarray technology.

$N_{tester}$ The number of tester samples

Results

Marker Selection

All of the markers listed in Table 1 were identified by transcription profiling as defined in the materials and methods section. mRNA from markers M138, M437, M445, M452A, M712, M472, M590A, M713, M458, M714, M715, M185A, M476, M716, M717 and M724 was obtained from 67 ovarian tumors of various histotypes and stages and 96 non-ovarian tumor tissues including normal ovarian epithelium, benign conditions, other normal tissues and other abnormal tissues. Clones having expression at least three-fold higher in at least 10% of ovarian tumors, as compared to their expression in non-ovarian tumor tissue, were designated as ovarian cancer specific markers. These cDNA clones were selected to have their protein-encoding transcript sequences determined.

mRNA from markers OV32A, OV33A, OV52A, OV51A, OV55 and OV65 was obtained from 9 normal ovarian epithelial, 11 stage I/II ovarian cancer tumors and 25 stage III/IV ovarian cancer tumors. Clones having expression of at least two-fold higher in ovarian tumors as compared to their expression in non-ovarian tumor tissues in at least 4 tumor samples were selected to have their protein-encoding transcript sequence determined.

In order to determine the full-length protein-encoding transcripts for the selected cDNA clones, the sequence(s) of the selected clones were used to query the public and proprietary sequence databases in order to identify other EST sequences or clusters with significant overlap. Briefly, BLAST analysis, against both public and proprietary sequence databases, of EST sequences known to be associated with each clone was performed, either directly or in the context of automatically, high-stringency assembled contiguous sequences. An identification of protein sequence corresponding to the clone was accomplished by obtaining one of the following:

1) a direct match between the protein sequence and at least one EST sequence in one of its 6 possible translations;
2) a direct match between the nucleotide sequence for the mRNA corresponding to the protein sequence and at least one EST sequence;
3) a match between the protein sequence and a contiguous assembly (contig) of the EST sequences with other available EST sequences in the databases in one of its 6 possible translations; or
4) a match between the nucleotide sequence for the mRNA corresponding to the protein sequence and a contiguous assembly of the EST sequences with other available EST sequences in the databases in one of its 6 possible translations.

Thus, contiguous EST sequences and/or clusters were assembled into protein-encoding transcripts. Alternative transcript analysis for all of the claimed markers was undertaken as follows:

1) Using existing mappings of known nucleotide sequences for any given marker gene to the human genome sequence and by additionally mapping novel nucleotide sequences for any given marker gene onto the human genome sequence (e.g. using resources like the "UCSC genome browser" or in-house resources of similar functionality in conjunction with algorithms like BLAT that allow a rapid and precise mapping of search sequences onto genomic sequence), the exon-intron structure of a marker gene was established, taking additionally into account EST sequences matching the same gene.
2) PCR primers were designed to amplify the coding sequence of a given marker gene from the tissue of interest and control samples. Any alternative 5' or 3' ends of a marker gene arising from this analysis with the potential to alter the coding sequence led to the design of an additional primer specific for this alternative end.
3) PCR products obtained with cDNA templates derived from ovarian tumor specimens were cloned into a plasmid vector and characterized by DNA sequence analysis. Typically, 96 clones were analyzed by restriction digestion and gel electrophoresis of the PCR products or by DNA sequence analysis.
4) Clones representative of alternative gene transcripts occurring at a frequency of 2% or greater were sequenced.
5) The differential gene expression of the identified alternative transcripts was confirmed by TAQMAN® quantitative PCR (Applied Biosystems) in cDNA prepared from the patient tissue specimens. Splice-form specific TaqMan primers and probe regent sets were developed for each transcript and similar amplification efficiencies were obtained with all reagents sets for each gene.
6) The identification of protein sequence corresponding to these alternative transcripts was accomplished by the identification of the open reading frame (ORF) contained within a manually curated assembly (contig) based on all: available sequences.

EXAMPLE 2

Gene Expression Analysis by End-Point PCR

Materials and Methods

Briefly, total RNA from different samples was pooled to be used as template to generate first strand cDNA. The ovarian panel consisted of patient samples of a "ovarian tumor pool" (4 tumor samples containing seous and clear cell ovarian tumors) and a "ovarian normal pool" (3 normal ovarian epithelia).

Total RNA was prepared from patient samples by a single step extraction method using TRIZOL Reagent according to the manufacturer's instructions (Invitrogen). Each RNA preparation was treated with DNase I (Ambion) at 37° C. for 1 hour. RNA from each patient sample was pooled into one of the two pools, e.g., ovarian tumor pool and ovarian normal pool. ThermoScript RT-PCR System (Invitrogen, San Diego, Calif.) was used to obtain cDNA from each of the pools. Briefly, 1 µg RNA was denatured at 65° C. for 5 min with 1 µl of 50 µM oligo (dT)20 primer in a 10 µl volume according to the manufacturer's instructions. The reaction was terminated by incubation at 85° C. for 5 min. The final product was diluted with water to a final volume of 100 µl.

Gene specific primers were designed just outside the Open Reading Frame (as shown in Table 2 categories "Endpoint PCR Primer 1" and "Endpoint PCR Primer 2"). The PCR conditions were optimized for the primers and the size of the product expected. 2 µl of cDNA was used in a 20 µl reaction with touchdown cycling conditions. The products were run on an ethidium bromide containing agarose gel. The gel picture was then semi-quantitatively analyzed and scored.

The ethidium bromide agarose gel pictures of the end-point PCR on the tissue panel were scored on a scale of 1-5. Each picture was scored independently by three people based on visual band intensity and the results were compiled. The scores were compared to confirm all three agreed on the relative intensities of the bands and modifications were made where needed. The median of the three scores was then recorded as the final score.

As shown in Table 2 every marker of the invention tested in End-point PCR was expressed at higher levels in the ovarian tumor pool when compared to the ovarian normal pool.

Results

TABLE 2

Endpoint PCR Data.

| Marker | Endpoint PCR Primer 1 | Endpoint PCR Primer 2 | Ovarian Tumor Pool | Ovarian Normal Pool |
|---|---|---|---|---|
| M138 | 62-81 | 898-920 | 1 | 0 |
| OV32A | 87-108 | 1107-1128 | 3 | 0 |
| OV33A | 237-254 | 1082-1103 | 5 | 1 |
| M472 | 62-80 | 458-480 | 2 | 0 |
| M590A | 751-772 | 1114-1135 | 5 | 1 |
| OV52A | 2-23 | 927-948 | 5 | 0 |
| OV51A | 91-108 | 1968-1989 | 4 | 0 |
| M713 | 91-108 | 1857-1878 | 4 | 0 |
| OV55 | 17-36 | 485-504 | 4 | 0 |
| M458 | 1-22 | 373-394 | 5 | 0 |
| M185A | 13-33 | 519-538 | 3 | 1 |
| OV65 | 106-123 | 2444-2465 | 5 | 0 |
| M476 | 152-171 | 1742-1761 | 2 | 0 |
| M716 | 20-39 | 414-432 | 1 | 0 |
| M717 | 95-114 | 403-422 | 3 | 1 |
| M724 | 275-296 | 638-659 | 5 | 1 |

OTHER EMBODIMENTS

Those skilled in the art will recognize, or be able to ascertain using no more than routine experimentation, many equivalents to the specific embodiments of the invention described herein. Such equivalents are intended to be encompassed by the following claims:

What is claimed:

1. A method of assessing whether a patient is afflicted with ovarian cancer, the method comprising:
   a) determining the level of expression of the SLC39A4 marker in a patient sample, wherein the SLC39A4 marker is a marker that is at least 95% identical to SEQ ID NO:31 and the same length as SEQ ID NO:31 or a marker that is at least 95% identical to SEQ ID NO:32 and the same length as SEQ ID NO:32;
   b) determining the level of expression of the SLC39A4 marker in a control non-ovarian cancer sample; and
   c) comparing the level of expression of the SLC39A4 marker in the patient sample to the level of expression of the SLC39A4 marker in the control sample; wherein an increase in the level of expression of the SLC39A4 marker in the patient sample as compared to the level of expression of the SLC39A4 marker in the control sample is an indication that the patient is afflicted with ovarian cancer, thereby assessing whether a patient is afflicted with ovarian cancer.

2. The method of claim 1, wherein the level of expression of the SLC39A4 marker in the control sample is determined from ovarian cells from said patient which are non-cancerous.

3. The method of claim 1, wherein the level of expression of the SLC39A4 marker in the control sample is predetermined using an average of the levels of expression from a population of subjects having no ovarian cancer.

4. The method of claim 1, wherein the patient sample comprises cells obtained from the patient.

5. The method of claim 4, wherein the cells are in fluid selected from the group consisting of blood fluids, lymph, ascites, gynecological fluids, cystic fluid, urine, and fluids collected by peritoneal rinsing.

6. The method of claim 1, wherein the level of expression of the marker in the sample is assessed by detecting the presence in the sample of a protein corresponding to the marker.

7. The method of claim 6, wherein the presence of the protein is detected using a reagent which specifically binds with the protein.

8. The method of claim 7, wherein the reagent is an antibody or an antibody fragment which binds specifically with the protein.

9. The method of claim 8, wherein the antibody is a monoclonal antibody or a polyclonal antibody, or the antibody fragment is derived from a monoclonal antibody or a polyclonal antibody.

10. The method of claim 7, wherein the reagent is labeled.

11. The method of claim 10, wherein the label is selected from the group consisting of a radio-label, a biotin-label, a chromophore-label, a fluorophore-label, and an enzyme label.

12. The method of claim 6, wherein the level of protein expression of the marker in the sample is assessed by detecting the presence in the sample of a protein of SEQ ID NO:32.

13. The method of claim 1, wherein the level of expression of the marker in the patient sample differs from the normal level of expression of the marker in the control non-ovarian cancer sample by a factor of at least about 2.

14. The method of claim 1, wherein the level of expression of the marker in the patient sample differs from the normal level of expression of the marker in the control non-ovarian cancer sample by a factor of at least about 5.

15. The method of claim 1, wherein the marker corresponds to a transcribed polynucleotide or portion thereof, wherein the polynucleotide comprises the marker.

16. The method of claim 15, wherein the transcribed polynucleotide or portion thereof consists of SEQ ID NO:31.

17. The method of claim 1, wherein the level of expression of the marker in the sample is assessed by detecting the presence in the sample of a transcribed polynucleotide or portion thereof, wherein the transcribed polynucleotide comprises the marker.

18. The method of claim 17, wherein the transcribed polynucleotide is a mRNA or a cDNA.

19. The method of claim 17, wherein the step of detecting further comprises amplifying the transcribed polynucleotide.

20. The method of claim 1, wherein the level of expression of the marker in the sample is assessed by detecting the presence in the sample of a transcribed polynucleotide which anneals with the marker or anneals with a portion of a polynucleotide wherein the polynucleotide comprises the marker, under stringent hybridization conditions.

21. The method of claim 1, wherein the level of expression of the marker in the patient sample is determined using a technique selected from the group consisting of: Northern hybridization, in situ hybridization, enzyme linked immunosorbent assay (ELISA), Western blot, immunoprecipitation, immunofluorescence, polymerase chain reaction analysis, RT-PCR, and probe array.

22. A method of assessing whether a patient is afflicted with ovarian cancer, the method comprising:
a) determining the level of expression in a patient sample of the SLC39A4 marker and an additional marker independently selected from the markers listed in Table 1, wherein the SLC39A4 marker is a marker that is at least 95% identical to the entire sequence of SEQ ID NO:31 and the same length as SEQ ID NO:31 or a marker that is at least 95% identical to the entire sequence of SEQ ID NO:32 and the same length as SEQ ID NO:32;
b) determining the level of expression of the SLC39A4 marker and the additional marker in a control non-ovarian cancer sample; and
c) comparing the level of expression of the SLC39A4 marker and the additional marker in the patient sample and in the control sample;
wherein an increase in the level of expression of the SLC39A4 marker in the patient sample as compared to the level of expression of the SLC39A4 marker in the control sample, and an increase in the level of expression of the additional marker in the patient sample as compared to the level of expression of the additional marker in the control sample is an indication that the patient is afflicted with ovarian cancer, thereby assessing whether a patient is afflicted with ovarian cancer.

23. The method of claim 22, wherein the level of expression of the SLC39A4 marker in the control sample is determined from ovarian cells from said patient which are non-cancerous.

24. The method of claim 22, wherein the level of expression of the SLC39A4 marker in the control sample is predetermined using an average of the levels of expression from a population of subjects having no ovarian cancer.

25. The method of claim 22, wherein the level of expression of at least two additional markers is determined.

26. The method of claim 22, wherein the level of expression of at least three additional markers is determined.

27. A method for determining whether a patient has ovarian cancer that has metastasized or is likely to metastasize, the method comprising comparing:
a) the level of expression of the SLC39A4 marker in a patient sample, wherein the SLC39A4 marker is a marker that is at least 95% identical to the entire sequence of SEQ ID NO:31 and the same length as SEQ ID NO:31 or a marker that is at least 95% identical to the entire sequence of SEQ ID NO:32 and the same length as SEQ ID NO:32, and
b) the level of expression of the SLC39A4 marker in a control sample from a subject having a non-metastasized ovarian cancer or no ovarian cancer,
c) wherein, a higher level of expression of the SLC39A4 marker in the patient sample as compared to the level of expression of the SLC39A4 marker in the control sample is an indication that the ovarian cancer has metastasized or is likely to metastasize, thereby determining whether a patient has ovarian cancer that has metastasized or is likely to metastasize.

* * * * *

SEQUENCE LISTING

<160> NUMBER OF SEQ ID NOS: 44

<210> SEQ ID NO 1
<211> LENGTH: 1257
<212> TYPE: DNA
<213> ORGANISM: Homo sapien
<220> FEATURE:
<221> NAME/KEY: CDS
<222> LOCATION: (27)...(863)

<400> SEQUENCE: 1

```
gaggcgcgcg ggtgaaaggc gcattg atg cag cct gcg gcg gcc tcg gag cgc      53
                             Met Gln Pro Ala Ala Ala Ser Glu Arg
                              1               5 ggc gga gca gac gct gac cac gtt cct ctc ctc ggt ctc ctc cgc ctc      101
Gly Gly Ala Asp Ala Asp His Val Pro Leu Leu Gly Leu Leu Arg Leu
 10                  15                  20                  25 cag ctc cgc gct gcc cgg cag ccg gga gcc atg cga ccc cag ggc ccc      149
Gln Leu Arg Ala Ala Arg Gln Pro Gly Ala Met Arg Pro Gln Gly Pro
                 30                  35                  40 gcc gcc tcc ccg cag cgg ctc cgc ggc ctc ctg ctc ctg ctg ctg         197
Ala Ala Ser Pro Gln Arg Leu Arg Gly Leu Leu Leu Leu Leu Leu
             45                  50                  55 cag ctg ccc gcg ccg tcg agc gcc tct gag atc ccc aag ggg aag caa      245
Gln Leu Pro Ala Pro Ser Ser Ala Ser Glu Ile Pro Lys Gly Lys Gln
         60                  65                  70 aag gcg cag ctc cgg cag agg gag gtg gtg gac ctg tat aat gga atg      293
Lys Ala Gln Leu Arg Gln Arg Glu Val Val Asp Leu Tyr Asn Gly Met
 75                  80                  85 tgc tta caa ggg cca gca gga gtg cct ggt cga gac ggg agc cct ggg      341
Cys Leu Gln Gly Pro Ala Gly Val Pro Gly Arg Asp Gly Ser Pro Gly
 90                  95                 100                 105 gcc aat ggc att ccg ggt aca cct ggg atc cca ggt cgg gat gga ttc      389
Ala Asn Gly Ile Pro Gly Thr Pro Gly Ile Pro Gly Arg Asp Gly Phe
                110                 115                 120 aaa gga gaa aag ggg gaa tgt ctg agg gaa agc ttt gag gag tcc tgg      437
Lys Gly Glu Lys Gly Glu Cys Leu Arg Glu Ser Phe Glu Glu Ser Trp
            125                 130                 135 aca ccc aac tac aag cag tgt tca tgg agt tca ttg aat tat ggc ata      485
Thr Pro Asn Tyr Lys Gln Cys Ser Trp Ser Ser Leu Asn Tyr Gly Ile
```

```
                140                 145                 150
gat ctt ggg aaa att gcg gag tgt aca ttt aca aag atg cgt tca aat    533
Asp Leu Gly Lys Ile Ala Glu Cys Thr Phe Thr Lys Met Arg Ser Asn
        155                 160                 165 agt gct cta aga gtt ttg ttc agt ggc tca ctt cgg cta aaa tgc aga    581
Ser Ala Leu Arg Val Leu Phe Ser Gly Ser Leu Arg Leu Lys Cys Arg
170                 175                 180                 185 aat gca tgc tgt cag cgt tgg tat ttc aca ttc aat gga gct gaa tgt    629
Asn Ala Cys Cys Gln Arg Trp Tyr Phe Thr Phe Asn Gly Ala Glu Cys
                190                 195                 200 tca gga cct ctt ccc att gaa gct ata att tat ttg gac caa gga agc    677
Ser Gly Pro Leu Pro Ile Glu Ala Ile Ile Tyr Leu Asp Gln Gly Ser
            205                 210                 215 cct gaa atg aat tca aca att aat att cat cgc act tct tct gtg gaa    725
Pro Glu Met Asn Ser Thr Ile Asn Ile His Arg Thr Ser Ser Val Glu
        220                 225                 230 gga ctt tgt gaa gga att ggt gct gga tta gtg gat gtt gct atc tgg    773
Gly Leu Cys Glu Gly Ile Gly Ala Gly Leu Val Asp Val Ala Ile Trp
    235                 240                 245 gtt ggc act tgt tca gat tac cca aaa gga gat gct tct act gga tgg    821
Val Gly Thr Cys Ser Asp Tyr Pro Lys Gly Asp Ala Ser Thr Gly Trp
250                 255                 260                 265 aat tca gtt tct cgc atc att att gaa gaa cta cca aaa taa            863
Asn Ser Val Ser Arg Ile Ile Ile Glu Glu Leu Pro Lys *
                270                 275 atgctttaat tttcatttgc tacctctttt tttattatgc cttggaatgg ttcacttaaa   923
tgacatttta aataagttta tgtatacatc tgaatgaaaa gcaaagctaa atatgtttac   983
agaccaaagt gtgatttcac actgttttta aatctagcat tattcatttt gcttcaatca  1043
aaagtggttt caatattttt tttagttggt tagaatactt tcttcatagt cacattctct  1103
caacctataa tttggaatat tgttgtggtc ttttgttttt tctcttagta tagcattttt  1163
aaaaaaatat aaaagctacc aatctttgta caatttgtaa atgttaagaa tttttttat   1223 atctgttaaa taaaaattat ttccaacaac ctta                              1257
```

<210> SEQ ID NO 2
<211> LENGTH: 278
<212> TYPE: PRT
<213> ORGANISM: Homo sapien

<400> SEQUENCE: 2

```
Met Gln Pro Ala Ala Ser Glu Arg Gly Gly Ala Asp Ala Asp His
1               5                   10                  15

Val Pro Leu Leu Gly Leu Leu Arg Leu Gln Leu Arg Ala Ala Arg Gln
                20                  25                  30

Pro Gly Ala Met Arg Pro Gln Gly Pro Ala Ala Ser Pro Gln Arg Leu
            35                  40                  45

Arg Gly Leu Leu Leu Leu Leu Leu Gln Leu Pro Ala Pro Ser Ser
        50                  55                  60

Ala Ser Glu Ile Pro Lys Gly Lys Gln Lys Ala Gln Leu Arg Gln Arg
65                  70                  75                  80

Glu Val Val Asp Leu Tyr Asn Gly Met Cys Leu Gln Gly Pro Ala Gly
                85                  90                  95

Val Pro Gly Arg Asp Gly Ser Pro Gly Ala Asn Gly Ile Pro Gly Thr
            100                 105                 110

Pro Gly Ile Pro Gly Arg Asp Gly Phe Lys Gly Glu Lys Gly Glu Cys
        115                 120                 125
```

```
Leu Arg Glu Ser Phe Glu Glu Ser Trp Thr Pro Asn Tyr Lys Gln Cys
            130                 135                 140

Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
        195                 200                 205

Ala Ile Ile Tyr Leu Asp Gln Gly Ser Pro Glu Met Asn Ser Thr Ile
    210                 215                 220

Asn Ile His Arg Thr Ser Ser Val Glu Gly Leu Cys Glu Gly Ile Gly
225                 230                 235                 240

Ala Gly Leu Val Asp Val Ala Ile Trp Val Gly Thr Cys Ser Asp Tyr
                245                 250                 255

Pro Lys Gly Asp Ala Ser Thr Gly Trp Asn Ser Val Ser Arg Ile Ile
            260                 265                 270

Ile Glu Glu Leu Pro Lys
            275

<210> SEQ ID NO 3
<211> LENGTH: 4039
<212> TYPE: DNA
<213> ORGANISM: Homo sapien
<220> FEATURE:
<221> NAME/KEY: CDS
<222> LOCATION: (28)...(1815)

<400> SEQUENCE: 3
cgccatcgtt ccctggctgc ttactaa gtt gga tcc gga att tct ttt caa ccg        54
                                Val Gly Ser Gly Ile Ser Phe Gln Pro
                                  1               5 gga gcc att ggt gtc gaa gtg tct gca atg aac ccc gtg aat gct act       102
Gly Ala Ile Gly Val Glu Val Ser Ala Met Asn Pro Val Asn Ala Thr
 10              15                  20                  25 gct ctc tac att tcc gcg agc cgc cta gtg ctc aac tac gac ccc gga       150
Ala Leu Tyr Ile Ser Ala Ser Arg Leu Val Leu Asn Tyr Asp Pro Gly
                 30                  35                  40 gac ccc aag gcg ttt act gag att aac agg ctc ttg cct tac ttc cga       198
Asp Pro Lys Ala Phe Thr Glu Ile Asn Arg Leu Leu Pro Tyr Phe Arg
             45                  50                  55 cag tcc ctt tcg tgc tgt gtt tgc gga cat ttg cta caa gat cct att       246
Gln Ser Leu Ser Cys Cys Val Cys Gly His Leu Leu Gln Asp Pro Ile
         60                  65                  70 gca ccc acc aac tcc acc tgc caa cat tat gtc tgc aaa act tgt aaa       294
Ala Pro Thr Asn Ser Thr Cys Gln His Tyr Val Cys Lys Thr Cys Lys
     75                  80                  85 ggc aag aaa atg atg atg aaa cct tcc tgt agc tgg tgc aaa gac tat       342
Gly Lys Lys Met Met Met Lys Pro Ser Cys Ser Trp Cys Lys Asp Tyr
 90                  95                 100                 105 gag cag ttt gag gaa aac aag cag tta agc atc cta gtg aac tgc tac       390
Glu Gln Phe Glu Glu Asn Lys Gln Leu Ser Ile Leu Val Asn Cys Tyr
                 110                 115                 120 aaa aaa cta tgc gag tat ata aca cag act aca ctg gca cgg gat ata       438
Lys Lys Leu Cys Glu Tyr Ile Thr Gln Thr Thr Leu Ala Arg Asp Ile
             125                 130                 135 ata gaa gca gtt gac tgt tct tct gat att ttg gct ttg ctt aat gat       486
```

```
Ile Glu Ala Val Asp Cys Ser Ser Asp Ile Leu Ala Leu Leu Asn Asp
        140                 145                 150 gga tca ttg ttt tgt gag gag aca gaa aaa ccc tca gat tca tcc ttt      534
Gly Ser Leu Phe Cys Glu Glu Thr Glu Lys Pro Ser Asp Ser Ser Phe
    155                 160                 165 act ttg tgt ttg aca cat tcc cct tta cct tca acc tca gaa ccc aca      582
Thr Leu Cys Leu Thr His Ser Pro Leu Pro Ser Thr Ser Glu Pro Thr
170                 175                 180                 185 act gat cct caa gct agt tta tct cca atg tct gaa agc acc ctc agc      630
Thr Asp Pro Gln Ala Ser Leu Ser Pro Met Ser Glu Ser Thr Leu Ser
                    190                 195                 200 att gct att ggc agt tct gtt atc aat ggt ttg cct act tat aat ggg      678
Ile Ala Ile Gly Ser Ser Val Ile Asn Gly Leu Pro Thr Tyr Asn Gly
                205                 210                 215 ctt tca ata gat aga ttt ggt ata aat att cct tca cct gaa cat tca      726
Leu Ser Ile Asp Arg Phe Gly Ile Asn Ile Pro Ser Pro Glu His Ser
            220                 225                 230 aat acg att gac gta tgt aat act gtt gac ata aaa act gag gat ctg      774
Asn Thr Ile Asp Val Cys Asn Thr Val Asp Ile Lys Thr Glu Asp Leu
        235                 240                 245 tct gac agc ctg cca ccc gtt tgt gac aca gta gcc act gac tta tgt      822
Ser Asp Ser Leu Pro Pro Val Cys Asp Thr Val Ala Thr Asp Leu Cys
250                 255                 260                 265 tcc aca ggc att gat atc tgc agt ttc agt gaa gat ata aaa cct gga      870
Ser Thr Gly Ile Asp Ile Cys Ser Phe Ser Glu Asp Ile Lys Pro Gly
                    270                 275                 280 gac tct ctg tta ctg agt gtt gag gaa gta ctc cgc agc tta gaa act      918
Asp Ser Leu Leu Leu Ser Val Glu Glu Val Leu Arg Ser Leu Glu Thr
                285                 290                 295 gtt tca aat aca gag gtc tgt tgc cct aat ttg cag ccg aac ttg gaa      966
Val Ser Asn Thr Glu Val Cys Cys Pro Asn Leu Gln Pro Asn Leu Glu
            300                 305                 310 gcc act gta tcc aat gga cct ttt ctg cag ctt tct tcc cag tct ctt     1014
Ala Thr Val Ser Asn Gly Pro Phe Leu Gln Leu Ser Ser Gln Ser Leu
        315                 320                 325 agc cat aat gtt ttt atg tcc acc agt cct gca ctt cat ggg tta tca     1062
Ser His Asn Val Phe Met Ser Thr Ser Pro Ala Leu His Gly Leu Ser
330                 335                 340                 345 tgt aca gca gca act ccg aag ata gca aaa ttg aat aga aaa cga tcc     1110
Cys Thr Ala Ala Thr Pro Lys Ile Ala Lys Leu Asn Arg Lys Arg Ser
                    350                 355                 360 aga tca gag agt gac agt gag aaa gtt cag cca ctt cca att tct acc     1158
Arg Ser Glu Ser Asp Ser Glu Lys Val Gln Pro Leu Pro Ile Ser Thr
                365                 370                 375 att atc cga ggc cca aca ctg ggg gca tct gct cct gtg aca gtg aaa     1206
Ile Ile Arg Gly Pro Thr Leu Gly Ala Ser Ala Pro Val Thr Val Lys
            380                 385                 390 cgg gag agc aaa att tct ctt caa cct ata gca act gtt ccc aat gga     1254
Arg Glu Ser Lys Ile Ser Leu Gln Pro Ile Ala Thr Val Pro Asn Gly
        395                 400                 405 ggc aca aca cct aaa atc agc aaa act gta ctt tta tct act aaa agc     1302
Gly Thr Thr Pro Lys Ile Ser Lys Thr Val Leu Leu Ser Thr Lys Ser
410                 415                 420                 425 atg aaa aag agt cat gaa cat gga tcc aag aaa tct cac tct aaa acc     1350
Met Lys Lys Ser His Glu His Gly Ser Lys Lys Ser His Ser Lys Thr
                    430                 435                 440 aag cca ggt att ctt aaa aaa gac aaa gca gta aag gaa aag att cct     1398
Lys Pro Gly Ile Leu Lys Lys Asp Lys Ala Val Lys Glu Lys Ile Pro
                445                 450                 455
```

```
                                                     -continued
agt cat cat ttt atg cca gga agt cct acc aag act gtg tac aaa aaa      1446
Ser His His Phe Met Pro Gly Ser Pro Thr Lys Thr Val Tyr Lys Lys
            460                 465                 470 ccc cag gaa aag aaa ggg tgt aaa tgt ggg cgt gct act caa aat cca      1494
Pro Gln Glu Lys Lys Gly Cys Lys Cys Gly Arg Ala Thr Gln Asn Pro
    475                 480                 485 agt gtt ctt aca tgc cga ggc caa cgc tgc cct tgc tac tct aac cgc      1542
Ser Val Leu Thr Cys Arg Gly Gln Arg Cys Pro Cys Tyr Ser Asn Arg
490                 495                 500                 505 aaa gcc tgc tta gat tgt ata tgt cgt ggc tgc caa aac tcc tat atg      1590
Lys Ala Cys Leu Asp Cys Ile Cys Arg Gly Cys Gln Asn Ser Tyr Met
                510                 515                 520 gcc aat ggg gag aag aag ctg gag gca ttt gcc gtg cca gaa aag gcc      1638
Ala Asn Gly Glu Lys Lys Leu Glu Ala Phe Ala Val Pro Glu Lys Ala
            525                 530                 535 ttg gag cag acc agg ctc act ttg ggc att aac gtg act agc att gct      1686
Leu Glu Gln Thr Arg Leu Thr Leu Gly Ile Asn Val Thr Ser Ile Ala
        540                 545                 550 gtg cgt aac gct agt acc agc acc agt gta ata aat gtc aca ggg tcc      1734
Val Arg Asn Ala Ser Thr Ser Thr Ser Val Ile Asn Val Thr Gly Ser
    555                 560                 565 cca gta acg acg ttt tta gct gcc agt aca cat gat gat aaa agt ttg      1782
Pro Val Thr Thr Phe Leu Ala Ala Ser Thr His Asp Asp Lys Ser Leu
570                 575                 580                 585 gat gaa gct ata gac atg aga ttc gac tgt taa atcagtgggt cttttaaacc   1835
Asp Glu Ala Ile Asp Met Arg Phe Asp Cys *
                590                 595 tactcctggt agggaaatag ctacagtttt acggcagcta tggttctgtt ggtttaactt   1895
gccggagctc ctgcatatag atcacttgta tcaagtgttt tcattgctaa gttatatgtg   1955
ttagtgtcgg ggaaatagtt tgcagataat ggaggagtaa ccctacaact atatgtcctt   2015
agttcttaca gaacctcata gtttgagaac aaagctgatg caactgattt atacaaaatg   2075
aactttggca agaaaaataa cattaacctc attgtttatg ccatgctttt gtgcataatc   2135
aaagtttatg attaaatgta aggaagtggt atcagtcag tccataaaga ttgtgctaat    2195
ttttttgtgg aaaagtagcc attagttcag gaaactcagt gctgccttca gatgtcattg   2255
atgtttctcc tgttggaaag ctgatgtgtc cagctcaacc tttgtgctga catcatacca   2315
tttctgatca tgaaatattg gctactggtg tatgtagcag ttcttaaatc agcagtatta   2375
tgaaaaaaaa ttccccctca ttagaatgtt taagaaatct ttttaaaaag taaaattctg   2435
tcagactaca aatgtttagc tgttactcat ttctagggaa gaaattctaa atccctcctt   2495
cactttgagc agtgttctaa ttggataaat gaaggagagt agttttattc tgaaggtaat   2555
taaatttaga ctatgtagta tgtgacagaa ttttttttaaa attataaaaa gattttattt  2615
agtaattggg atttacttaa ataattttg gaataatgct cccagacttg cccagatttg    2675
tgtattgtac ttattgccac tggccgccac tttgacttat tttctctaat agtttatttg   2735
ccacagtctt tattttgaat atgctcctag ttttttttta gggtgctgtt cattatgaag   2795
gcttctttat agaggcctaa taagaatgcc ttttataaa gcctgtgcat ttaggtaggt    2855
tgaagctagg aggatttct ttagaatgct cttttgcatg taaagcacaa agtatgtttc    2915
agtttaaatg cacttcttcc ggttaatttt tatgggaag acaagtgagt cacaaacatt    2975
ctgttgaagg gaaatctagt cagttgcttg aaagagcaca gcccaaataa aacaaggact   3035
gactaggtgt aatgaaataa cctgtgattt aaaagaagag ctgcagcttt gacagtgctt   3095
atttaaagaa aaatactgct ggaaaatttc caatttctac tacgttcacc atctctagta   3155
```

```
agatctgaca tatgctgaag ttatgttttg atttggcaca cagcatgttc aatgatggtt    3215
actcgcctag tacaagacat ggagaagaaa cctttggaca cagagcagat gacacctcct    3275
tctgttttgt agtgtatcct ggtgtcattt tctgtgaatg tggtcaggta gagttgtttt    3335
tgttgttgtt gttgggcttt tttttctttt tttttttttg gtctcttttg gtggggtggg    3395
ggtgggctaa agccatagga agaaaaatgt gatgtgtcca gtatgtacta ttttgttttt    3455
gttttgcaag aagagttgaa ctattttga taacaagagt aaatggtgga aaatgcttct    3515
tagttgtctt gtctttattt gctttccaag atttggaatt ttatttaatt cctttaagtg    3575
ttagcagtgt cttatgaaac atgtatttac ctaacgtttg taacagtttt gtgttgaacc    3635
cagatgccct gctatataaa gttgtaaatc tgttctttat tcactaatga tcactgcaaa    3695
aatgattaga aatgagattg tacacatgga tgaggatata ttttgcaaat cgaccaaact    3755
ttcctaatat tatgatctta aaattcatag agtactttat tgcttcccaa gtttgataat    3815
cttgtgggtt tttttttttt ttgatgcatg ggaggttggc aatatagaca aagtggaaat    3875
cattagtatg tgagggcctt gattgttatg taatattgcc aatgatgaat tcaggttgtt    3935
tttagcacaa gtttctcttt tttatgctgg tattctcact gccacatttt tggaaacctg    3995
tattacacct taaatctatc aataaatgat agttttctaa ttct                     4039
```

<210> SEQ ID NO 4
<211> LENGTH: 595
<212> TYPE: PRT
<213> ORGANISM: Homo sapien

<400> SEQUENCE: 4

```
Val Gly Ser Gly Ile Ser Phe Gln Pro Gly Ala Ile Gly Val Glu Val
 1               5                  10                  15

Ser Ala Met Asn Pro Val Asn Ala Thr Ala Leu Tyr Ile Ser Ala Ser
                20                  25                  30

Arg Leu Val Leu Asn Tyr Asp Pro Gly Asp Pro Lys Ala Phe Thr Glu
            35                  40                  45

Ile Asn Arg Leu Leu Pro Tyr Phe Arg Gln Ser Leu Ser Cys Cys Val
        50                  55                  60

Cys Gly His Leu Leu Gln Asp Pro Ile Ala Pro Thr Asn Ser Thr Cys
 65                  70                  75                  80

Gln His Tyr Val Cys Lys Thr Cys Lys Gly Lys Lys Met Met Met Lys
                85                  90                  95

Pro Ser Cys Ser Trp Cys Lys Asp Tyr Glu Gln Phe Glu Glu Asn Lys
               100                 105                 110

Gln Leu Ser Ile Leu Val Asn Cys Tyr Lys Lys Leu Cys Glu Tyr Ile
           115                 120                 125

Thr Gln Thr Thr Leu Ala Arg Asp Ile Ile Glu Ala Val Asp Cys Ser
       130                 135                 140

Ser Asp Ile Leu Ala Leu Leu Asn Asp Gly Ser Leu Phe Cys Glu Glu
145                 150                 155                 160

Thr Glu Lys Pro Ser Asp Ser Ser Phe Thr Leu Cys Leu Thr His Ser
               165                 170                 175

Pro Leu Pro Ser Thr Ser Glu Pro Thr Thr Asp Pro Gln Ala Ser Leu
           180                 185                 190

Ser Pro Met Ser Glu Ser Thr Leu Ser Ile Ala Ile Gly Ser Ser Val
       195                 200                 205

Ile Asn Gly Leu Pro Thr Tyr Asn Gly Leu Ser Ile Asp Arg Phe Gly
```

|     |     |     |     |     |     |     |     |     |     |     |     |
|-----|-----|-----|-----|-----|-----|-----|-----|-----|-----|-----|-----|
| 210 |     |     |     |     | 215 |     |     |     |     | 220 |     |
| Ile | Asn | Ile | Pro | Ser | Pro | Glu | His | Ser | Asn | Thr | Ile | Asp | Val | Cys | Asn |
| 225 |     |     |     |     | 230 |     |     |     |     | 235 |     |     |     |     | 240 |
| Thr | Val | Asp | Ile | Lys | Thr | Glu | Asp | Leu | Ser | Asp | Ser | Leu | Pro | Pro | Val |
|     |     |     |     | 245 |     |     |     |     | 250 |     |     |     |     | 255 |     |
| Cys | Asp | Thr | Val | Ala | Thr | Asp | Leu | Cys | Ser | Thr | Gly | Ile | Asp | Ile | Cys |
|     |     |     | 260 |     |     |     |     | 265 |     |     |     |     | 270 |     |     |
| Ser | Phe | Ser | Glu | Asp | Ile | Lys | Pro | Gly | Asp | Ser | Leu | Leu | Ser | Val |
|     |     | 275 |     |     |     |     | 280 |     |     |     |     | 285 |     |     |
| Glu | Glu | Val | Leu | Arg | Ser | Leu | Glu | Thr | Val | Ser | Asn | Thr | Glu | Val | Cys |
| 290 |     |     |     |     | 295 |     |     |     |     | 300 |     |     |     |     |     |
| Cys | Pro | Asn | Leu | Gln | Pro | Asn | Leu | Glu | Ala | Thr | Val | Ser | Asn | Gly | Pro |
| 305 |     |     |     | 310 |     |     |     |     | 315 |     |     |     |     | 320 |     |
| Phe | Leu | Gln | Leu | Ser | Ser | Gln | Ser | Leu | Ser | His | Asn | Val | Phe | Met | Ser |
|     |     |     |     | 325 |     |     |     |     | 330 |     |     |     |     | 335 |     |
| Thr | Ser | Pro | Ala | Leu | His | Gly | Leu | Ser | Cys | Thr | Ala | Ala | Thr | Pro | Lys |
|     |     |     | 340 |     |     |     |     | 345 |     |     |     |     | 350 |     |     |
| Ile | Ala | Lys | Leu | Asn | Arg | Lys | Arg | Ser | Arg | Ser | Glu | Ser | Asp | Ser | Glu |
|     |     | 355 |     |     |     |     | 360 |     |     |     |     | 365 |     |     |     |
| Lys | Val | Gln | Pro | Leu | Pro | Ile | Ser | Thr | Ile | Ile | Arg | Gly | Pro | Thr | Leu |
|     | 370 |     |     |     |     | 375 |     |     |     |     | 380 |     |     |     |     |
| Gly | Ala | Ser | Ala | Pro | Val | Thr | Val | Lys | Arg | Glu | Ser | Lys | Ile | Ser | Leu |
| 385 |     |     |     |     | 390 |     |     |     |     | 395 |     |     |     |     | 400 |
| Gln | Pro | Ile | Ala | Thr | Val | Pro | Asn | Gly | Gly | Thr | Thr | Pro | Lys | Ile | Ser |
|     |     |     |     | 405 |     |     |     |     | 410 |     |     |     |     | 415 |     |
| Lys | Thr | Val | Leu | Leu | Ser | Thr | Lys | Ser | Met | Lys | Lys | Ser | His | Glu | His |
|     |     |     |     | 420 |     |     |     |     | 425 |     |     |     |     | 430 |     |
| Gly | Ser | Lys | Lys | Ser | His | Ser | Lys | Thr | Lys | Pro | Gly | Ile | Leu | Lys | Lys |
|     |     |     | 435 |     |     |     |     | 440 |     |     |     |     | 445 |     |     |
| Asp | Lys | Ala | Val | Lys | Glu | Lys | Ile | Pro | Ser | His | His | Phe | Met | Pro | Gly |
|     |     | 450 |     |     |     |     | 455 |     |     |     |     | 460 |     |     |     |
| Ser | Pro | Thr | Lys | Thr | Val | Tyr | Lys | Lys | Pro | Gln | Glu | Lys | Lys | Gly | Cys |
| 465 |     |     |     |     | 470 |     |     |     |     | 475 |     |     |     |     | 480 |
| Lys | Cys | Gly | Arg | Ala | Thr | Gln | Asn | Pro | Ser | Val | Leu | Thr | Cys | Arg | Gly |
|     |     |     |     | 485 |     |     |     |     | 490 |     |     |     |     | 495 |     |
| Gln | Arg | Cys | Pro | Cys | Tyr | Ser | Asn | Arg | Lys | Ala | Cys | Leu | Asp | Cys | Ile |
|     |     |     |     | 500 |     |     |     |     | 505 |     |     |     |     | 510 |     |
| Cys | Arg | Gly | Cys | Gln | Asn | Ser | Tyr | Met | Ala | Asn | Gly | Glu | Lys | Lys | Leu |
|     |     |     |     | 515 |     |     |     |     | 520 |     |     |     |     | 525 |     |
| Glu | Ala | Phe | Ala | Val | Pro | Glu | Lys | Ala | Leu | Glu | Gln | Thr | Arg | Leu | Thr |
|     |     |     | 530 |     |     |     |     | 535 |     |     |     |     | 540 |     |     |
| Leu | Gly | Ile | Asn | Val | Thr | Ser | Ile | Ala | Val | Arg | Asn | Ala | Ser | Thr | Ser |
| 545 |     |     |     |     | 550 |     |     |     |     | 555 |     |     |     |     | 560 |
| Thr | Ser | Val | Ile | Asn | Val | Thr | Gly | Ser | Pro | Val | Thr | Thr | Phe | Leu | Ala |
|     |     |     |     | 565 |     |     |     |     | 570 |     |     |     |     | 575 |     |
| Ala | Ser | Thr | His | Asp | Asp | Lys | Ser | Leu | Asp | Glu | Ala | Ile | Asp | Met | Arg |
|     |     |     | 580 |     |     |     |     | 585 |     |     |     |     | 590 |     |     |
| Phe | Asp | Cys |
|     |     | 595 |

<210> SEQ ID NO 5
<211> LENGTH: 2611
<212> TYPE: DNA
<213> ORGANISM: Homo sapien

```
<220> FEATURE:
<221> NAME/KEY: CDS
<222> LOCATION: (21)...(473)

<400> SEQUENCE: 5
cttttttcac ctcgtctgaa atg gct gcc tcc cag tgt ctc tgc tgc tca aaa      53
                     Met Ala Ala Ser Gln Cys Leu Cys Cys Ser Lys
                      1               5                  10 ttt ctc ttc cag aga cag aac ctc gcc tgt ttc ctc aca aac cca cac       101
Phe Leu Phe Gln Arg Gln Asn Leu Ala Cys Phe Leu Thr Asn Pro His
             15                  20                  25 tgt ggc agc ctt gtt aat gca gat ggc cat ggt gaa gtg tgg aca gac       149
Cys Gly Ser Leu Val Asn Ala Asp Gly His Gly Glu Val Trp Thr Asp
         30                  35                  40 tgg aat aat atg tcc aag ttt ttc cag tat gga tgg cga tgc acc act       197
Trp Asn Asn Met Ser Lys Phe Phe Gln Tyr Gly Trp Arg Cys Thr Thr
     45                  50                  55 aat gag aat acc tat tca aac cgt acc ctg atg ggc aac tgg aac cag       245
Asn Glu Asn Thr Tyr Ser Asn Arg Thr Leu Met Gly Asn Trp Asn Gln
 60                  65                  70                  75 gaa aga tat gac ctg agg aat atc gtg cag ccc aaa ccc ttg cct tcc       293
Glu Arg Tyr Asp Leu Arg Asn Ile Val Gln Pro Lys Pro Leu Pro Ser
                 80                  85                  90 cag ttt gga cac tac ttt gaa aca aca tat gat aca agc tac aac aac       341
Gln Phe Gly His Tyr Phe Glu Thr Thr Tyr Asp Thr Ser Tyr Asn Asn
             95                 100                 105 aaa atg cca ctt tca aca cat aga ttt aag cga gag cct cac tgg ttc       389
Lys Met Pro Leu Ser Thr His Arg Phe Lys Arg Glu Pro His Trp Phe
        110                 115                 120 cca gga cat caa cct gaa ctg gat cct ccc cga tac aaa tgc aca gaa       437
Pro Gly His Gln Pro Glu Leu Asp Pro Pro Arg Tyr Lys Cys Thr Glu
    125                 130                 135 aag tca act tac atg aat agc tat tca aag cct taa attgggcatc            483
Lys Ser Thr Tyr Met Asn Ser Tyr Ser Lys Pro  *
140                 145                 150 actcaggatg tgtataagat cttaatattg atagtttcac atccaggttt ctaagaaatg     543
ataagatact tcacttttcc agagtgaaat gtaggaggga gcacattcta agtacagcta     603
aaaatttagc tcactgtaac acagtttcac tctctgaata aataaagcaa aaaacacagt     663
aaatattctt tatcccttttt tttgttgttg ttttaaccaa gatttaaatg tcaaatttaa    723
tacagcaact cagttctaca tttggggtgt tgtagaaggg ccttaaaaag aattatttta     783
ggccaggcac ggtggctcat gcctgtaatc ccagcacttt gggaggccga ggcaggtgga     843
tcacgtgagg tcaggagttc gagaccagcc tgaccaacat ggtgaaacac tgtctctact     903
aaaaacacaa aaattagctg agcatggtgg ctcacgcctg taatcccagc tactcaggag     963
gctgaggcag gggaatcgct tgaacctgag aagtggaggt tgtggtgagc tgagatcatg    1023
ccactgcact ttagcctggg tgacagagcg agactctgtc tcaaaaaaaa aaaaaaaaa     1083 agaattattt ctctgaagtc tacaaccact gtggtcttcc cttccttctg tcgtagcaag    1143
acctcagaat ctagcataac ttaggctagg tttggctaga tgctttctgg gtataagcca    1203
gagtcgtata gtgcaacttt gctgtgacct tagtgaacat cccctcttga ggactacaaa    1263
aacaaacgta acttttttaaa attattatgg agaattttac gtaaacaaa agtagacagg    1323 ctagtctaat gaactcccat gtatcattac ccagcatcaa ctatttatga ctaatcttac    1383
ctacttctac tttgtcttat tgaattaatt tggagcagaa tcttagaaat agaatttaat    1443
ctataaaaat cttggtgggc tgggtacggt ggctcatgcc tgtaatccca gcactttggg    1503
```

-continued

```
aggctgaggt gggtggatca cctgaggtca ggagtccaag accagcctgg ccaatgtggt      1563
gaaactccat ctcttctaaa aatacaaaaa ttagctggtc ttggtggcgg gcgcctgtaa      1623
tcccagctac ttgggaggct gaggcaggag aattgcttga acccaggaag cagaggttgc      1683
agtgagctga gacggtgcca ttgctctcca gcctgggcga caagagcgaa actccgtctc      1743
aaaaaaaaaa aagaaaagaa aaagaaaaaa aaaatcttgg tatactggct gggcacagtg      1803
gctcacacct aatcccagca ctttgggagg ctgaggcagg aggatagctt gaggctggga      1863
gttcaaaacc agcctgggca acatagcaag accccatctc taccaaaaaa aatttttta      1923 aagatttcag gtatatttct caaaagata aggactgtca attgtctact cccccccaac      1983
aaaggtcact aaggaaacct gttgactaaa caaagctcat taaacctatt gtagtgtagc     2043
aaaggagacc atcaacttga cacagagtct tggtaatgat tcaagggag gatgttagag      2103 taaggtatt ataaggattt gagataaggg tccaactggt ttaaaatgag tcaaaataagg     2163 gaactagtag agactgagaa agggttgtga atagcttagg tttggtaaac ttaggaaatc     2223
aacagtttta attttaatat ggttaaactg attagtattt cctatttttt tatctactgt     2283
gtaagaagac cctataatat atgggcatta ctgagagata ctgcccatat gttgtcctcg     2343
taagcaagga gatattttt atctcccata tattacctt caaaccttg ttactttagt      2403 ttcgagatat agatccagtt tatgttgtta ctcagtagtg aggaagtttc tttttttttt    2463
ttaaatggct atcaagttgt cccccatta gttattgaaa agaccataat tttttcactc     2523
ctattcaatg ccatttttat tgtaaataaa ctatgtacat gtaaaaaaaa aaaaaaaaaa    2583
aaaaaaaaaa aaaaaaaaa aaaaaaaa                                         2611
```

<210> SEQ ID NO 6
<211> LENGTH: 150
<212> TYPE: PRT
<213> ORGANISM: Homo sapien

<400> SEQUENCE: 6

```
Met Ala Ala Ser Gln Cys Leu Cys Cys Ser Lys Phe Leu Phe Gln Arg
 1               5                  10                  15

Gln Asn Leu Ala Cys Phe Leu Thr Asn Pro His Cys Gly Ser Leu Val
            20                  25                  30

Asn Ala Asp Gly His Gly Glu Val Trp Thr Asp Trp Asn Asn Met Ser
        35                  40                  45

Lys Phe Phe Gln Tyr Gly Trp Arg Cys Thr Thr Asn Glu Asn Thr Tyr
    50                  55                  60

Ser Asn Arg Thr Leu Met Gly Asn Trp Asn Gln Glu Arg Tyr Asp Leu
65                  70                  75                  80

Arg Asn Ile Val Gln Pro Lys Pro Leu Pro Ser Gln Phe Gly His Tyr
                85                  90                  95

Phe Glu Thr Thr Tyr Asp Thr Ser Tyr Asn Asn Lys Met Pro Leu Ser
            100                 105                 110

Thr His Arg Phe Lys Arg Glu Pro His Trp Phe Pro Gly His Gln Pro
        115                 120                 125

Glu Leu Asp Pro Pro Arg Tyr Lys Cys Thr Glu Lys Ser Thr Tyr Met
    130                 135                 140

Asn Ser Tyr Ser Lys Pro
145                 150
```

<210> SEQ ID NO 7

```
<211> LENGTH: 3296
<212> TYPE: DNA
<213> ORGANISM: Homo sapien
<220> FEATURE:
<221> NAME/KEY: CDS
<222> LOCATION: (65)...(1735)

<400> SEQUENCE: 7
cggaggaggc gaggagcgcc gggtaccggg ccgggggagc cgcgggctct cggggaagag         60 acgg atg atg aac aag ctt tac atc ggg aac ctg agc ccc gcc gtc acc        109
     Met Met Asn Lys Leu Tyr Ile Gly Asn Leu Ser Pro Ala Val Thr
       1               5                  10                  15 gcc gac gac ctc cgg cag ctc ttt ggg gac agg aag ctg ccc ctg gcg        157
Ala Asp Asp Leu Arg Gln Leu Phe Gly Asp Arg Lys Leu Pro Leu Ala
                 20                  25                  30 gga cag gtc ctg ctg aag tcc ggc tac gcc ttc gtg gac tac ccc gac        205
Gly Gln Val Leu Leu Lys Ser Gly Tyr Ala Phe Val Asp Tyr Pro Asp
             35                  40                  45 cag aac tgg gcc atc cgc gcc atc gag acc ctc tcg ggt aaa gtg gaa        253
Gln Asn Trp Ala Ile Arg Ala Ile Glu Thr Leu Ser Gly Lys Val Glu
         50                  55                  60 ttg cat ggg aaa atc atg gaa gtt gat tac tca gtc tct aaa aag cta        301
Leu His Gly Lys Ile Met Glu Val Asp Tyr Ser Val Ser Lys Lys Leu
 65                  70                  75 agg agc agg aaa att cag att cga aac atc cct cct cac ctg cag tgg        349
Arg Ser Arg Lys Ile Gln Ile Arg Asn Ile Pro Pro His Leu Gln Trp
 80                  85                  90                  95 gag gtg ttg gat gga ctt ttg gct caa tat ggg aca gtg gag aat gtg        397
Glu Val Leu Asp Gly Leu Leu Ala Gln Tyr Gly Thr Val Glu Asn Val
                100                 105                 110 gaa caa gtc aac aca gac aca gaa acc gcc gtt gtc aac gtc aca tat        445
Glu Gln Val Asn Thr Asp Thr Glu Thr Ala Val Val Asn Val Thr Tyr
            115                 120                 125 gca aca aga gaa gaa gca aaa ata gcc atg gag aag cta agc ggg cat        493
Ala Thr Arg Glu Glu Ala Lys Ile Ala Met Glu Lys Leu Ser Gly His
        130                 135                 140 cag ttt gag aac tac tcc ttc aag att tcc tac atc ccg gat gaa gag        541
Gln Phe Glu Asn Tyr Ser Phe Lys Ile Ser Tyr Ile Pro Asp Glu Glu
145                 150                 155 gtg agc tcc cct tcg ccc cct cag cga gcc cag cgt ggg gac cac tct        589
Val Ser Ser Pro Ser Pro Pro Gln Arg Ala Gln Arg Gly Asp His Ser
160                 165                 170                 175 tcc cgg gag caa ggc cac gcc cct ggg ggc act tct cag gcc aga cag        637
Ser Arg Glu Gln Gly His Ala Pro Gly Gly Thr Ser Gln Ala Arg Gln
                180                 185                 190 att gat ttc ccg ctg cgg atc ctg gtc ccc acc cag ttt gtt ggt gcc        685
Ile Asp Phe Pro Leu Arg Ile Leu Val Pro Thr Gln Phe Val Gly Ala
            195                 200                 205 atc atc gga aag gag ggc ttg acc ata aag aac atc act aag cag acc        733
Ile Ile Gly Lys Glu Gly Leu Thr Ile Lys Asn Ile Thr Lys Gln Thr
        210                 215                 220 cag tcc cgg gta gat atc cat aga aaa gag aac tct gga gct gca gag        781
Gln Ser Arg Val Asp Ile His Arg Lys Glu Asn Ser Gly Ala Ala Glu
225                 230                 235 aag cct gtc acc atc cat gcc acc cca gag ggg act tct gaa gca tgc        829
Lys Pro Val Thr Ile His Ala Thr Pro Glu Gly Thr Ser Glu Ala Cys
240                 245                 250                 255 cgc atg att ctt gaa atc atg cag aaa gag gca gat gag acc aaa cta        877
Arg Met Ile Leu Glu Ile Met Gln Lys Glu Ala Asp Glu Thr Lys Leu
                260                 265                 270
```

-continued

| | | |
|---|---|---|
| gcc gaa gag att cct ctg aaa atc ttg gca cac aat ggc ttg gtt gga<br>Ala Glu Glu Ile Pro Leu Lys Ile Leu Ala His Asn Gly Leu Val Gly<br>275 280 285 | | 925 |
| aga ctg att gga aaa gaa ggc aga aat ttg aag aaa att gaa cat gaa<br>Arg Leu Ile Gly Lys Glu Gly Arg Asn Leu Lys Lys Ile Glu His Glu<br>290 295 300 | | 973 |
| aca ggg acc aag ata aca atc tca tct ttg cag gat ttg agc ata tac<br>Thr Gly Thr Lys Ile Thr Ile Ser Ser Leu Gln Asp Leu Ser Ile Tyr<br>305 310 315 | | 1021 |
| aac ccg gaa aga acc atc act gtg aag ggc aca gtt gag gcc tgt gcc<br>Asn Pro Glu Arg Thr Ile Thr Val Lys Gly Thr Val Glu Ala Cys Ala<br>320 325 330 335 | | 1069 |
| agt gct gag ata gag att atg aag aag ctg cgt gag gcc ttt gaa aat<br>Ser Ala Glu Ile Glu Ile Met Lys Lys Leu Arg Glu Ala Phe Glu Asn<br>340 345 350 | | 1117 |
| gat atg ctg gct gtt aac acc cac tcc gga tac ttc tcc agc ctg tac<br>Asp Met Leu Ala Val Asn Thr His Ser Gly Tyr Phe Ser Ser Leu Tyr<br>355 360 365 | | 1165 |
| ccc cat cac cag ttt ggc ccg ttc ccg cat cat cac tct tat cca gag<br>Pro His His Gln Phe Gly Pro Phe Pro His His His Ser Tyr Pro Glu<br>370 375 380 | | 1213 |
| cag gag att gtg aat ctc ttc atc cca acc cag gct gtg ggc gcc atc<br>Gln Glu Ile Val Asn Leu Phe Ile Pro Thr Gln Ala Val Gly Ala Ile<br>385 390 395 | | 1261 |
| atc ggg aag aag ggg gca cac atc aaa cag ctg gcg aga ttc gcc gga<br>Ile Gly Lys Lys Gly Ala His Ile Lys Gln Leu Ala Arg Phe Ala Gly<br>400 405 410 415 | | 1309 |
| gcc tct atc aag att gcc cct gcg gaa ggc cca gac gtc agc gaa agg<br>Ala Ser Ile Lys Ile Ala Pro Ala Glu Gly Pro Asp Val Ser Glu Arg<br>420 425 430 | | 1357 |
| atg gtc atc atc acc ggg cca ccg gaa gcc cag ttc aag gcc cag gga<br>Met Val Ile Ile Thr Gly Pro Pro Glu Ala Gln Phe Lys Ala Gln Gly<br>435 440 445 | | 1405 |
| cgg atc ttt ggg aaa ctg aaa gag gaa aac ttc ttt aac ccc aaa gaa<br>Arg Ile Phe Gly Lys Leu Lys Glu Glu Asn Phe Phe Asn Pro Lys Glu<br>450 455 460 | | 1453 |
| gaa gtg aag ctg gaa gcg cat atc aga gtg ccc tct tcc aca gct ggc<br>Glu Val Lys Leu Glu Ala His Ile Arg Val Pro Ser Ser Thr Ala Gly<br>465 470 475 | | 1501 |
| cgg gtg att ggc aaa ggt ggc aag acc gtg aac gaa ctg cag aac tta<br>Arg Val Ile Gly Lys Gly Gly Lys Thr Val Asn Glu Leu Gln Asn Leu<br>480 485 490 495 | | 1549 |
| acc agt gca gaa gtc atc gtg cct cgt gac caa acg cca gat gaa aat<br>Thr Ser Ala Glu Val Ile Val Pro Arg Asp Gln Thr Pro Asp Glu Asn<br>500 505 510 | | 1597 |
| gag gaa gtg atc gtc aga att atc ggg cac ttc ttt gct agc cag act<br>Glu Glu Val Ile Val Arg Ile Ile Gly His Phe Phe Ala Ser Gln Thr<br>515 520 525 | | 1645 |
| gca cag cgc aag atc agg gaa att gta caa cag gtg aag cag cag gag<br>Ala Gln Arg Lys Ile Arg Glu Ile Val Gln Gln Val Lys Gln Gln Glu<br>530 535 540 | | 1693 |
| cag aaa tac cct cag gga gtc gcc tca cag cgc agc aag tga<br>Gln Lys Tyr Pro Gln Gly Val Ala Ser Gln Arg Ser Lys *<br>545 550 555 | | 1735 |
| ggctcccaca ggcaccagca aaacaacgga tgaatgtagc ccttccaaca cctgacagaa | | 1795 |
| tgagaccaaa cgcagccagc cagatcggga gcaaaccaaa gaccatctga ggaatgagaa | | 1855 |
| gtctgcggag gcggcagggg actctgccga ggccctgaga accccagggg ccgaggaggg | | 1915 |
| gcggggaagg tcagccaggt tgccagaaac caccgagccc cgcctcccgc cccccagggc | | 1975 |

```
ttctgcaggc ttcagccatc cacttcacca tccactcgga tctctcctga actcccacga    2035
cgctatccct tttagttgaa ctaacatagg tgaacgtgtt caaagccaag caaaatgcac    2095 acccttttc tgtggcaaat cgtctctgta catgtgtgta catattagaa agggaagatg     2155
ttaagatatg tggcctgtgg gttacacagg gtgcctgcag cggtaatata ttttagaaat    2215
aatatatcaa ataactcaac taactccaat ttttaatcaa ttattaattt ttttttcttt    2275
ttaaagagaa agcaggcttt tctagacttt aaagaataaa gtctttggga ggtctcacgg    2335
tgtagagagg agctttgagg ccacccgcac aaaattcacc cagagggaaa tctcgtcgga    2395
aggacactca cggcagttct ggatcacctg tgtatgtcaa cagaagggat accgtctcct    2455
tgaagaggaa actctgtcac tcctcatgcc tgtctagctc atacacccat ttctctttgc    2515
ttcacaggtt ttaaactggt tttttgcata ctgctatata attctctgtc tctctctgtt    2575
tatctctccc ctccctcccc tccccttctt ctccatctcc attctttttga atttcctcat   2635 ccctccatct caatcccgta tctacgcacc ccccccccc aggcaaagca gtgctctgag     2695
tatcacatca cacaaaagga acaaaagcga acacacaaa ccagcctcaa cttacacttg     2755
gttactcaaa agaacaagag tcaatggtac ttgtcctagc gttttggaag aggaaaacag    2815
gaacccacca aaccaaccaa tcaaccaaac aaagaaaaaa ttccacaatg aaagaatgta    2875
ttttgtcttt ttgcattttg gtgtataagc catcaatatt cagcaaaatg attccttct    2935 ttaaaaaaaa aaaatgtgga ggaaagtaga aatttaccaa ggttgttggc ccagggcgtt    2995
aaattcacag attttttttaa cgagaaaaac acacagaaga agctacctca ggtgttttta   3055
cctcagcacc ttgatcttgt gtttccctta gagattttgt aaagctgata gttggagcat    3115 tttttttattt ttttaataaa aatgagttgg aaaaaaaata agatatcaac tgccagcctg   3175
gagaaggtga cagtccaagt gtgcaacagc tgttctgaat tgtcttccgc tagccaagaa    3235
cctatatggc cttcttttgg acaaaccttg aaaatgttta tttaaaaaaa aaaaaaaaaa    3295
a                                                                   3296
```

<210> SEQ ID NO 8
<211> LENGTH: 556
<212> TYPE: PRT
<213> ORGANISM: Homo sapien

<400> SEQUENCE: 8

```
Met Met Asn Lys Leu Tyr Ile Gly Asn Leu Ser Pro Ala Val Thr Ala
 1               5                  10                  15

Asp Asp Leu Arg Gln Leu Phe Gly Asp Arg Lys Leu Pro Leu Ala Gly
             20                  25                  30

Gln Val Leu Leu Lys Ser Gly Tyr Ala Phe Val Asp Tyr Pro Asp Gln
         35                  40                  45

Asn Trp Ala Ile Arg Ala Ile Glu Thr Leu Ser Gly Lys Val Glu Leu
     50                  55                  60

His Gly Lys Ile Met Glu Val Asp Tyr Ser Val Ser Lys Lys Leu Arg
 65                  70                  75                  80

Ser Arg Lys Ile Gln Ile Arg Asn Ile Pro Pro His Leu Gln Trp Glu
                 85                  90                  95

Val Leu Asp Gly Leu Leu Ala Gln Tyr Gly Thr Val Glu Asn Val Glu
            100                 105                 110

Gln Val Asn Thr Asp Thr Glu Thr Ala Val Val Asn Val Thr Tyr Ala
        115                 120                 125
```

```
Thr Arg Glu Glu Ala Lys Ile Ala Met Glu Lys Leu Ser Gly His Gln
    130                 135                 140

Phe Glu Asn Tyr Ser Phe Lys Ile Ser Tyr Ile Pro Asp Glu Glu Val
145                 150                 155                 160

Ser Ser Pro Ser Pro Pro Gln Arg Ala Gln Arg Gly Asp His Ser Ser
                165                 170                 175

Arg Glu Gln Gly His Ala Pro Gly Gly Thr Ser Gln Ala Arg Gln Ile
                180                 185                 190

Asp Phe Pro Leu Arg Ile Leu Val Pro Thr Gln Phe Val Gly Ala Ile
            195                 200                 205

Ile Gly Lys Glu Gly Leu Thr Ile Lys Asn Ile Thr Lys Gln Thr Gln
    210                 215                 220

Ser Arg Val Asp Ile His Arg Lys Glu Asn Ser Gly Ala Ala Glu Lys
225                 230                 235                 240

Pro Val Thr Ile His Ala Thr Pro Glu Gly Thr Ser Glu Ala Cys Arg
                245                 250                 255

Met Ile Leu Glu Ile Met Gln Lys Glu Ala Asp Glu Thr Lys Leu Ala
                260                 265                 270

Glu Glu Ile Pro Leu Lys Ile Leu Ala His Asn Gly Leu Val Gly Arg
            275                 280                 285

Leu Ile Gly Lys Glu Gly Arg Asn Leu Lys Lys Ile Glu His Glu Thr
    290                 295                 300

Gly Thr Lys Ile Thr Ile Ser Ser Leu Gln Asp Leu Ser Ile Tyr Asn
305                 310                 315                 320

Pro Glu Arg Thr Ile Thr Val Lys Gly Thr Val Glu Ala Cys Ala Ser
                325                 330                 335

Ala Glu Ile Glu Ile Met Lys Lys Leu Arg Glu Ala Phe Glu Asn Asp
                340                 345                 350

Met Leu Ala Val Asn Thr His Ser Gly Tyr Phe Ser Ser Leu Tyr Pro
            355                 360                 365

His His Gln Phe Gly Pro Phe Pro His His His Ser Tyr Pro Glu Gln
    370                 375                 380

Glu Ile Val Asn Leu Phe Ile Pro Thr Gln Ala Val Gly Ala Ile Ile
385                 390                 395                 400

Gly Lys Lys Gly Ala His Ile Lys Gln Leu Ala Arg Phe Ala Gly Ala
                405                 410                 415

Ser Ile Lys Ile Ala Pro Ala Glu Gly Pro Asp Val Ser Glu Arg Met
                420                 425                 430

Val Ile Ile Thr Gly Pro Pro Glu Ala Gln Phe Lys Ala Gln Gly Arg
            435                 440                 445

Ile Phe Gly Lys Leu Lys Glu Glu Asn Phe Phe Asn Pro Lys Glu Glu
    450                 455                 460

Val Lys Leu Glu Ala His Ile Arg Val Pro Ser Ser Thr Ala Gly Arg
465                 470                 475                 480

Val Ile Gly Lys Gly Gly Lys Thr Val Asn Glu Leu Gln Asn Leu Thr
                485                 490                 495

Ser Ala Glu Val Ile Val Pro Arg Asp Gln Thr Pro Asp Glu Asn Glu
                500                 505                 510

Glu Val Ile Val Arg Ile Gly His Phe Phe Ala Ser Gln Thr Ala
            515                 520                 525

Gln Arg Lys Ile Arg Glu Ile Val Gln Val Lys Gln Gln Glu Gln
    530                 535                 540

Lys Tyr Pro Gln Gly Val Ala Ser Gln Arg Ser Lys
```

<210> SEQ ID NO 9
<211> LENGTH: 3164
<212> TYPE: DNA
<213> ORGANISM: Homo sapien
<220> FEATURE:
<221> NAME/KEY: CDS
<222> LOCATION: (65)...(1603)

<400> SEQUENCE: 9

| | | |
|---|---|---|
| cggaggaggc gaggagcgcc gggtaccggg ccgggggagc cgcgggctct cggggaagag | | 60 |
| acgg atg atg aac aag ctt tac atc ggg aac ctg agc ccc gcc gtc acc<br>     Met Met Asn Lys Leu Tyr Ile Gly Asn Leu Ser Pro Ala Val Thr<br>     1               5                   10               15 | | 109 |
| gcc gac gac ctc cgg cag ctc ttt ggg gac agg aag ctg ccc ctg gcg<br>Ala Asp Asp Leu Arg Gln Leu Phe Gly Asp Arg Lys Leu Pro Leu Ala<br>               20                   25                30 | | 157 |
| gga cag gtc ctg ctg aag tcc ggc tac gcc ttc gtg gac tac ccc gac<br>Gly Gln Val Leu Leu Lys Ser Gly Tyr Ala Phe Val Asp Tyr Pro Asp<br> 35                    40                 45 | | 205 |
| cag aac tgg gcc atc cgc gcc atc gag acc ctc tcg ggt aaa gtg gaa<br>Gln Asn Trp Ala Ile Arg Ala Ile Glu Thr Leu Ser Gly Lys Val Glu<br>    50                   55                60 | | 253 |
| ttg cat ggg aaa atc atg gaa gtt gat tac tca gtc tct aaa aag cta<br>Leu His Gly Lys Ile Met Glu Val Asp Tyr Ser Val Ser Lys Lys Leu<br>65                 70                75 | | 301 |
| agg agc agg aaa att cag att cga aac atc cct cct cac ctg cag tgg<br>Arg Ser Arg Lys Ile Gln Ile Arg Asn Ile Pro Pro His Leu Gln Trp<br>   80                 85                90               95 | | 349 |
| gag gtg ttg gat gga ctt ttg gct caa tat ggg aca gtg gag aat gtg<br>Glu Val Leu Asp Gly Leu Leu Ala Gln Tyr Gly Thr Val Glu Asn Val<br>               100                  105               110 | | 397 |
| gaa caa gtc aac aca gac aca gaa acc gcc gtt gtc aac gtc aca tat<br>Glu Gln Val Asn Thr Asp Thr Glu Thr Ala Val Val Asn Val Thr Tyr<br>            115                  120               125 | | 445 |
| gca aca aga gaa gaa gca aaa ata gcc atg gag aag cta agc ggg cat<br>Ala Thr Arg Glu Glu Ala Lys Ile Ala Met Glu Lys Leu Ser Gly His<br>        130                  135               140 | | 493 |
| cag ttt gag aac tac tcc ttc aag att tcc tac atc ccg gat gaa gag<br>Gln Phe Glu Asn Tyr Ser Phe Lys Ile Ser Tyr Ile Pro Asp Glu Glu<br>145                150                155 | | 541 |
| ttt gtt ggt gcc atc atc gga aag gag ggc ttg acc ata aag aac atc<br>Phe Val Gly Ala Ile Ile Gly Lys Glu Gly Leu Thr Ile Lys Asn Ile<br>160                 165              170               175 | | 589 |
| act aag cag acc cag tcc cgg gta gat atc cat aga aaa gag aac tct<br>Thr Lys Gln Thr Gln Ser Arg Val Asp Ile His Arg Lys Glu Asn Ser<br>              180                  185               190 | | 637 |
| gga gct gca gag aag cct gtc acc atc cat gcc acc cca gag ggg act<br>Gly Ala Ala Glu Lys Pro Val Thr Ile His Ala Thr Pro Glu Gly Thr<br>         195                  200               205 | | 685 |
| tct gaa gca tgc cgc atg att ctt gaa atc atg cag aaa gag gca gat<br>Ser Glu Ala Cys Arg Met Ile Leu Glu Ile Met Gln Lys Glu Ala Asp<br>        210                  215               220 | | 733 |
| gag acc aaa cta gcc gaa gag att cct ctg aaa atc ttg gca cac aat<br>Glu Thr Lys Leu Ala Glu Glu Ile Pro Leu Lys Ile Leu Ala His Asn<br>225                230                235 | | 781 |
| ggc ttg gtt gga aga ctg att gga aaa gaa ggc aga aat ttg aag aaa<br>Gly Leu Val Gly Arg Leu Ile Gly Lys Glu Gly Arg Asn Leu Lys Lys<br>240                 245              250               255 | | 829 |

-continued

| | |
|---|---|
| att gaa cat gaa aca ggg acc aag ata aca atc tca tct ttg cag gat<br>Ile Glu His Glu Thr Gly Thr Lys Ile Thr Ile Ser Ser Leu Gln Asp<br>260 265 270 | 877 |
| ttg agc ata tac aac ccg gaa aga acc atc act gtg aag ggc aca gtt<br>Leu Ser Ile Tyr Asn Pro Glu Arg Thr Ile Thr Val Lys Gly Thr Val<br>275 280 285 | 925 |
| gag gcc tgt gcc agt gct gag ata gag att atg aag aag ctg cgt gag<br>Glu Ala Cys Ala Ser Ala Glu Ile Glu Ile Met Lys Lys Leu Arg Glu<br>290 295 300 | 973 |
| gcc ttt gaa aat gat atg ctg gct gtt aac acc cac tcc gga tac ttc<br>Ala Phe Glu Asn Asp Met Leu Ala Val Asn Thr His Ser Gly Tyr Phe<br>305 310 315 | 1021 |
| tcc agc ctg tac ccc cat cac cag ttt ggc ccg ttc ccg cat cat cac<br>Ser Ser Leu Tyr Pro His His Gln Phe Gly Pro Phe Pro His His His<br>320 325 330 335 | 1069 |
| tct tat cca gag cag gag att gtg aat ctc ttc atc cca acc cag gct<br>Ser Tyr Pro Glu Gln Glu Ile Val Asn Leu Phe Ile Pro Thr Gln Ala<br>340 345 350 | 1117 |
| gtg ggc gcc atc atc ggg aag aag ggg gca cac atc aaa cag ctg gcg<br>Val Gly Ala Ile Ile Gly Lys Lys Gly Ala His Ile Lys Gln Leu Ala<br>355 360 365 | 1165 |
| aga ttc gcc gga gcc tct atc aag att gcc cct gcg gaa ggc cca gac<br>Arg Phe Ala Gly Ala Ser Ile Lys Ile Ala Pro Ala Glu Gly Pro Asp<br>370 375 380 | 1213 |
| gtc agc gaa agg atg gtc atc atc acc ggg cca ccg gaa gcc cag ttc<br>Val Ser Glu Arg Met Val Ile Ile Thr Gly Pro Pro Glu Ala Gln Phe<br>385 390 395 | 1261 |
| aag gcc cag gga cgg atc ttt ggg aaa ctg aaa gag gaa aac ttc ttt<br>Lys Ala Gln Gly Arg Ile Phe Gly Lys Leu Lys Glu Glu Asn Phe Phe<br>400 405 410 415 | 1309 |
| aac ccc aaa gaa gaa gtg aag ctg gaa gcg cat atc aga gtg ccc tct<br>Asn Pro Lys Glu Glu Val Lys Leu Glu Ala His Ile Arg Val Pro Ser<br>420 425 430 | 1357 |
| tcc aca gct ggc cgg gtg att ggc aaa ggt ggc aag acc gtg aac gaa<br>Ser Thr Ala Gly Arg Val Ile Gly Lys Gly Gly Lys Thr Val Asn Glu<br>435 440 445 | 1405 |
| ctg cag aac tta acc agt gca gaa gtc atc gtg cct cgt gac caa acg<br>Leu Gln Asn Leu Thr Ser Ala Glu Val Ile Val Pro Arg Asp Gln Thr<br>450 455 460 | 1453 |
| cca gat gaa aat gag gaa gtg atc gtc aga att atc ggg cac ttc ttt<br>Pro Asp Glu Asn Glu Glu Val Ile Val Arg Ile Ile Gly His Phe Phe<br>465 470 475 | 1501 |
| gct agc cag act gca cag cgc aag atc agg gaa att gta caa cag gtg<br>Ala Ser Gln Thr Ala Gln Arg Lys Ile Arg Glu Ile Val Gln Gln Val<br>480 485 490 495 | 1549 |
| aag cag cag gag cag aaa tac cct cag gga gtc gcc tca cag cgc agc<br>Lys Gln Gln Glu Gln Lys Tyr Pro Gln Gly Val Ala Ser Gln Arg Ser<br>500 505 510 | 1597 |
| aag tga ggctcccaca ggcaccagca aaacaacgga tgaatgtagc ccttccaaca<br>Lys * | 1653 |
| cctgacagaa tgagaccaaa cgcagccagc cagatcggga gcaaaccaaa gaccatctga | 1713 |
| ggaatgagaa gtctgcggag gcggccaggg actctgccga ggccctgaga accccagggg | 1773 |
| ccgaggaggg gcggggaagg tcagccaggt tgccagaac caccgagccc cgcctcccgc | 1833 |
| cccccagggc ttctgcaggc ttcagccatc cacttcacca tccactcgga tctctcctga | 1893 |
| actcccacga cgctatccct tttagttgaa ctaacatagg tgaacgtgtt caaagccaag | 1953 |
| caaaatgcac acccttttc tgtggcaaat cgtctctgta catgtgtgta catattagaa | 2013 |

```
agggaagatg ttaagatatg tggcctgtgg gttacacagg gtgcctgcag cggtaatata    2073
ttttagaaat aatatatcaa ataactcaac taactccaat ttttaatcaa ttattaattt    2133
ttttttcttt ttaaagagaa agcaggcttt tctagacttt aaagaataaa gtctttggga    2193
ggtctcacgg tgtagagagg agcttgagg ccacccgcac aaaattcacc cagagggaaa     2253
tctcgtcgga aggacactca cggcagttct ggatcacctg tgtatgtcaa cagaagggat    2313
accgtctcct tgaagaggaa actctgtcac tcctcatgcc tgtctagctc atacacccat    2373 ttctcttttgc ttcacaggtt ttaaactggt ttttttgcata ctgctatata attctctgtc  2433
tctctctgtt tatctctccc ctccctcccc tccccttctt ctccatctcc attcttttga    2493
atttcctcat ccctccatct caatcccgta tctacgcacc ccccccccc aggcaaagca     2553 gtgctctgag tatcacatca cacaaaagga acaaaagcga aacacacaaa ccagcctcaa    2613
cttacacttg gttactcaaa agaacaagag tcaatggtac ttgtcctagc gttttggaag    2673
aggaaaacag gaacccacca aaccaaccaa tcaaccaaac aaagaaaaaa ttccacaatg    2733
aaagaatgta ttttgtcttt ttgcatttg gtgtataagc catcaatatt cagcaaaatg     2793
attcctttct ttaaaaaaaa aaaatgtgga ggaaagtaga aattaccaa ggttgttggc     2853 ccagggcgtt aaattcacag atttttttaa cgagaaaaac acacagaaga agctacctca   2913
ggtgttttta cctcagcacc ttgatcttgt gtttccctta gagattttgt aaagctgata   2973
gttggagcat tttttttattt ttttaataaa aatgagttgg aaaaaaaata agatatcaac  3033
tgccagcctg gagaaggtga cagtccaagt gtgcaacagc tgttctgaat tgtcttccgc   3093
tagccaagaa cctatatggc cttcttttgg acaaaccttg aaaatgttta tttaaaaaaa   3153 aaaaaaaaa a                                                         3164
```

<210> SEQ ID NO 10
<211> LENGTH: 512
<212> TYPE: PRT
<213> ORGANISM: Homo sapien

<400> SEQUENCE: 10

```
Met Met Asn Lys Leu Tyr Ile Gly Asn Leu Ser Pro Ala Val Thr Ala
  1               5                  10                  15

Asp Asp Leu Arg Gln Leu Phe Gly Asp Arg Lys Leu Pro Leu Ala Gly
             20                  25                  30

Gln Val Leu Leu Lys Ser Gly Tyr Ala Phe Val Asp Tyr Pro Asp Gln
         35                  40                  45

Asn Trp Ala Ile Arg Ala Ile Glu Thr Leu Ser Gly Lys Val Glu Leu
     50                  55                  60

His Gly Lys Ile Met Glu Val Asp Tyr Ser Val Ser Lys Leu Arg
 65                  70                  75                  80

Ser Arg Lys Ile Gln Ile Arg Asn Ile Pro Pro His Leu Gln Trp Glu
                 85                  90                  95

Val Leu Asp Gly Leu Leu Ala Gln Tyr Gly Thr Val Glu Asn Val Glu
            100                 105                 110

Gln Val Asn Thr Asp Thr Glu Thr Ala Val Val Asn Val Thr Tyr Ala
        115                 120                 125

Thr Arg Glu Glu Ala Lys Ile Ala Met Glu Lys Leu Ser Gly His Gln
    130                 135                 140

Phe Glu Asn Tyr Ser Phe Lys Ile Ser Tyr Ile Pro Asp Glu Glu Phe
145                 150                 155                 160

Val Gly Ala Ile Ile Gly Lys Glu Gly Leu Thr Ile Lys Asn Ile Thr
```

|  |  |  |  |  | 165 |  |  |  | 170 |  |  |  | 175 |  |
|---|---|---|---|---|---|---|---|---|---|---|---|---|---|---|
| Lys | Gln | Thr | Gln | Ser | Arg | Val | Asp | Ile | His | Arg | Lys | Glu | Asn | Ser | Gly |
|  |  |  | 180 |  |  |  |  | 185 |  |  |  |  | 190 |  |  |

Ala Ala Glu Lys Pro Val Thr Ile His Ala Thr Pro Glu Gly Thr Ser
        195                 200                 205

Glu Ala Cys Arg Met Ile Leu Glu Ile Met Gln Lys Glu Ala Asp Glu
        210                 215                 220

Thr Lys Leu Ala Glu Glu Ile Pro Leu Lys Ile Leu Ala His Asn Gly
225                 230                 235                 240

Leu Val Gly Arg Leu Ile Gly Lys Glu Gly Arg Asn Leu Lys Lys Ile
                245                 250                 255

Glu His Glu Thr Gly Thr Lys Ile Thr Ile Ser Ser Leu Gln Asp Leu
                260                 265                 270

Ser Ile Tyr Asn Pro Glu Arg Thr Ile Thr Val Lys Gly Thr Val Glu
                275                 280                 285

Ala Cys Ala Ser Ala Glu Ile Glu Ile Met Lys Lys Leu Arg Glu Ala
                290                 295                 300

Phe Glu Asn Asp Met Leu Ala Val Asn Thr His Ser Gly Tyr Phe Ser
305                 310                 315                 320

Ser Leu Tyr Pro His His Gln Phe Gly Pro Phe Pro His His His Ser
                325                 330                 335

Tyr Pro Glu Gln Glu Ile Val Asn Leu Phe Ile Pro Thr Gln Ala Val
                340                 345                 350

Gly Ala Ile Ile Gly Lys Lys Gly Ala His Ile Lys Gln Leu Ala Arg
                355                 360                 365

Phe Ala Gly Ala Ser Ile Lys Ile Ala Pro Ala Glu Gly Pro Asp Val
                370                 375                 380

Ser Glu Arg Met Val Ile Ile Thr Gly Pro Pro Glu Ala Gln Phe Lys
385                 390                 395                 400

Ala Gln Gly Arg Ile Phe Gly Lys Leu Lys Glu Glu Asn Phe Phe Asn
                405                 410                 415

Pro Lys Glu Glu Val Lys Leu Glu Ala His Ile Arg Val Pro Ser Ser
                420                 425                 430

Thr Ala Gly Arg Val Ile Gly Lys Gly Gly Lys Thr Val Asn Glu Leu
                435                 440                 445

Gln Asn Leu Thr Ser Ala Glu Val Ile Val Pro Arg Asp Gln Thr Pro
450                 455                 460

Asp Glu Asn Glu Glu Val Ile Val Arg Ile Ile Gly His Phe Phe Ala
465                 470                 475                 480

Ser Gln Thr Ala Gln Arg Lys Ile Arg Glu Ile Val Gln Gln Val Lys
                485                 490                 495

Gln Gln Glu Gln Lys Tyr Pro Gln Gly Val Ala Ser Gln Arg Ser Lys
                500                 505                 510

<210> SEQ ID NO 11
<211> LENGTH: 1580
<212> TYPE: DNA
<213> ORGANISM: Homo sapien
<220> FEATURE:
<221> NAME/KEY: CDS
<222> LOCATION: (220)...(1050)

<400> SEQUENCE: 11
catcctgcca cccctagcct tgctggggac gtgaaccctc tccccgcgcc tgggaagcct    60
tcttggcacc gggacccgga gaatccccac ggaagccagt tccaaaaggg atgaaaaggg   120

```
ggcgtttcgg gcactgggag aagcctgtat tccagggccc ctcccagagc aggaatctgg      180
gacccaggag tgccagcctc acccacgcag atcctggcc atg aga gct ccg cac         234
                                           Met Arg Ala Pro His
                                             1               5 ctc cac ctc tcc gcc gcc tct ggc gcc cgg gct ctg gcg aag ctg ctg        282
Leu His Leu Ser Ala Ala Ser Gly Ala Arg Ala Leu Ala Lys Leu Leu
                10                  15                  20 ccg ctg ctg atg gcg caa ctc tgg gcc gca gag gcg gcg ctg ctc ccc        330
Pro Leu Leu Met Ala Gln Leu Trp Ala Ala Glu Ala Ala Leu Leu Pro
            25                  30                  35 caa aac gac acg cgc ttg gac ccc gaa gcc tat ggc tcc ccg tgc gcg        378
Gln Asn Asp Thr Arg Leu Asp Pro Glu Ala Tyr Gly Ser Pro Cys Ala
        40                  45                  50 cgc ggc tcg cag ccc tgg cag gtc tcg ctc ttc aac ggc ctc tcg ttc        426
Arg Gly Ser Gln Pro Trp Gln Val Ser Leu Phe Asn Gly Leu Ser Phe
    55                  60                  65 cac tgc gcg ggt gtc ctg gtg gac cag agt tgg gtg ctg acg gcc gcg        474
His Cys Ala Gly Val Leu Val Asp Gln Ser Trp Val Leu Thr Ala Ala
70                  75                  80                  85 cac tgc gga aac aag cca ctg tgg gct cga gta ggg gat gac cac ctg        522
His Cys Gly Asn Lys Pro Leu Trp Ala Arg Val Gly Asp Asp His Leu
                90                  95                 100 ctt ctt ctt cag gga gag cag ctc cgc cgg acc act cgc tct gtt gtc        570
Leu Leu Leu Gln Gly Glu Gln Leu Arg Arg Thr Thr Arg Ser Val Val
            105                 110                 115 cat ccc aag tac cac cag ggc tca ggc ccc atc ctg cca agg cga acg        618
His Pro Lys Tyr His Gln Gly Ser Gly Pro Ile Leu Pro Arg Arg Thr
        120                 125                 130 gat gag cac gat ctc atg ttg ctg aag ctg gcc agg ccc gta gtg ctg        666
Asp Glu His Asp Leu Met Leu Leu Lys Leu Ala Arg Pro Val Val Leu
    135                 140                 145 ggg ccc cgc gtc cgg gcc ctg cag ctt ccc tac cgc tgt gct cag ccc        714
Gly Pro Arg Val Arg Ala Leu Gln Leu Pro Tyr Arg Cys Ala Gln Pro
150                 155                 160                 165 gga gac cag tgc cag gtt gct ggc tgg ggc acc acg gcc gcc cgg aga        762
Gly Asp Gln Cys Gln Val Ala Gly Trp Gly Thr Thr Ala Ala Arg Arg
                170                 175                 180 gtg aag tac aac aag ggc ctg acc tgc tcc agc atc act atc ctg agc        810
Val Lys Tyr Asn Lys Gly Leu Thr Cys Ser Ser Ile Thr Ile Leu Ser
            185                 190                 195 cct aaa gag tgt gag gtc ttc tac cct ggc gtg gtc acc aac aac atg        858
Pro Lys Glu Cys Glu Val Phe Tyr Pro Gly Val Val Thr Asn Asn Met
        200                 205                 210 ata tgt gct gga ctg gac cgg ggc cag gac cct tgc cag agt gac tct        906
Ile Cys Ala Gly Leu Asp Arg Gly Gln Asp Pro Cys Gln Ser Asp Ser
    215                 220                 225 gga ggc ccc ctg gtc tgt gac gag acc ctc caa ggc atc ctc tcg tgg        954
Gly Gly Pro Leu Val Cys Asp Glu Thr Leu Gln Gly Ile Leu Ser Trp
230                 235                 240                 245 ggt gtt tac ccc tgt ggc tct gcc cag cat cca gct gtc tac acc cag       1002
Gly Val Tyr Pro Cys Gly Ser Ala Gln His Pro Ala Val Tyr Thr Gln
                250                 255                 260 atc tgc aaa tac atg tcc tgg atc aat aaa gtc ata cgc tcc aac tga       1050
Ile Cys Lys Tyr Met Ser Trp Ile Asn Lys Val Ile Arg Ser Asn  *
            265                 270                 275 tccagatgct acgctccagc tgatccagat gttatgctcc tgctgatcca gatgccaga      1110 ggctccatcg tccatcctct tcctcccag tcggctgaac tctcccttg tctgcactgt       1170
```

```
tcaaacctct gccgccctcc acacctctaa acatctcccc tctcacctca ttccccacc    1230 tatccccatt ctctgcctgt actgaagctg aaatgcagga agtggtggca aaggtttatt    1290
ccagagaagc caggaagccg gtcatcaccc agcctctgag agcagttact ggggtcaccc    1350
aacctgactt cctctgccac tccctgctgt gtgactttgg gcaagccaag tgccctctct    1410
gaacctcagt ttcctcatct gcaaaatggg aacaatgacg tgcctacctc ttagacatgt    1470
tgtgaggaga ctatgatata acatgtgtat gtaaatcttc atggtgattg tcatgtaagg    1530
cttaacacag tgggtggtga gttctgacta aaggttacct gttgtcgtga               1580
```

<210> SEQ ID NO 12
<211> LENGTH: 276
<212> TYPE: PRT
<213> ORGANISM: Homo sapien

<400> SEQUENCE: 12

```
Met Arg Ala Pro His Leu His Leu Ser Ala Ala Ser Gly Ala Arg Ala
 1               5                  10                  15

Leu Ala Lys Leu Leu Pro Leu Leu Met Ala Gln Leu Trp Ala Ala Glu
            20                  25                  30

Ala Ala Leu Leu Pro Gln Asn Asp Thr Arg Leu Asp Pro Glu Ala Tyr
        35                  40                  45

Gly Ser Pro Cys Ala Arg Gly Ser Gln Pro Trp Gln Val Ser Leu Phe
    50                  55                  60

Asn Gly Leu Ser Phe His Cys Ala Gly Val Leu Val Asp Gln Ser Trp
65                  70                  75                  80

Val Leu Thr Ala Ala His Cys Gly Asn Lys Pro Leu Trp Ala Arg Val
                85                  90                  95

Gly Asp Asp His Leu Leu Leu Leu Gln Gly Glu Gln Leu Arg Arg Thr
            100                 105                 110

Thr Arg Ser Val Val His Pro Lys Tyr His Gln Gly Ser Gly Pro Ile
        115                 120                 125

Leu Pro Arg Arg Thr Asp Glu His Asp Leu Met Leu Leu Lys Leu Ala
    130                 135                 140

Arg Pro Val Val Leu Gly Pro Arg Val Arg Ala Leu Gln Leu Pro Tyr
145                 150                 155                 160

Arg Cys Ala Gln Pro Gly Asp Gln Cys Gln Val Ala Gly Trp Gly Thr
                165                 170                 175

Thr Ala Ala Arg Arg Val Lys Tyr Asn Lys Gly Leu Thr Cys Ser Ser
            180                 185                 190

Ile Thr Ile Leu Ser Pro Lys Glu Cys Glu Val Phe Tyr Pro Gly Val
        195                 200                 205

Val Thr Asn Asn Met Ile Cys Ala Gly Leu Asp Arg Gly Gln Asp Pro
    210                 215                 220

Cys Gln Ser Asp Ser Gly Gly Pro Leu Val Cys Asp Glu Thr Leu Gln
225                 230                 235                 240

Gly Ile Leu Ser Trp Gly Val Tyr Pro Cys Gly Ser Ala Gln His Pro
                245                 250                 255

Ala Val Tyr Thr Gln Ile Cys Lys Tyr Met Ser Trp Ile Asn Lys Val
            260                 265                 270

Ile Arg Ser Asn
        275
```

<210> SEQ ID NO 13
<211> LENGTH: 1512

```
<212> TYPE: DNA
<213> ORGANISM: Homo sapien
<220> FEATURE:
<221> NAME/KEY: CDS
<222> LOCATION: (246)...(980)

<400> SEQUENCE: 13
aggcggacaa aacccgattg ttcctgggcc ctttccccat cgcgcctggg cctgctcccc      60
agcccggggc aggggcgggg gccagtgtgg tgacacacgc tgtagctgtc tccccggctg     120
gctggctcgc tctctcctgg ggacacagag gtcggcaggc agcacacaga gggacctacg     180
ggcagctgtt ccttccccg actcaagaat ccccggaggc ccggaggcct gcagcaggag     240 cggcc atg aag aag ctg atg gtg gtg ctg agt ctg att gct gca gcc tgg     290
      Met Lys Lys Leu Met Val Val Leu Ser Leu Ile Ala Ala Ala Trp
      1               5                   10                  15 gca gag gag cag aat aag ttg gtg cat ggc gga ccc tgc gac aag aca         338
Ala Glu Glu Gln Asn Lys Leu Val His Gly Gly Pro Cys Asp Lys Thr
                20                  25                  30 tct cac ccc tac caa gct gcc ctc tac acc tcg ggc cac ttg ctc tgt         386
Ser His Pro Tyr Gln Ala Ala Leu Tyr Thr Ser Gly His Leu Leu Cys
            35                  40                  45 ggt ggg gtc ctt atc cat cca ctg tgg gtc ctc aca gct gcc cac tgc         434
Gly Gly Val Leu Ile His Pro Leu Trp Val Leu Thr Ala Ala His Cys
        50                  55                  60 aaa aaa ccg aat ctt cag gtc ttc ctg ggg aag cat aac ctt cgg caa         482
Lys Lys Pro Asn Leu Gln Val Phe Leu Gly Lys His Asn Leu Arg Gln
65                  70                  75 agg gag agt tcc cag gag cag agt tct gtt gtc cgg gct gtg atc cac         530
Arg Glu Ser Ser Gln Glu Gln Ser Ser Val Val Arg Ala Val Ile His
 80                  85                  90                  95 cct gac tat gat gcc gcc agc cat gac cag gac atc atg ctg ttg cgc         578
Pro Asp Tyr Asp Ala Ala Ser His Asp Gln Asp Ile Met Leu Leu Arg
                100                 105                 110 ctg gca cgc cca gcc aaa ctc tct gaa ctc atc cag ccc ctt ccc ctg         626
Leu Ala Arg Pro Ala Lys Leu Ser Glu Leu Ile Gln Pro Leu Pro Leu
            115                 120                 125 gag agg gac tgc tca gcc aac acc acc agc tgc cac atc ctg ggc tgg         674
Glu Arg Asp Cys Ser Ala Asn Thr Thr Ser Cys His Ile Leu Gly Trp
        130                 135                 140 ggc aag aca gca gat ggt gat ttc cct gac acc atc cag tgt gca tac         722
Gly Lys Thr Ala Asp Gly Asp Phe Pro Asp Thr Ile Gln Cys Ala Tyr
145                 150                 155 atc cac ctg gtg tcc cgt gag gag tgt gag cat gcc tac cct ggc cag         770
Ile His Leu Val Ser Arg Glu Glu Cys Glu His Ala Tyr Pro Gly Gln
160                 165                 170                 175 atc acc cag aac atg ttg tgt gct ggg gat gag aag tac ggg aag gat         818
Ile Thr Gln Asn Met Leu Cys Ala Gly Asp Glu Lys Tyr Gly Lys Asp
                180                 185                 190 tcc tgc cag ggt gat tct ggg ggt ccg ctg gta tgt gga gac cac ctc         866
Ser Cys Gln Gly Asp Ser Gly Gly Pro Leu Val Cys Gly Asp His Leu
            195                 200                 205 cga ggc ctt gtg tca tgg ggt aac atc ccc tgt gga tca aag gag aag         914
Arg Gly Leu Val Ser Trp Gly Asn Ile Pro Cys Gly Ser Lys Glu Lys
        210                 215                 220 cca gga gtc tac acc aac gtc tgc aga tac acg aac tgg atc caa aaa         962
Pro Gly Val Tyr Thr Asn Val Cys Arg Tyr Thr Asn Trp Ile Gln Lys
225                 230                 235 acc att cag gcc aag tga ccctgacatg tgacatctac ctcccgacct              1010
Thr Ile Gln Ala Lys *
240
```

```
accaccccac tggctggttc cagaacgtct ctcacctaga ccttgcctcc cctcctctcc    1070
tgcccagctc tgaccctgat gcttaataaa cgcagcgacg tgagggtcct gattctccct    1130
ggttttaccc cagctccatc cttgcatcac tggggaggac gtgatgagtg aggacttggg    1190
tcctcggtct taccccacc actaagagaa tacaggaaaa tcccttctag gcatctcctc     1250
tccccaaccc ttccacacgt ttgatttctt cctgcagagg cccagccacg tgtctggaat    1310
cccagctccg ctgcttactg tcggtgtccc cttgggatgt acctttcttc actgcagatt    1370
tctcacctgt aagatgaaga taaggatgat acagtctcca taaggcagtg gctgttggaa    1430
agatttaagg tttcacacct atgacataca tggaatagca cctgggccac catgcactca    1490
ataaagaatg aattttatta tg                                             1512

<210> SEQ ID NO 14
<211> LENGTH: 244
<212> TYPE: PRT
<213> ORGANISM: Homo sapien

<400> SEQUENCE: 14

Met Lys Lys Leu Met Val Val Leu Ser Leu Ile Ala Ala Ala Trp Ala
 1               5                  10                  15

Glu Glu Gln Asn Lys Leu Val His Gly Gly Pro Cys Asp Lys Thr Ser
            20                  25                  30

His Pro Tyr Gln Ala Ala Leu Tyr Thr Ser Gly His Leu Leu Cys Gly
        35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
                85                  90                  95

Asp Tyr Asp Ala Ala Ser His Asp Gln Asp Ile Met Leu Leu Arg Leu
            100                 105                 110

Ala Arg Pro Ala Lys Leu Ser Glu Leu Ile Gln Pro Leu Pro Leu Glu
        115                 120                 125

Arg Asp Cys Ser Ala Asn Thr Thr Ser Cys His Ile Leu Gly Trp Gly
    130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
                165                 170                 175

Thr Gln Asn Met Leu Cys Ala Gly Asp Glu Lys Tyr Gly Lys Asp Ser
            180                 185                 190

Cys Gln Gly Asp Ser Gly Gly Pro Leu Val Cys Gly Asp His Leu Arg
        195                 200                 205

Gly Leu Val Ser Trp Gly Asn Ile Pro Cys Gly Ser Lys Glu Lys Pro
    210                 215                 220

Gly Val Tyr Thr Asn Val Cys Arg Tyr Thr Asn Trp Ile Gln Lys Thr
225                 230                 235                 240

Ile Gln Ala Lys

<210> SEQ ID NO 15
<211> LENGTH: 2892
<212> TYPE: DNA
<213> ORGANISM: Homo sapien
```

```
<220> FEATURE:
<221> NAME/KEY: CDS
<222> LOCATION: (88)...(618)

<400> SEQUENCE: 15
gcggcggcgg cggcggcggc aggagcccgg gaggcggagg cgggaggcgg cggcggcgcg        60
cggagacgca gcagcggcag cggcagc atg tcg gcc ggc gga gcg tca gtc ccg       114
                                Met Ser Ala Gly Gly Ala Ser Val Pro
                                 1               5 ccg ccc ccg aac ccc gcc gtg tcc ttc ccg ccg ccc cgg gtc acc ctg         162
Pro Pro Pro Asn Pro Ala Val Ser Phe Pro Pro Pro Arg Val Thr Leu
 10              15                  20                  25 ccc gcc ggc ccc gac atc ctg cgg acc tac tcg ggc gcc ttc gtc tgc         210
Pro Ala Gly Pro Asp Ile Leu Arg Thr Tyr Ser Gly Ala Phe Val Cys
             30                  35                  40 ctg gag att ctg ttc ggg ggt ctt gtc tgg att ttg gtt gcc tcc tcc         258
Leu Glu Ile Leu Phe Gly Gly Leu Val Trp Ile Leu Val Ala Ser Ser
         45                  50                  55 aat gtt cct cta cct cta cta caa gga tgg gtc atg ttt gtg tcc gtg         306
Asn Val Pro Leu Pro Leu Leu Gln Gly Trp Val Met Phe Val Ser Val
     60                  65                  70 aca gcg ttt ttc ttt tcg ctc ctc ttt ctg ggc atg ttc ctc tct ggc         354
Thr Ala Phe Phe Phe Ser Leu Leu Phe Leu Gly Met Phe Leu Ser Gly
 75                  80                  85 atg gtg gct caa att gat gct aac tgg aac ttc ctg gat ttt gcc tac         402
Met Val Ala Gln Ile Asp Ala Asn Trp Asn Phe Leu Asp Phe Ala Tyr
 90                  95                 100                 105 cat ttt aca gta ttt gtc ttc tat ttt gga gcc ttt tta ttg gaa gca         450
His Phe Thr Val Phe Val Phe Tyr Phe Gly Ala Phe Leu Leu Glu Ala
             110                 115                 120 gca gcc aca tcc ctg cat gat ttg cat tgc aat aca acc ata acc ggg         498
Ala Ala Thr Ser Leu His Asp Leu His Cys Asn Thr Thr Ile Thr Gly
         125                 130                 135 cag cca ctc ctg agt gat aac cag tat aac ata aac gta gca gcc tca         546
Gln Pro Leu Leu Ser Asp Asn Gln Tyr Asn Ile Asn Val Ala Ala Ser
     140                 145                 150 att ttt gcc ttt atg acg aca gct tgt tat ggt tgc agt ttg ggt ctg         594
Ile Phe Ala Phe Met Thr Thr Ala Cys Tyr Gly Cys Ser Leu Gly Leu
 155                 160                 165 gct tta cga aga tgg cga ccg taa cactccttag aaactggcag tcgtatgtta        648
Ala Leu Arg Arg Trp Arg Pro *
170                 175 gtttcacttg tctactttat atgtctgatc aatttggata ccattttgtc cagatgcaaa       708
aacattccaa aagtaatgtg tttagtagag agagactcta agctcaagtt ctggtttatt       768
tcatggatgg aatgttaatt ttattatgat attaaagaaa tggcctttta ttttacatct       828 ctccccttt tcccttcc cctttatttt cctcctttc tttctgaaag tttcctttta          888
tgtccataaa atacaaatat attgttcata aaaaattagt atcccttttg tttggttgct       948
gagtcacctg aaccttaatt ttaattggta attacagccc ctaaaaaaaa cacatttcaa       1008
ataggcttcc cactaaactc tatattttag tgtaaaccag gaattggcac acttttttta      1068
gaatgggcca gatggtaaat atttatgctt cacggtccat acagtctctg tcacaactat      1128
tcagttctgc tagtatagcg tgaaagcagc tatacacaat acagaaatga atgagtgtgg      1188
ttatgttcta ataaaactta tttataaaaa caaggggagg ctgggtttag cctgtgggcc      1248
atagtttgtc aaccactggt gtaaaacctt agttatatat gatctgcatt ttcttgaact      1308
gatcattgaa aacttataaa cctaacagaa aagccacata atatttagtg tcattatgca      1368
```

```
ataatcacat tgcctttgtg ttaatagtca aatacttacc tttggagaat acttacctttt    1428 ggaggaatgt ataaaatttc tcaggcagag tcctggatat aggaaaaagt aatttatgaa    1488
gtaaacttca gttgcttaat caaactaatg atagtctaac aactgagcaa gatcctcatc    1548
tgagagtgct taaatgggat ccccagaga ccattaacca atactggaac tggtatctag    1608
ctactgatgt cttactttga gtttatttat gcttcagaat acagttgttt gccctgtgca    1668
tgaatatacc catatttgtg tgtggatatg tgaagctttt ccaaatagag ctctcagaag    1728
aattaagttt ttacttctaa ttattttgca ttactttgag ttaaatttga atagagtatt    1788
aaatataaag ttgtagattc ttatgtgttt ttgtattagc ccagacatct gtaatgtttt    1848
tgcactggtg acagacaaaa tctgttttaa aatcatatcc agcacaaaaa ctatttctgg    1908
ctgaatagca cagaaaagta ttttaaccta cctgtagaga tcctcgtcat ggaaaggtgc    1968
caaactgttt tgaatggaag acaagtaag agtgaggcca cagttcccac cacacgaggg    2028
cttttgtatt gttctacttt ttcagcccctt tactttctgg ctgaagcatc cccttggagt    2088
gccatgtata agttgggcta ttagagttca tggaacatag aacaaccatg aatgagtggc    2148
atgatccgtg cttaatgatc aagtgttact tatctaataa tcctctagaa agaaccctgt    2208
tagatcttgg tttgtgataa aaatataaag acagaagaca tgaggaaaaa caaaaggttt    2268
gaggaaatca ggcatatgac tttatactta acatcagatc ttttctataa tatcctacta    2328
ctttggtttt cctagctcca taccacacac ctaaacctgt attatgaatt acatattaca    2388
aagtcataaa tgtgccatat ggatatacag tacattctag ttggaatcgt ttactctgct    2448
agaatttagg tgtgagattt tttgtttccc aggtatagca ggcttatgtt tggtggcatt    2508
aaattggttt ctttaaaatg ctttggtggc acttttgtaa acagattgct tctagattgt    2568
tacaaaccaa gcctaagaca catctgtgaa tacttagatt tgtagcttaa tcacattcta    2628
gacttgtgag ttgaatgaca aagcagttga acaaaaatta tggcatttaa gaatttaaca    2688
tgtcttagct gtaaaaatga gaaagtgttg gttggtttta aaatctggta actccatgat    2748
gaaaagaaat ttatttttata cgtgttatgt ctctaataaa gtattcattt gataaaaaaa    2808
aaaaaaaaaa gggcggccgc tctagaggat ccaagcttac gtacgcgtgc atgcgacgtc    2868
atagctcttc tatagtgtca ccta    2892
```

<210> SEQ ID NO 16
<211> LENGTH: 176
<212> TYPE: PRT
<213> ORGANISM: Homo sapien

<400> SEQUENCE: 16

```
Met Ser Ala Gly Gly Ala Ser Val Pro Pro Pro Asn Pro Ala Val
 1               5                  10                  15

Ser Phe Pro Pro Pro Arg Val Thr Leu Pro Ala Gly Pro Asp Ile Leu
            20                  25                  30

Arg Thr Tyr Ser Gly Ala Phe Val Cys Leu Glu Ile Leu Phe Gly Gly
        35                  40                  45

Leu Val Trp Ile Leu Val Ala Ser Ser Asn Val Pro Leu Pro Leu Leu
    50                  55                  60

Gln Gly Trp Val Met Phe Val Ser Val Thr Ala Phe Phe Phe Ser Leu
65                  70                  75                  80

Leu Phe Leu Gly Met Phe Leu Ser Gly Met Val Ala Gln Ile Asp Ala
                85                  90                  95
```

```
Asn Trp Asn Phe Leu Asp Phe Ala Tyr His Phe Thr Val Phe Val Phe
            100                 105                 110
Tyr Phe Gly Ala Phe Leu Glu Ala Ala Ala Thr Ser Leu His Asp
        115                 120                 125
Leu His Cys Asn Thr Thr Ile Thr Gly Gln Pro Leu Leu Ser Asp Asn
    130                 135                 140
Gln Tyr Asn Ile Asn Val Ala Ala Ser Ile Phe Ala Phe Met Thr Thr
145                 150                 155                 160
Ala Cys Tyr Gly Cys Ser Leu Gly Leu Ala Leu Arg Arg Trp Arg Pro
                165                 170                 175

<210> SEQ ID NO 17
<211> LENGTH: 4458
<212> TYPE: DNA
<213> ORGANISM: Homo sapien
<220> FEATURE:
<221> NAME/KEY: CDS
<222> LOCATION: (21)...(404)

<400> SEQUENCE: 17
gtcgacccac gcgtccggcg atg cct cgc tgg ctt ctg ctt tca ttg acc ttt      53
                     Met Pro Arg Trp Leu Leu Leu Ser Leu Thr Phe
                      1               5                   10 gcg ggt ctg ttc ccg ctg cgg cgc cgg cag ctg ctt ggt agt tgc ggg       101
Ala Gly Leu Phe Pro Leu Arg Arg Arg Gln Leu Leu Gly Ser Cys Gly
         15                  20                  25 ggg cgt gag ggc ggt ggc cca gac caa ccg gct ggc agc cca gct ccg       149
Gly Arg Glu Gly Gly Gly Pro Asp Gln Pro Ala Gly Ser Pro Ala Pro
     30                  35                  40 ctc cgc ccg ccc ctg cct cgg acc ctg cgc ctg agg aag tat cga ggc       197
Leu Arg Pro Pro Leu Pro Arg Thr Leu Arg Leu Arg Lys Tyr Arg Gly
 45                  50                  55 aac cct ctg cca ccc gaa gtt cgt ggg tcg ctc cca gag ggc gcg ccc       245
Asn Pro Leu Pro Pro Glu Val Arg Gly Ser Leu Pro Glu Gly Ala Pro
 60                  65                  70                  75 tgg agc cga gcg ccc ttg ggc ggc cat ctg gag gcc agg tgc ggg ccg       293
Trp Ser Arg Ala Pro Leu Gly Gly His Leu Glu Ala Arg Cys Gly Pro
                 80                  85                  90 cga acc cgc gag gag cgc gcg gcg ggc gcg gcg gcg acg gca gga gga       341
Arg Thr Arg Glu Glu Arg Ala Ala Gly Ala Ala Ala Thr Ala Gly Gly
             95                 100                 105 ggg gcc ggg agc ccg ggc gcc gcc gaa gga cgc ccc gtc ctc cac atg       389
Gly Ala Gly Ser Pro Gly Ala Ala Glu Gly Arg Pro Val Leu His Met
         110                 115                 120 ctg cca ctt ggc tga gccgggcgcc ggcgagaagg cggcgccgct gccctggcag       444
Leu Pro Leu Gly *
         125 ctggactgca ctttgccccc gcccggcctc agctgccgcc cgcccagacg ccagcaagcc     504 cccctcccac gacagggctg ctccgggagc ttcggagacc cgccccgggc ctgagcgcag     564 gctgcctccg ggaccccacg gctgtccgga cgtgccatgg gcgcgcagct gccgggcaac     624 gtgttgtgta agtgaacatc tgggaggtaa acactacacg tgaagagtgg tgaaagggaa     684 cattgattac tgaagtgccc tggagaggga aagcactggt caacatcaca tggacaaatt     744 tcattgtttt ctaaagatgg cctggaagta gtctttgcca ctgcttcctc cacaaacagc     804 tcttcataac atgggctgca tgaaatcaaa gcaaactttc ccatttccta ccatatatga     864 aggtgagaag cagcatgaga gtgaagaacc ctttatgcca gaagagagat gtctacctag     924 gatggcttct ccagttaatg tcaaagagga agtgaaggaa cctccaggga ccaatattgt     984
```

-continued

```
gatcttggaa tatgcacacc gcctgtctca ggatatcttg tgtgatgcct tgcagcaatg      1044
ggcatgcaat aacatcaagt accatgacat tccatacatt gagagtgagg ggccttgagg      1104
ctgtaggatg acaacacttt gactgtggag gtgctagttt gaataaatgt gacaaaagca      1164
aaaactggtg tgaaaagta caaataacta tctggattta aaaatgtgtc tacgataatg       1224
tcactattat aagaacaact aggatgaaat gcattttaag tacttctatg ttaacagcaa      1284
tttctgttta gtcttagatt ttagtcatct gaagggctga acagaggtcc tgtgacaccc     1344
aataatcagc tgaatgtcac agcacttctt cctaagtaat ggcatcacca agaaaatgc       1404 taaggaataa aaactgcccc aaattccaat ggttgaagtt tatcctttaa ataacaatt       1464 tttgttata cccaaaaaaa gtccagatat gaaagggct tttctaaaat tcttggcga         1524 gggaatggca ctcaaatcat agtgattaac agtaagtctt gtttgtttgt caaggatctc     1584
tacttcttga cacaaatgaa ccctgtcttt aataagataa gatatttatt tttgtagatg    1644
agaagtgtaa ctaccacctt ggacctcagg gccctaacta attacagctg ttactggacg     1704
actcagactt tgtgcctaaa gccatcttag agataacagt ttatagaagc catgacatta     1764
gtgtttattg cattgaatta agcccagtga tataactata caagaaaaca agtatgggta    1824
ccttttacaa agagcaatcc aataaatctt aaaaataaca gaaacttagt ctgcaaggta    1884
gaaagtttca gttttaattc tgtattaagc tttactatct cagaggtaca gagggctgga    1944
atatgggcat ttatttccag ttttttcttg actagtaagg cggtcaccat taaaatagac     2004
cagatgataa tgcatgaaga tttacagttg tattgcaaaa cggaaaagat aaaactgtcc   2064
tttgaggaga gtactcgttt tctgggtttt tgttattttt tagtggtaac acaagcctat    2124
agggcattta tagccaccta ttatactgtt tccataagcc tggctacctt ttagggaagc   2184 tatttttct ctttcatttt tactgtcaca gcacatacac acacacccttt tgttttaaa     2244 ggattaagta ctgtttgaag atcagtggta acagaaaatt tgggagggag aagaagaaat   2304
taagacatga cttgttagaa aattaagact tcagtttcta gaattatctt ttcatcaaga   2364
tttggtagac attgagttta aatggaaagg aaattattta agcctgtgta tgttagatcc   2424
acaatacacc attggtattg aaatataaag gttaaaaaa aggcttatga cctctttaat     2484
gagataaata tgtatttgtc ttgtaagcag gcagaaaatc tacctctaat tttaacacta   2544
atactttgaa acccacaatc aaatagagtg aattctccaa gttacataag caaggaaaac   2604
attatttgaa atatgccatg ttttcgttgc ctttggacac ctcatcattc aactctaatt   2664
ttaccgagtc ccgggatttg tactgtccca ttgtacttgc aatctacaat ttatataata   2724 gaaaacaac caaacccatt catacaagga tctgaagtta taggttaag gcagaaagt      2784 ttcccataag tataaaacat ttccaggtca tgaagagtag tttaggttga gtgacaaaag   2844
cctaggtgtg gttgttttc attcattttg catctcacac caagacattt ttgctgcaag    2904
gtcatctgct gcttaaaatg tacaattagg tatataaaat aagtacaatg gtgaaaacac   2964
aaagccaggt aaagcagcat gccccactaa attttcagt atacataggg acagacaagt    3024
gagttttggt tgtatctaaa tatttaatt tcaggttcct tctgtgccct gggccactat     3084
ttcccagggg tgtgacagag atgcctgcca gatccatatc aactgaagt ctgatttctg     3144 ttgctgccct tcctcagcaa ctatggcagt atactttat caccaagcac cactcccttg    3204
tccctgaatc acattttaat agagtacaat atcttctgta caatatttct gaaacactta   3264
tgtctgaaat atatgctgta ttgtatgtta acccatgaca tatatgaact acaaggcttg   3324
```

```
                                                                -continued cataatcagt gagctagtgg ataaatcaag acaggagcaa atgggagaaa gatgaataaa      3384
caaatgaaaa aagatgaata aatgaataag agagatgaat aaacaaattt acattacatg      3444
tgatagttat catggtatgg ccttcatgac aagatggatg agaatatcac tgataggata      3504
ttagccttct ttcatatctt tatattgaaa tatgggcttt acttcaattt gaaggtcttt      3564
catgaacaat aaaagagagt agaaggactg tctgagaagg caggagacat ataaaacaga      3624
tgactgaaag actgactagc tcctggaaag ggaaacattt ggaacatcca gagtaaggca      3684
aatgggcttc taccagcaca acaaagagcc tccaggtggc aacatggaag caggttatca      3744
gagaaaataa atgtgcaaat tccttattta caatgactca cttaacccca caaacatgtt      3804
tcactgctgc cttccccagt tgtcgcttat gtactgttgt tacctttcag ttacatgcct      3864
ttgatcctaa aattctctac ttttgttgcc ttatcagttc tttgcaatct gcctgtggtt      3924
atcagcactt aaagcacaat tttgaagggg aaaaaaatga taatcacctt agtcccaaag      3984
aaataatttg tcaaactgcc ttattagtat taaaaacaga cacactgaat gaagtagcat      4044
gatacgcata tatcctactc agtatcattg gccttttatc aaatggggaa actatacttt      4104
tgtattacat agttttagaa atcgaaagtt agagactctt tataagtaat gtcaaggaac      4164
agtaatttaa aaacaaagtt ctaacaaata tattgtttgc ttaatcacaa tgccctcaac      4224
ttgtatttga ataactaaat aggacatgtc ttccttggag ctgtgggcat tagttcagaa      4284
gcactacctg catcttaatt ttcaaaactt aagttttatt agcaaatcct cttctctgta      4344
agacttagct atgaagtggt atattttttc caaatatttt tctgaaaaca tttgttgttg      4404
taactgcaca ataaaagtcc agttgcaatt aaaaaaaaaa aaaaaaaaaa aaaa           4458

<210> SEQ ID NO 18
<211> LENGTH: 127
<212> TYPE: PRT
<213> ORGANISM: Homo sapien

<400> SEQUENCE: 18

Met Pro Arg Trp Leu Leu Leu Ser Leu Thr Phe Ala Gly Leu Phe Pro
1               5                   10                  15

Leu Arg Arg Arg Gln Leu Leu Gly Ser Cys Gly Gly Arg Glu Gly Gly
            20                  25                  30

Gly Pro Asp Gln Pro Ala Gly Ser Pro Ala Pro Leu Arg Pro Pro Leu
        35                  40                  45

Pro Arg Thr Leu Arg Leu Arg Lys Tyr Arg Gly Asn Pro Leu Pro Pro
    50                  55                  60

Glu Val Arg Gly Ser Leu Pro Glu Gly Ala Pro Trp Ser Arg Ala Pro
65                  70                  75                  80

Leu Gly Gly His Leu Glu Ala Arg Cys Gly Pro Arg Thr Arg Glu Glu
                85                  90                  95

Arg Ala Ala Gly Ala Ala Ala Thr Ala Gly Gly Ala Gly Ser Pro
            100                 105                 110

Gly Ala Ala Glu Gly Arg Pro Val Leu His Met Leu Pro Leu Gly
        115                 120                 125

<210> SEQ ID NO 19
<211> LENGTH: 1127
<212> TYPE: DNA
<213> ORGANISM: Homo sapien
<220> FEATURE:
<221> NAME/KEY: CDS
<222> LOCATION: (48)...(851)
```

<400> SEQUENCE: 19

```
accaaatcaa ccataggtcc aagaacaatt gtctctggac ggcagct atg cga ctc       56
                                                    Met Arg Leu
                                                     1 acc gtg ctg tgt gct gtg tgc ctg ctg cct ggc agc ctg gcc ctg ccg      104
Thr Val Leu Cys Ala Val Cys Leu Leu Pro Gly Ser Leu Ala Leu Pro
      5                  10                  15 ctg cct cag gag gcg gga ggc atg agt gag cta cag tgg gaa cag gct      152
Leu Pro Gln Glu Ala Gly Gly Met Ser Glu Leu Gln Trp Glu Gln Ala
 20                  25                  30                  35 cag gac tat ctc aag aga ttt tat ctc tat gac tca gaa aca aaa aat      200
Gln Asp Tyr Leu Lys Arg Phe Tyr Leu Tyr Asp Ser Glu Thr Lys Asn
                 40                  45                  50 gcc aac agt tta gaa gcc aaa ctc aag gag atg caa aaa ttc ttt ggc      248
Ala Asn Ser Leu Glu Ala Lys Leu Lys Glu Met Gln Lys Phe Phe Gly
             55                  60                  65 cta cct ata act gga atg tta aac tcc cgc gtc ata gaa ata atg cag      296
Leu Pro Ile Thr Gly Met Leu Asn Ser Arg Val Ile Glu Ile Met Gln
         70                  75                  80 aag ccc aga tgt gga gtg cca gat gtt gca gaa tac tca cta ttt cca      344
Lys Pro Arg Cys Gly Val Pro Asp Val Ala Glu Tyr Ser Leu Phe Pro
     85                  90                  95 aat agc cca aaa tgg act tcc aaa gtg gtc acc tac agg atc gta tca      392
Asn Ser Pro Lys Trp Thr Ser Lys Val Val Thr Tyr Arg Ile Val Ser
100                 105                 110                 115 tat act cga gac tta ccg cat att aca gtg gat cga tta gtg tca aag      440
Tyr Thr Arg Asp Leu Pro His Ile Thr Val Asp Arg Leu Val Ser Lys
                 120                 125                 130 gct tta aac atg tgg ggc aaa gag atc ccc ctg cat ttc agg aaa gtt      488
Ala Leu Asn Met Trp Gly Lys Glu Ile Pro Leu His Phe Arg Lys Val
             135                 140                 145 gta tgg gga act gct gac atc atg att ggc ttt gcg cga gga gct cat      536
Val Trp Gly Thr Ala Asp Ile Met Ile Gly Phe Ala Arg Gly Ala His
         150                 155                 160 ggg gac tcc tac cca ttt gat ggg cca gga aac acg ctg gct cat gcc      584
Gly Asp Ser Tyr Pro Phe Asp Gly Pro Gly Asn Thr Leu Ala His Ala
     165                 170                 175 ttt gcg cct ggg aca ggt ctc gga gga gat gct cac ttc gat gag gat      632
Phe Ala Pro Gly Thr Gly Leu Gly Gly Asp Ala His Phe Asp Glu Asp
180                 185                 190                 195 gaa cgc tgg acg gat ggt agc agt cta ggg att aac ttc ctg tat gct      680
Glu Arg Trp Thr Asp Gly Ser Ser Leu Gly Ile Asn Phe Leu Tyr Ala
                 200                 205                 210 gca act cat gaa ctt ggc cat tct ttg ggt atg gga cat tcc tct gat      728
Ala Thr His Glu Leu Gly His Ser Leu Gly Met Gly His Ser Ser Asp
             215                 220                 225 cct aat gca gtg atg tat cca acc tat gga aat gga gat ccc caa aat      776
Pro Asn Ala Val Met Tyr Pro Thr Tyr Gly Asn Gly Asp Pro Gln Asn
         230                 235                 240 ttt aaa ctt tcc cag gat gat att aaa ggc att cag aaa cta tat gga      824
Phe Lys Leu Ser Gln Asp Asp Ile Lys Gly Ile Gln Lys Leu Tyr Gly
     245                 250                 255 aag aga agt aat tca aga aag aaa tag aaacttcagg cagaacatcc            871
Lys Arg Ser Asn Ser Arg Lys Lys  *
260                 265 attcattcat tcattggatt gtatatcatt gttgcacaat cagaattgat aagcactgtt    931
cctccactcc atttagcaat tatgtcaccc tttttttattg cagttggttt ttgaatgtct   991
ttcactcctt ttattggtta aactccttta tggtgtgact gtgtcttatt ccatctatga   1051
```
gctttgtcag tgcgcgtaga tgtcaataaa tgttacatac acaaataaat aaaatgttta    1111
ttccatggta aattta                                                    1127

<210> SEQ ID NO 20
<211> LENGTH: 267
<212> TYPE: PRT
<213> ORGANISM: Homo sapien

<400> SEQUENCE: 20

Met Arg Leu Thr Val Leu Cys Ala Val Cys Leu Leu Pro Gly Ser Leu
 1               5                  10                  15

Ala Leu Pro Leu Pro Gln Glu Ala Gly Gly Met Ser Glu Leu Gln Trp
                20                  25                  30

Glu Gln Ala Gln Asp Tyr Leu Lys Arg Phe Tyr Leu Tyr Asp Ser Glu
            35                  40                  45

Thr Lys Asn Ala Asn Ser Leu Glu Ala Lys Leu Lys Glu Met Gln Lys
 50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205

Leu Tyr Ala Ala Thr His Glu Leu Gly His Ser Leu Gly Met Gly His
    210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
            260                 265

<210> SEQ ID NO 21
<211> LENGTH: 5093
<212> TYPE: DNA
<213> ORGANISM: Homo sapien
<220> FEATURE:
<221> NAME/KEY: CDS
<222> LOCATION: (136)...(1935)

<400> SEQUENCE: 21
aggtgacagc tggagggagg agcgggggtg gagccggggg aagggtgggg aggggatggg    60
ctggagctcc gggcagtgtg cgaggcgcac gcacaggagc ctgcactctg cgtcccgcac   120

```
                                                              -continued cccagcagcc gcgcc atg agc cgg agt ctc ttg ctc tgg ttc ttg ctg ttc        171
              Met Ser Arg Ser Leu Leu Leu Trp Phe Leu Leu Phe
               1               5                  10 ctg ctc ctg ctc ccg ccg ctc ccc gtc ctg ctc gcg gac cca ggg gcg        219
Leu Leu Leu Leu Pro Pro Leu Pro Val Leu Leu Ala Asp Pro Gly Ala
            15              20              25 ccc acg cca gtg aat ccc tgt tgt tac tat cca tgc cag cac cag ggc        267
Pro Thr Pro Val Asn Pro Cys Cys Tyr Tyr Pro Cys Gln His Gln Gly
         30              35              40 atc tgt gtc cgc ttc ggc ctt gac cgc tac cag tgt gac tgc acc cgc        315
Ile Cys Val Arg Phe Gly Leu Asp Arg Tyr Gln Cys Asp Cys Thr Arg
 45              50              55              60 acg ggc tat tcc ggc ccc aac tgc acc atc cct ggc ctg tgg acc tgg        363
Thr Gly Tyr Ser Gly Pro Asn Cys Thr Ile Pro Gly Leu Trp Thr Trp
                 65              70              75 ctc cgg aat tca ctg cgg ccc agc ccc tct ttc acc cac ttc ctg ctc        411
Leu Arg Asn Ser Leu Arg Pro Ser Pro Ser Phe Thr His Phe Leu Leu
             80              85              90 act cac ggg cgc tgg ttc tgg gag ttt gtc aat gcc acc ttc atc cga        459
Thr His Gly Arg Trp Phe Trp Glu Phe Val Asn Ala Thr Phe Ile Arg
         95              100             105 gag atg ctc atg cgc ctg gta ctc aca gtg cgc tcc aac ctt atc ccc        507
Glu Met Leu Met Arg Leu Val Leu Thr Val Arg Ser Asn Leu Ile Pro
     110             115             120 agt ccc ccc acc tac aac tca gca cat gac tac atc agc tgg gag tct        555
Ser Pro Pro Thr Tyr Asn Ser Ala His Asp Tyr Ile Ser Trp Glu Ser
125             130             135             140 ttc tcc aac gtg agc tat tac act cgt att ctg ccc tct gtg cct aaa        603
Phe Ser Asn Val Ser Tyr Tyr Thr Arg Ile Leu Pro Ser Val Pro Lys
                145             150             155 gat tgc ccc aca ccc atg gga acc aaa ggg aag aag cag ttg cca gat        651
Asp Cys Pro Thr Pro Met Gly Thr Lys Gly Lys Lys Gln Leu Pro Asp
            160             165             170 gcc cag ctc ctg gcc cgc cgc ttc ctc ctc agg agg aag ttc ata cct        699
Ala Gln Leu Leu Ala Arg Arg Phe Leu Leu Arg Arg Lys Phe Ile Pro
        175             180             185 gac ccc caa ggc acc aac ctc atg ttt gcc ttc ttt gca caa cac ttc        747
Asp Pro Gln Gly Thr Asn Leu Met Phe Ala Phe Phe Ala Gln His Phe
    190             195             200 acc cac cag ttc ttc aaa act tct ggc aag atg ggt cct ggc ttc acc        795
Thr His Gln Phe Phe Lys Thr Ser Gly Lys Met Gly Pro Gly Phe Thr
205             210             215             220 aag gcc ttg ggc cat ggg gta gac ctc ggc cac att tat gga gac aat        843
Lys Ala Leu Gly His Gly Val Asp Leu Gly His Ile Tyr Gly Asp Asn
                225             230             235 ctg gag cgt cag tat caa ctg cgg ctc ttt aag gat ggg aaa ctc aag        891
Leu Glu Arg Gln Tyr Gln Leu Arg Leu Phe Lys Asp Gly Lys Leu Lys
            240             245             250 tac cag gtg ctg gat gga gaa atg tac ccg ccc tcg gta gaa gag gcg        939
Tyr Gln Val Leu Asp Gly Glu Met Tyr Pro Pro Ser Val Glu Glu Ala
        255             260             265 cct gtg ttg atg cac tac ccc cga ggc atc ccg ccc cag agc cag atg        987
Pro Val Leu Met His Tyr Pro Arg Gly Ile Pro Pro Gln Ser Gln Met
    270             275             280 gct gtg ggc cag gag gtg ttt ggg ctg ctt cct ggg ctc atg ctg tat       1035
Ala Val Gly Gln Glu Val Phe Gly Leu Leu Pro Gly Leu Met Leu Tyr
285             290             295             300 gcc acg ctc tgg cta cgt gag cac aac cgt gtg tgt gac ctg ctg aag       1083
Ala Thr Leu Trp Leu Arg Glu His Asn Arg Val Cys Asp Leu Leu Lys
                305             310             315
```

-continued

| | |
|---|---|
| gct gag cac ccc acc tgg ggc gat gag cag ctt ttc cag acg acc cgc<br>Ala Glu His Pro Thr Trp Gly Asp Glu Gln Leu Phe Gln Thr Thr Arg<br>320 325 330 | 1131 |
| ctc atc ctc ata ggg gag acc atc aag att gtc atc gag gag tac gtg<br>Leu Ile Leu Ile Gly Glu Thr Ile Lys Ile Val Ile Glu Glu Tyr Val<br>335 340 345 | 1179 |
| cag cag ctg agt ggc tat ttc ctg cag ctg aaa ttt gac cca gag ctg<br>Gln Gln Leu Ser Gly Tyr Phe Leu Gln Leu Lys Phe Asp Pro Glu Leu<br>350 355 360 | 1227 |
| ctg ttc ggt gtc cag ttc caa tac cgc aac cgc att gcc atg gag ttc<br>Leu Phe Gly Val Gln Phe Gln Tyr Arg Asn Arg Ile Ala Met Glu Phe<br>365 370 375 380 | 1275 |
| aac cat ctc tac cac tgg cac ccc ctc atg cct gac tcc ttc aag gtg<br>Asn His Leu Tyr His Trp His Pro Leu Met Pro Asp Ser Phe Lys Val<br>385 390 395 | 1323 |
| ggc tcc cag gag tac agc tac gag cag ttc ttg ttc aac acc tcc atg<br>Gly Ser Gln Glu Tyr Ser Tyr Glu Gln Phe Leu Phe Asn Thr Ser Met<br>400 405 410 | 1371 |
| ttg gtg gac tat ggg gtt gag gcc ctg gtg gat gcc ttc tct cgc cag<br>Leu Val Asp Tyr Gly Val Glu Ala Leu Val Asp Ala Phe Ser Arg Gln<br>415 420 425 | 1419 |
| att gct ggc cgg atc ggt ggg ggc agg aac atg gac cac cac atc ctg<br>Ile Ala Gly Arg Ile Gly Gly Gly Arg Asn Met Asp His His Ile Leu<br>430 435 440 | 1467 |
| cat gtg gct gtg gat gtc atc agg gag tct cgg gag atg cgg ctg cag<br>His Val Ala Val Asp Val Ile Arg Glu Ser Arg Glu Met Arg Leu Gln<br>445 450 455 460 | 1515 |
| ccc ttc aat gag tac cgc aag agg ttt ggc atg aaa ccc tac acc tcc<br>Pro Phe Asn Glu Tyr Arg Lys Arg Phe Gly Met Lys Pro Tyr Thr Ser<br>465 470 475 | 1563 |
| ttc cag gag ctc gta gga gag aag gag atg gca gca gag ttg gag gaa<br>Phe Gln Glu Leu Val Gly Glu Lys Glu Met Ala Ala Glu Leu Glu Glu<br>480 485 490 | 1611 |
| ttg tat gga gac att gat gcg ttg gag ttc tac cct gga ctg ctt ctt<br>Leu Tyr Gly Asp Ile Asp Ala Leu Glu Phe Tyr Pro Gly Leu Leu Leu<br>495 500 505 | 1659 |
| gaa aag tgc cat cca aac tct atc ttt ggg gag agt atg ata gag att<br>Glu Lys Cys His Pro Asn Ser Ile Phe Gly Glu Ser Met Ile Glu Ile<br>510 515 520 | 1707 |
| ggg gct ccc ttt tcc ctc aag ggt ctc cta ggg aat ccc atc tgt tct<br>Gly Ala Pro Phe Ser Leu Lys Gly Leu Leu Gly Asn Pro Ile Cys Ser<br>525 530 535 540 | 1755 |
| ccg gag tac tgg aag ccg agc aca ttt ggc ggc gag gtg ggc ttt aac<br>Pro Glu Tyr Trp Lys Pro Ser Thr Phe Gly Gly Glu Val Gly Phe Asn<br>545 550 555 | 1803 |
| att gtc aag acg gcc aca ctg aag aag ctg gtc tgc ctc aac acc aag<br>Ile Val Lys Thr Ala Thr Leu Lys Lys Leu Val Cys Leu Asn Thr Lys<br>560 565 570 | 1851 |
| acc tgt ccc tac gtt tcc ttc cgt gtg ccg gat gcc agt cag gat gat<br>Thr Cys Pro Tyr Val Ser Phe Arg Val Pro Asp Ala Ser Gln Asp Asp<br>575 580 585 | 1899 |
| ggg cct gct gtg gag cga cca tcc aca gag ctc tga ggggcaggaa<br>Gly Pro Ala Val Glu Arg Pro Ser Thr Glu Leu *<br>590 595 | 1945 |
| agcagcattc tggaggggag agctttgtgc ttgtcattcc agagtgctga ggccagggct | 2005 |
| gatggtctta aatgctcatt ttctggtttg gcatggtgag tgttgggggtt gacatttaga | 2065 |
| actttaagtc tcacccatta tctggaatat tgtgattctg tttattcttc cagaatgctg | 2125 |

```
aactccttgt tagcccttca gattgttagg agtggttctc atttggtctg ccagaatact    2185
ggttcttag  ttgacaacct agaatgtcag atttctggtt gatttgtaac acagtcattc    2245
taggatgtgg agctactgat gaaatctgct agaaagttag ggggttctta ttttgcattc    2305
cagaatcttg actttctgat tggtgattca aagtgttgtg ttcctggctg atgatccaga    2365
acagtggctc gtatcccaaa tctgtcagca tctggctgtc tagaatgtgg atttgattca    2425
ttttcctgtt cagtgagata tcatagagac ggagatccta aggtccaaca agaatgcatt    2485
ccctgaatct gtgcctgcac tgagagggca aggaagtggg gtgttcttct tgggaccccc    2545
actaagaccc tggtctgagg atgtagagag aacaggtggg ctgtattcac gccattggtt    2605
ggaagctacc agagctctat ccccatccag gtcttgactc atggcagctg tttctcatga    2665
agctaataaa attcgctttc taaagttacc tgttatatat ctcttttggt cccatcctct    2725
aaagcagagg caacactgga acatggctag cctttcttgt agccatggct gggcgtgcta    2785
gaggttgcag catgagactt tctgctggga tccttgggcc catcactgta tagacatgct    2845
accactggta cttcctttct ccctgcgggc caggcactgc cctttcagg  aagctctctt    2905
aaaatacccc ttgccccaga cctggaagat ataacattca gttcccacca tctgattaaa    2965
acaacttcct cccttacaga gcatacaaca gaggggcac  ccggggagga gagcacatac    3025
tgtgttccaa tttcacgctt ttaattctca tttgttctca caccaacagt gtgaagtgcg    3085
tggtataatc tccatttcaa accaaggaa  gcagcctcag agtggtcgag tgacacacct    3145
cacgcaggct gagtccagag cttgtgctcc tcttgattcc tggtttgact cagttccagg    3205
cctgatcttg cctgtctggc tcagggtcaa agacagaatg gtggagtgta gcctccacct    3265
gatattcagg ctactcattc agtcccaaat atgtattttc ctaagtgttt actatgtgcc    3325
agttcctgta acaggtgtgg ggacacagca gtgagtaatc aatacagaca aggttctgcc    3385
cttatggagc tcacactcca gtggcagaca aacagaccat aaataaggaa acgatgaaat    3445
aagatatata caaggtgagt gtgacttccc ttctaacccc ctctgctctg tcctccccta    3505
ttgcgctctc aagaccagag acccaacagc agtgatctca gggcagacag ccctccactc    3565
cagctctgag acccttttct caggacctct gtaggcagca gagagagagg acagaggggt    3625
aagatgaggg gttgagggaa ggttcttcat gatccacact ttgggcttag tatttctcag    3685
gaaagagctat ggcccagaaa caacagggga aactagagtt cggtctgaca gtccttgggg    3745
ttaagtctcc tgtcttatgg tccagaaact cctgtttctc cttagttggc tggaaactgc    3805
tcccatcatt cctctggcc  tctgctgaat gcagggaatg caatccttcc ctgctcttgc    3865
agttgctctg acgtagaaag atccttcggg tgctggaagt ctccatgaag agcttgtgtc    3925
ctgtcctttc ttgcagattc tatttcccct cttctgctaa tacctcttac tttgcttgag    3985
aatcctctcc tttcttatta atttcagtct tggtggttct atcaggggtg cattctggcc    4045
aagggtggg  cctgtgaatc aatcctgggc aatcagacac cctctcctta aaaactggcc    4105
cgtggagact gagatcactg actctgactc atcccacag  ctggctctga caagatggtc    4165
catttgttcc tgcttccgag atccccaggg cagcctggat ccctgccctt ctcaagactt    4225
tagcttttcc ttccatccgg tggcctattc caggaattcc tcttttgctt aaatcagttg    4285
gagtttgtgt ctgttgcttg taatcaagcc tttatggctg ctgggctgag tgacacaagc    4345
actttaatgg cctggaggga cttttaatca gtgaagatgc aatcagacaa gtgttttgga    4405
aagagcaccc tcgagaaggg tggatgacag ggcagagcag gaaggacagg aagctggcag    4465
aacggaggag gctgcagccg tggtccaacc aggagctgat ggcagctggg gctaggggaa    4525
```

```
gggctttgag ggtggaagga tgggatgggt tccagaggta ttcctctctt aaatgcaagt    4585
gcctagatta ggtagacttt gcttagtatt gacaactgca catgaaagtt ttgcaaaggg    4645
aaacaggcta aatgcaccaa gaaagcttct tcagagtgaa gaatcttaat gcttgtaatt    4705
taaacatttg ttcctggagt tttgatttgg tggatgtgat ggttggtttt atttgtcagt    4765
ttggttgggc tatagcacac agttatttaa tcaaacagta atctaggtgt ggctgtgaag    4825
gtattttgta gatgtgatta acatctacaa tcagttgact ttaagtgaaa gagattactt    4885
aaataatttg ggtgagctgc acctgattag ttgaaaggcc tcaagaacaa acactgcagt    4945
ttcctggaaa agaagaaact ttgcctcaag actatagcca tcgactcctg cctgagtttc    5005
cagcctgcta gtctgcccta tggatttgaa gtttgccaac cccaacaatt gtgtgaatta    5065
atttctaaaa ataaagctat atacagcc                                       5093
```

<210> SEQ ID NO 22
<211> LENGTH: 599
<212> TYPE: PRT
<213> ORGANISM: Homo sapien

<400> SEQUENCE: 22

```
Met Ser Arg Ser Leu Leu Leu Trp Phe Leu Leu Phe Leu Leu Leu Leu
 1               5                  10                  15

Pro Pro Leu Pro Val Leu Leu Ala Asp Pro Gly Ala Pro Thr Pro Val
            20                  25                  30

Asn Pro Cys Cys Tyr Tyr Pro Cys Gln His Gln Gly Ile Cys Val Arg
        35                  40                  45

Phe Gly Leu Asp Arg Tyr Gln Cys Asp Cys Thr Arg Thr Gly Tyr Ser
    50                  55                  60

Gly Pro Asn Cys Thr Ile Pro Gly Leu Trp Thr Trp Leu Arg Asn Ser
65                  70                  75                  80

Leu Arg Pro Ser Pro Ser Phe Thr His Phe Leu Thr His Gly Arg
                85                  90                  95

Trp Phe Trp Glu Phe Val Asn Ala Thr Phe Ile Arg Glu Met Leu Met
            100                 105                 110

Arg Leu Val Leu Thr Val Arg Ser Asn Leu Ile Pro Ser Pro Pro Thr
        115                 120                 125

Tyr Asn Ser Ala His Asp Tyr Ile Ser Trp Glu Ser Phe Ser Asn Val
    130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Phe Ala Gln His Phe Thr His Gln Phe
        195                 200                 205

Phe Lys Thr Ser Gly Lys Met Gly Pro Gly Phe Thr Lys Ala Leu Gly
    210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
                245                 250                 255

Asp Gly Glu Met Tyr Pro Pro Ser Val Glu Glu Ala Pro Val Leu Met
            260                 265                 270
```

His Tyr Pro Arg Gly Ile Pro Pro Gln Ser Gln Met Ala Val Gly Gln
            275                 280                 285

Glu Val Phe Gly Leu Leu Pro Gly Leu Met Leu Tyr Ala Thr Leu Trp
        290                 295                 300

Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
                325                 330                 335

Gly Glu Thr Ile Lys Ile Val Ile Glu Glu Tyr Val Gln Gln Leu Ser
            340                 345                 350

Gly Tyr Phe Leu Gln Leu Lys Phe Asp Pro Glu Leu Leu Phe Gly Val
        355                 360                 365

Gln Phe Gln Tyr Arg Asn Arg Ile Ala Met Glu Phe Asn His Leu Tyr
    370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
                405                 410                 415

Gly Val Glu Ala Leu Val Asp Ala Phe Ser Arg Gln Ile Ala Gly Arg
            420                 425                 430

Ile Gly Gly Gly Arg Asn Met Asp His His Ile Leu His Val Ala Val
        435                 440                 445

Asp Val Ile Arg Glu Ser Arg Glu Met Arg Leu Gln Pro Phe Asn Glu
    450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Leu Tyr Gly Asp
                485                 490                 495

Ile Asp Ala Leu Glu Phe Tyr Pro Gly Leu Leu Leu Glu Lys Cys His
            500                 505                 510

Pro Asn Ser Ile Phe Gly Glu Ser Met Ile Glu Ile Gly Ala Pro Phe
        515                 520                 525

Ser Leu Lys Gly Leu Leu Gly Asn Pro Ile Cys Ser Pro Glu Tyr Trp
    530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
                565                 570                 575

Val Ser Phe Arg Val Pro Asp Ala Ser Gln Asp Asp Gly Pro Ala Val
            580                 585                 590

Glu Arg Pro Ser Thr Glu Leu
        595

<210> SEQ ID NO 23
<211> LENGTH: 4982
<212> TYPE: DNA
<213> ORGANISM: Homo sapien
<220> FEATURE:
<221> NAME/KEY: CDS
<222> LOCATION: (136)...(1824)

<400> SEQUENCE: 23
aggtgacagc tggagggagg agcgggggtg gagccggggg aagggtgggg aggggatggg      60
ctggagctcc gggcagtgtg cgaggcgcac gcacaggagc ctgcactctg cgtcccgcac    120

-continued

| | |
|---|---|
| cccagcagcc gcgcc atg agc cgg agt ctc ttg ctc tgg ttc ttg ctg ttc<br>                   Met Ser Arg Ser Leu Leu Leu Trp Phe Leu Leu Phe<br>                    1             5                   10 | 171 |
| ctg ctc ctg ctc ccg ccg ctc ccc gtc ctg ctc gcg gac cca ggg gcg<br>Leu Leu Leu Leu Pro Pro Leu Pro Val Leu Leu Ala Asp Pro Gly Ala<br>            15                   20                   25 | 219 |
| ccc acg cca gtg aat ccc tgt tgt tac tat cca tgc cag cac cag ggc<br>Pro Thr Pro Val Asn Pro Cys Cys Tyr Tyr Pro Cys Gln His Gln Gly<br>    30                   35                   40 | 267 |
| atc tgt gtc cgc ttc ggc ctt gac cgc tac cag tgt gac tgc acc cgc<br>Ile Cys Val Arg Phe Gly Leu Asp Arg Tyr Gln Cys Asp Cys Thr Arg<br>45                 50                   55                   60 | 315 |
| acg ggc tat tcc ggc ccc aac tgc acc atc cct ggc ctg tgg acc tgg<br>Thr Gly Tyr Ser Gly Pro Asn Cys Thr Ile Pro Gly Leu Trp Thr Trp<br>                65                   70                   75 | 363 |
| ctc cgg aat tca ctg cgg ccc agc ccc tct ttc acc cac ttc ctg ctc<br>Leu Arg Asn Ser Leu Arg Pro Ser Pro Ser Phe Thr His Phe Leu Leu<br>            80                   85                   90 | 411 |
| act cac ggg cgc tgg ttc tgg gag ttt gtc aat gcc acc ttc atc cga<br>Thr His Gly Arg Trp Phe Trp Glu Phe Val Asn Ala Thr Phe Ile Arg<br>               95                 100               105 | 459 |
| gag atg ctc atg cgc ctg gta ctc aca gtg cgc tcc aac ctt atc ccc<br>Glu Met Leu Met Arg Leu Val Leu Thr Val Arg Ser Asn Leu Ile Pro<br>110                   115                  120 | 507 |
| agt ccc ccc acc tac aac tca gca cat gac tac atc agc tgg gag tct<br>Ser Pro Pro Thr Tyr Asn Ser Ala His Asp Tyr Ile Ser Trp Glu Ser<br>125                   130                  135             140 | 555 |
| ttc tcc aac gtg agc tat tac act cgt att ctg ccc tct gtg cct aaa<br>Phe Ser Asn Val Ser Tyr Tyr Thr Arg Ile Leu Pro Ser Val Pro Lys<br>                 145                  150                155 | 603 |
| gat tgc ccc aca ccc atg gga acc aaa ggg aag aag cag ttg cca gat<br>Asp Cys Pro Thr Pro Met Gly Thr Lys Gly Lys Lys Gln Leu Pro Asp<br>                    160                 165                170 | 651 |
| gcc cag ctc ctg gcc cgc cgc ttc ctg ctc agg agg aag ttc ata cct<br>Ala Gln Leu Leu Ala Arg Arg Phe Leu Leu Arg Arg Lys Phe Ile Pro<br>175                   180                  185 | 699 |
| gac ccc caa ggc acc aac ctc atg ttt gcc ttc ttt gca caa cac ttc<br>Asp Pro Gln Gly Thr Asn Leu Met Phe Ala Phe Phe Ala Gln His Phe<br>            190                  195               200 | 747 |
| acc cac cag ttc ttc aaa act tct ggc aag atg ggt cct ggc ttc acc<br>Thr His Gln Phe Phe Lys Thr Ser Gly Lys Met Gly Pro Gly Phe Thr<br>205                   210                  215               220 | 795 |
| aag gcc ttg ggc cat ggg gta gac ctc ggc cac att tat gga gac aat<br>Lys Ala Leu Gly His Gly Val Asp Leu Gly His Ile Tyr Gly Asp Asn<br>                    225                 230                235 | 843 |
| ctg gag cgt cag tat caa ctg cgg ctc ttt aag gat ggg aaa ctc aag<br>Leu Glu Arg Gln Tyr Gln Leu Arg Leu Phe Lys Asp Gly Lys Leu Lys<br>                240                 245                250 | 891 |
| tac cag gtg ctg gat gga gaa atg tac ccg ccc tcg gta gaa gag gcg<br>Tyr Gln Val Leu Asp Gly Glu Met Tyr Pro Pro Ser Val Glu Glu Ala<br>            255                  260               265 | 939 |
| cct gtg ttg atg cac tac ccc cga ggc atc ccg ccc cag agc cag atg<br>Pro Val Leu Met His Tyr Pro Arg Gly Ile Pro Pro Gln Ser Gln Met<br>270                   275                  280 | 987 |
| gct gtg ggc cag gag gtg ttt ggg ctg ctt cct ggg ctc atg ctg tat<br>Ala Val Gly Gln Glu Val Phe Gly Leu Leu Pro Gly Leu Met Leu Tyr<br>285                   290                  295               300 | 1035 |
| gcc acg ctc tgg cta cgt gag cac aac cgt gtg tgt gac ctg ctg aag<br>Ala Thr Leu Trp Leu Arg Glu His Asn Arg Val Cys Asp Leu Leu Lys<br>                305                 310                315 | 1083 |

```
gct gag cac ccc acc tgg ggc gat gag cag ctt ttc cag acg acc cgc      1131
Ala Glu His Pro Thr Trp Gly Asp Glu Gln Leu Phe Gln Thr Thr Arg
            320                 325                 330 ctc atc ctc ata ggg gag acc atc aag att gtc atc gag gag tac gtg      1179
Leu Ile Leu Ile Gly Glu Thr Ile Lys Ile Val Ile Glu Glu Tyr Val
            335                 340                 345 cag cag ctg agt ggc tat ttc ctg cag ctg aaa ttt gac cca gag ctg      1227
Gln Gln Leu Ser Gly Tyr Phe Leu Gln Leu Lys Phe Asp Pro Glu Leu
        350                 355                 360 ctg ttc ggt gtc cag ttc caa tac cgc aac cgc att gcc atg gag ttc      1275
Leu Phe Gly Val Gln Phe Gln Tyr Arg Asn Arg Ile Ala Met Glu Phe
365                 370                 375                 380 aac cat ctc tac cac tgg cac ccc ctc atg cct gac tcc ttc aag atc      1323
Asn His Leu Tyr His Trp His Pro Leu Met Pro Asp Ser Phe Lys Ile
            385                 390                 395 ggt ggg ggc agg aac atg gac cac cac atc ctg cat gtg gct gtg gat      1371
Gly Gly Gly Arg Asn Met Asp His His Ile Leu His Val Ala Val Asp
            400                 405                 410 gtc atc agg gag tct cgg gag atg cgg ctg cag ccc ttc aat gag tac      1419
Val Ile Arg Glu Ser Arg Glu Met Arg Leu Gln Pro Phe Asn Glu Tyr
        415                 420                 425 cgc aag agg ttt ggc atg aaa ccc tac acc tcc ttc cag gag ctc gta      1467
Arg Lys Arg Phe Gly Met Lys Pro Tyr Thr Ser Phe Gln Glu Leu Val
430                 435                 440 gga gag aag gag atg gca gca gag ttg gag gaa ttg tat gga gac att      1515
Gly Glu Lys Glu Met Ala Ala Glu Leu Glu Glu Leu Tyr Gly Asp Ile
445                 450                 455                 460 gat gcg ttg gag ttc tac cct gga ctg ctt ctt gaa aag tgc cat cca      1563
Asp Ala Leu Glu Phe Tyr Pro Gly Leu Leu Leu Glu Lys Cys His Pro
            465                 470                 475 aac tct atc ttt ggg gag agt atg ata gag att ggg gct ccc ttt tcc      1611
Asn Ser Ile Phe Gly Glu Ser Met Ile Glu Ile Gly Ala Pro Phe Ser
            480                 485                 490 ctc aag ggt ctc cta ggg aat ccc atc tgt tct ccg gag tac tgg aag      1659
Leu Lys Gly Leu Leu Gly Asn Pro Ile Cys Ser Pro Glu Tyr Trp Lys
        495                 500                 505 ccg agc aca ttt ggc ggc gag gtg ggc ttt aac att gtc aag acg gcc      1707
Pro Ser Thr Phe Gly Gly Glu Val Gly Phe Asn Ile Val Lys Thr Ala
510                 515                 520 aca ctg aag aag ctg gtc tgc ctc aac acc aag acc tgt ccc tac gtt      1755
Thr Leu Lys Lys Leu Val Cys Leu Asn Thr Lys Thr Cys Pro Tyr Val
525                 530                 535                 540 tcc ttc cgt gtg ccg gat gcc agt cag gat gat ggg cct gct gtg gag      1803
Ser Phe Arg Val Pro Asp Ala Ser Gln Asp Asp Gly Pro Ala Val Glu
            545                 550                 555 cga cca tcc aca gag ctc tga ggggcaggaa agcagcattc tggaggggag         1854
Arg Pro Ser Thr Glu Leu  *
            560 agctttgtgc ttgtcattcc agagtgctga ggccagggct gatggtctta aatgctcatt     1914 ttctggtttg gcatggtgag tgttggggtt gacatttaga actttaagtc tcacccatta     1974 tctggaatat tgtgattctg tttattcttc cagaatgctg aactccttgt tagcccttca     2034 gattgttagg agtggttctc atttggtctg ccagaatact gggttcttag ttgacaacct     2094 agaatgtcag atttctggtt gatttgtaac acagtcattc taggatgtgg agctactgat     2154 gaaatctgct agaaagttag ggggttctta ttttgcattc cagaatcctg actttctgat     2214 tggtgattca aagtgttgtg ttcctggctg atgatccaga acagtggctc gtatcccaaa     2274
```

```
tctgtcagca tctggctgtc tagaatgtgg atttgattca ttttcctgtt cagtgagata    2334
tcatagagac ggagatccta aggtccaaca agaatgcatt ccctgaatct gtgcctgcac    2394
tgagagggca aggaagtggg gtgttcttct tgggaccccc actaagaccc tggtctgagg    2454
atgtagagag aacaggtggg ctgtattcac gccattggtt ggaagctacc agagctctat    2514
ccccatccag gtcttgactc atggcagctg tttctcatga agctaataaa attcgctttc    2574
taaagttacc tgttatatat ctcttttggt cccatcctct aaagcagagg caacactgga    2634
acatggctag cctttcttgt agccatggct gggcgtgcta gaggttgcag catgagactt    2694
tctgctggga tccttgggcc catcactgta tagacatgct accactggta cttcctttct    2754
ccctgcgggc caggcactgc ccttttcagg aagctctctt aaaataccca ttgccccaga    2814
cctggaagat ataacattca gttcccacca tctgattaaa acaacttcct cccttacaga    2874
gcatacaaca gagggggcac ccggggagga gagcacatac tgtgttccaa tttcacgctt    2934
ttaattctca tttgttctca caccaacagt gtgaagtgcg tggtataatc tccatttcaa    2994
aaccaaggaa gcagcctcag agtggtcgag tgacacacct cacgcaggct gagtccagag    3054
cttgtgctcc tcttgattcc tggtttgact cagttccagg cctgatcttg cctgtctggc    3114
tcagggtcaa agacagaatg gtggagtgta gcctccacct gatattcagg ctactcattc    3174
agtcccaaat atgtattttc ctaagtgttt actatgtgcc agttcctgta acaggtgtgg    3234
ggacacagca gtgagtaatc aatacagaca aggttctgcc cttatggagc tcacactcca    3294
gtggcagaca aacagaccat aaataaggaa acgatgaaat aagatatata caaggtgagt    3354
gtgacttccc ttctaacccc ctctgctctg tcctccccta ttgcgctctc aagaccagag    3414
acccaacagc agtgatctca gggcagacag ccctccactc cagctctgag acccttttct    3474
caggacctct gtaggcagca gagagagagg acagaggggt aagatgaggg gttgagggaa    3534
ggttcttcat gatccacact ttgggcttag tatttctcag gaagagctat ggcccagaaa    3594
caacagggga aactagagtt cggtctgaca gtccttgggg ttaagtctcc tgtcttatgg    3654
tccagaaact cctgtttctc cttagttggc tggaaactgc tcccatcatt ccttctggcc    3714
tctgctgaat gcagggaatg caatccttcc ctgctcttgc agttgctctg acgtagaaag    3774
atccttcggg tgctggaagt ctccatgaag agcttgtgtc ctgtcctttc ttgcagattc    3834
tatttcccct cttctgctaa tacctcttac tttgcttgag aatcctctcc tttcttatta    3894
atttcagtct tggtggttct atcagggggtg cattctggcc aagggtgggg cctgtgaatc    3954
aatcctgggc aatcagacac cctctcctta aaaactggcc cgtggagact gagatcactg    4014
actctgactc atccccacag ctggctctga caagatggtc catttgttcc tgcttccgag    4074
atccccaggg cagcctggat ccctgccctt ctcaagactt tagcttttcc ttccatccgg    4134
tggcctattc caggaattcc tcttttgctt aaatcagttg gagtttgtgt ctgttgcttg    4194
taatcaagcc tttatggctg ctgggctgag tgacacaagc actttaatgg cctggaggga    4254
cttttaatca gtgaagatgc aatcagacaa gtgttttgga aagagcaccc tcgagaaggg    4314
tggatgacag ggcagagcag gaaggacagg aagctggcag aacggaggag gctgcagccg    4374
tggtccaacc aggagctgat ggcagctggg gctagggaa gggctttgag ggtggaagga    4434
tgggatgggt tccagaggta ttcctctctt aaatgcaagt gcctagatta ggtagacttt    4494
gcttagtatt gacaactgca catgaaagtt ttgcaaaggg aaacaggcta aatgcaccaa    4554
gaaagcttct tcagagtgaa gaatcttaat gcttgtaatt taaacatttg ttcctggagt    4614
tttgatttgg tggatgtgat ggttggtttt atttgtcagt ttggttgggc tatagcacac    4674
```

```
agttatttaa tcaaacagta atctaggtgt ggctgtgaag gtattttgta gatgtgatta    4734
acatctacaa tcagttgact ttaagtgaaa gagattactt aaataatttg ggtgagctgc    4794
acctgattag ttgaaaggcc tcaagaacaa acactgcagt ttcctggaaa agaagaaact    4854
ttgcctcaag actatagcca tcgactcctg cctgagtttc cagcctgcta gtctgccctg    4914
tggatttgaa gtttgccaac cccaacaatt gtgtgaatta atttctaaaa ataaagctat    4974
atacagcc                                                             4982

<210> SEQ ID NO 24
<211> LENGTH: 562
<212> TYPE: PRT
<213> ORGANISM: Homo sapien

<400> SEQUENCE: 24
```

| Met | Ser | Arg | Ser | Leu | Leu | Leu | Trp | Phe | Leu | Leu | Phe | Leu | Leu | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Pro | Pro | Leu | Pro | Val | Leu | Leu | Ala | Asp | Pro | Gly | Ala | Pro | Thr | Pro | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Pro | Cys | Cys | Tyr | Tyr | Pro | Cys | Gln | His | Gln | Gly | Ile | Cys | Val | Arg |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Phe | Gly | Leu | Asp | Arg | Tyr | Gln | Cys | Asp | Cys | Thr | Arg | Thr | Gly | Tyr | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Pro | Asn | Cys | Thr | Ile | Pro | Gly | Leu | Trp | Thr | Trp | Leu | Arg | Asn | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Arg | Pro | Ser | Pro | Ser | Phe | Thr | His | Phe | Leu | Leu | Thr | His | Gly | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Trp | Phe | Trp | Glu | Phe | Val | Asn | Ala | Thr | Phe | Ile | Arg | Glu | Met | Leu | Met |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Leu | Val | Leu | Thr | Val | Arg | Ser | Asn | Leu | Ile | Pro | Ser | Pro | Pro | Thr |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Tyr | Asn | Ser | Ala | His | Asp | Tyr | Ile | Ser | Trp | Glu | Ser | Phe | Ser | Asn | Val |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Tyr | Tyr | Thr | Arg | Ile | Leu | Pro | Ser | Val | Pro | Lys | Asp | Cys | Pro | Thr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Pro | Met | Gly | Thr | Lys | Gly | Lys | Lys | Gln | Leu | Pro | Asp | Ala | Gln | Leu | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Arg | Arg | Phe | Leu | Leu | Arg | Arg | Lys | Phe | Ile | Pro | Asp | Pro | Gln | Gly |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Thr | Asn | Leu | Met | Phe | Ala | Phe | Phe | Ala | Gln | His | Phe | Thr | His | Gln | Phe |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Phe | Lys | Thr | Ser | Gly | Lys | Met | Gly | Pro | Gly | Phe | Thr | Lys | Ala | Leu | Gly |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| His | Gly | Val | Asp | Leu | Gly | His | Ile | Tyr | Gly | Asp | Asn | Leu | Glu | Arg | Gln |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Tyr | Gln | Leu | Arg | Leu | Phe | Lys | Asp | Gly | Lys | Leu | Lys | Tyr | Gln | Val | Leu |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Asp | Gly | Glu | Met | Tyr | Pro | Pro | Ser | Val | Glu | Glu | Ala | Pro | Val | Leu | Met |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| His | Tyr | Pro | Arg | Gly | Ile | Pro | Pro | Gln | Ser | Gln | Met | Ala | Val | Gly | Gln |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Glu | Val | Phe | Gly | Leu | Leu | Pro | Gly | Leu | Met | Leu | Tyr | Ala | Thr | Leu | Trp |
|-----|-----|-----|-----|-----|-----|-----|-----|-----|-----|-----|-----|-----|-----|-----|-----|
|     |     | 290 |     |     |     |     | 295 |     |     |     |     | 300 |     |     |     |

| Leu | Arg | Glu | His | Asn | Arg | Val | Cys | Asp | Leu | Leu | Lys | Ala | Glu | His | Pro |
|-----|-----|-----|-----|-----|-----|-----|-----|-----|-----|-----|-----|-----|-----|-----|-----|

```
                305                 310                 315                 320
Thr Trp Gly Asp Glu Gln Leu Phe Gln Thr Thr Arg Leu Ile Leu Ile
                    325                 330                 335

Gly Glu Thr Ile Lys Ile Val Ile Glu Glu Tyr Val Gln Gln Leu Ser
                340                 345                 350

Gly Tyr Phe Leu Gln Leu Lys Phe Asp Pro Glu Leu Leu Phe Gly Val
            355                 360                 365

Gln Phe Gln Tyr Arg Asn Arg Ile Ala Met Glu Phe Asn His Leu Tyr
        370                 375                 380

His Trp His Pro Leu Met Pro Asp Ser Phe Lys Ile Gly Gly Gly Arg
385                 390                 395                 400

Asn Met Asp His His Ile Leu His Val Ala Val Asp Val Ile Arg Glu
                405                 410                 415

Ser Arg Glu Met Arg Leu Gln Pro Phe Asn Glu Tyr Arg Lys Arg Phe
            420                 425                 430

Gly Met Lys Pro Tyr Thr Ser Phe Gln Glu Leu Val Gly Glu Lys Glu
        435                 440                 445

Met Ala Ala Glu Leu Glu Glu Leu Tyr Gly Asp Ile Asp Ala Leu Glu
    450                 455                 460

Phe Tyr Pro Gly Leu Leu Leu Glu Lys Cys His Pro Asn Ser Ile Phe
465                 470                 475                 480

Gly Glu Ser Met Ile Glu Ile Gly Ala Pro Phe Ser Leu Lys Gly Leu
                485                 490                 495

Leu Gly Asn Pro Ile Cys Ser Pro Glu Tyr Trp Lys Pro Ser Thr Phe
            500                 505                 510

Gly Gly Glu Val Gly Phe Asn Ile Val Lys Thr Ala Thr Leu Lys Lys
        515                 520                 525

Leu Val Cys Leu Asn Thr Lys Thr Cys Pro Tyr Val Ser Phe Arg Val
    530                 535                 540

Pro Asp Ala Ser Gln Asp Asp Gly Pro Ala Val Glu Arg Pro Ser Thr
545                 550                 555                 560

Glu Leu

<210> SEQ ID NO 25
<211> LENGTH: 607
<212> TYPE: DNA
<213> ORGANISM: Homo sapien
<220> FEATURE:
<221> NAME/KEY: CDS
<222> LOCATION: (114)...(398)

<400> SEQUENCE: 25
ggactgttga agacaggtct ccacacacag ctccagcagc cacatttgca accttggcca      60
tctgtccaga acctgctccc acctcaggcc caggccaacc gtgcactgct gca atg       116
                                                          Met
                                                          1 ggc tct gag ctg gag acg gcg atg gag acc ctc atc aac gtg ttc cac      164
Gly Ser Glu Leu Glu Thr Ala Met Glu Thr Leu Ile Asn Val Phe His
            5                   10                  15 gcc cac tcg ggc aaa gag ggg gac aag tac aag ctg agc aag aag gag      212
Ala His Ser Gly Lys Glu Gly Asp Lys Tyr Lys Leu Ser Lys Lys Glu
        20                  25                  30 ctg aaa gag ctg ctg cag acg gag ctc tct ggc ttc ctg gat gcc cag      260
Leu Lys Glu Leu Leu Gln Thr Glu Leu Ser Gly Phe Leu Asp Ala Gln
    35                  40                  45 aag gat gtg gat gct gtg gac aag gtg atg aag gag cta gac gag aat      308
Lys Asp Val Asp Ala Val Asp Lys Val Met Lys Glu Leu Asp Glu Asn
```

-continued

```
Lys Asp Val Asp Ala Val Asp Lys Val Met Lys Glu Leu Asp Glu Asn
 50                  55                  60                  65 gga gac ggg gag gtg gac ttc cag gag tat gtg gtg ctt gtg gct gct       356
Gly Asp Gly Glu Val Asp Phe Gln Glu Tyr Val Val Leu Val Ala Ala
                 70                  75                  80 ctc aca gtg gcc tgt aac aat ttc ttc tgg gag aac agt tga              398
Leu Thr Val Ala Cys Asn Asn Phe Phe Trp Glu Asn Ser  *
             85                  90 gcagacagcc acattgggca gcgcccttcc tctccaccct cccagacctg cctcttcccc      458
ctgcttccac ctcaccccac ttatccctct ccataacccc accccttgccc accccacccc     518 cacccccacc aagggcgcaa gagtagcggt ccaagcctgc aactcatctt tcattaaagg      578
cttctctctc accagcaaaa aaaaaaaaa                                        607

<210> SEQ ID NO 26
<211> LENGTH: 94
<212> TYPE: PRT
<213> ORGANISM: Homo sapien

<400> SEQUENCE: 26

Met Gly Ser Glu Leu Glu Thr Ala Met Glu Thr Leu Ile Asn Val Phe
 1               5                  10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
             35                  40                  45

Gln Lys Asp Val Asp Ala Val Asp Lys Val Met Lys Glu Leu Asp Glu
         50                  55                  60

Asn Gly Asp Gly Glu Val Asp Phe Gln Glu Tyr Val Val Leu Val Ala
 65                  70                  75                  80

Ala Leu Thr Val Ala Cys Asn Asn Phe Phe Trp Glu Asn Ser
                 85                  90

<210> SEQ ID NO 27
<211> LENGTH: 517
<212> TYPE: DNA
<213> ORGANISM: Homo sapien
<220> FEATURE:
<221> NAME/KEY: CDS
<222> LOCATION: (65)...(352)

<400> SEQUENCE: 27
cctccacagc aacttccttg atccctgcca cgcacgactg aacacagaca gcagccgcct      60 cgcc atg aag ctg ctg atg gtc ctc atg ctg gcg gcc ctc ctc ctg cac     109
     Met Lys Leu Leu Met Val Leu Met Leu Ala Ala Leu Leu Leu His
      1               5                  10                  15 tgc tat gca gat tct ggc tgc aaa ctc ctg gag gac atg gtt gaa aag     157
Cys Tyr Ala Asp Ser Gly Cys Lys Leu Leu Glu Asp Met Val Glu Lys
                 20                  25                  30 acc atc aat tcc gac ata tct ata cct gaa tac aaa gag ctt ctt caa     205
Thr Ile Asn Ser Asp Ile Ser Ile Pro Glu Tyr Lys Glu Leu Leu Gln
             35                  40                  45 gag ttc ata gac agt gat gcc gct gca gag gct atg ggg aaa ttc aag     253
Glu Phe Ile Asp Ser Asp Ala Ala Ala Glu Ala Met Gly Lys Phe Lys
         50                  55                  60 cag tgt ttc ctc aac cag tca cat aga act ctg aaa aac ttt gga ctg     301
Gln Cys Phe Leu Asn Gln Ser His Arg Thr Leu Lys Asn Phe Gly Leu
 65                  70                  75 atg atg cat aca gtg tac gac agc att tgg tgt aat atg aag agt aat     349
```

```
Met Met His Thr Val Tyr Asp Ser Ile Trp Cys Asn Met Lys Ser Asn
 80              85                  90                  95 taa ctttacccaa ggcgtttggc tcagagggct acagactatg ccagaactc        402
 * atctgttgat tgctagaaac cactttttctt tcttgtgttg tcttttatg tggaaactgc 462 tagacaactg ttgaaacctc aaattcattt ccatttcaat aactaactgc aaatc     517
```

```
<210> SEQ ID NO 28
<211> LENGTH: 95
<212> TYPE: PRT
<213> ORGANISM: Homo sapien

<400> SEQUENCE: 28

Met Lys Leu Leu Met Val Leu Met Leu Ala Ala Leu Leu His Cys
 1               5                  10                  15

Tyr Ala Asp Ser Gly Cys Lys Leu Leu Glu Asp Met Val Glu Lys Thr
                 20                  25                  30

Ile Asn Ser Asp Ile Ser Ile Pro Glu Tyr Lys Glu Leu Leu Gln Glu
             35                  40                  45

Phe Ile Asp Ser Asp Ala Ala Glu Ala Met Gly Lys Phe Lys Gln
 50                  55                  60

Cys Phe Leu Asn Gln Ser His Arg Thr Leu Lys Asn Phe Gly Leu Met
 65                  70                  75                  80

Met His Thr Val Tyr Asp Ser Ile Trp Cys Asn Met Lys Ser Asn
                 85                  90                  95
```

```
<210> SEQ ID NO 29
<211> LENGTH: 2192
<212> TYPE: DNA
<213> ORGANISM: Homo sapien
<220> FEATURE:
<221> NAME/KEY: CDS
<222> LOCATION: (101)...(2044)

<400> SEQUENCE: 29
agtctggccc tggacaaccc cagcaaagcc gccctcagcc agcccagaag cactgggcct    60
tggccacagc aacacccact gagcacgctg ggagctgagt atg gcg tcc ctg gtc    115
                                             Met Ala Ser Leu Val
                                              1               5 tcg ctg gag ctg ggg ctg ctt ctg gct gtg ctg gtg gtg acg gcg acg    163
Ser Leu Glu Leu Gly Leu Leu Leu Ala Val Leu Val Val Thr Ala Thr
                10                  15                  20 gcg tcc ccg cct gct ggt ctg ctg agc ctg ctc acc tct ggc cag ggc    211
Ala Ser Pro Pro Ala Gly Leu Leu Ser Leu Leu Thr Ser Gly Gln Gly
         25                  30                  35 gct ctg gat caa gag gct ctg ggc ggc ctg tta aat acg ctg gcg gac    259
Ala Leu Asp Gln Glu Ala Leu Gly Gly Leu Leu Asn Thr Leu Ala Asp
     40                  45                  50 cgt gtg cac tgc acc aac ggg ccg tgt gga aag tgc ctg tct gtg gag    307
Arg Val His Cys Thr Asn Gly Pro Cys Gly Lys Cys Leu Ser Val Glu
 55                  60                  65 gac gcc ctg ggc ctg ggc gag cct gag ggg tca ggg ctg ccc ccg ggc    355
Asp Ala Leu Gly Leu Gly Glu Pro Glu Gly Ser Gly Leu Pro Pro Gly
 70                  75                  80                  85 ccg gtc ctg gag gcc agg tac gtc gcc cgc ctc agt gcc gcc gcc gtc    403
Pro Val Leu Glu Ala Arg Tyr Val Ala Arg Leu Ser Ala Ala Ala Val
                 90                  95                 100 ctg tac ctc agc aac ccc gag ggc acc tgt gag gac act cgg gct ggc    451
Leu Tyr Leu Ser Asn Pro Glu Gly Thr Cys Glu Asp Thr Arg Ala Gly
```

-continued

```
             105                 110                 115
ctc tgg gcc tct cat gca gac cac ctc ctg gcc ctg ctc gag agc ccc     499
Leu Trp Ala Ser His Ala Asp His Leu Leu Ala Leu Leu Glu Ser Pro
        120                 125                 130 aag gcc ctg acc ccg ggc ctg agc tgg ctg ctg cag agg atg cag gcc     547
Lys Ala Leu Thr Pro Gly Leu Ser Trp Leu Leu Gln Arg Met Gln Ala
135                 140                 145 cgg gct gcc ggc cag acc ccc aag acg gcc tgc gta gat atc cct cag     595
Arg Ala Ala Gly Gln Thr Pro Lys Thr Ala Cys Val Asp Ile Pro Gln
150                 155                 160                 165 ctg ctg gag gag gcg gtg ggg gcg ggg gct ccg ggc agt gct ggc ggc     643
Leu Leu Glu Glu Ala Val Gly Ala Gly Ala Pro Gly Ser Ala Gly Gly
                170                 175                 180 gtc ctg gct gcc ctg ctg gac cat gtc agg agc ggg tct tgc ttc cac     691
Val Leu Ala Ala Leu Leu Asp His Val Arg Ser Gly Ser Cys Phe His
                185                 190                 195 gcc ttg ccg agc cct cag tac ttc gtg gac ttt gtg ttc cag cag cac     739
Ala Leu Pro Ser Pro Gln Tyr Phe Val Asp Phe Val Phe Gln Gln His
                200                 205                 210 agc agc gag gtc cct atg acg ctg gcc gag ctg tca gcc ttg atg cag     787
Ser Ser Glu Val Pro Met Thr Leu Ala Glu Leu Ser Ala Leu Met Gln
        215                 220                 225 cgc ctg ggg gtg ggc agg gag gcc cac agt gac cac agt cat cgg cac     835
Arg Leu Gly Val Gly Arg Glu Ala His Ser Asp His Ser His Arg His
230                 235                 240                 245 agg gga gcc agc agc cgg gac cct gtg ccc ctc atc agc tcc agc aac     883
Arg Gly Ala Ser Ser Arg Asp Pro Val Pro Leu Ile Ser Ser Ser Asn
                250                 255                 260 agc tcc agt gtg tgg gac acg gta tgc ctg agt gcc agg gac gtg atg     931
Ser Ser Ser Val Trp Asp Thr Val Cys Leu Ser Ala Arg Asp Val Met
                265                 270                 275 gct gca tat gga ctg tcg gaa cag gct ggg gtg acc ccg gag gcc tgg     979
Ala Ala Tyr Gly Leu Ser Glu Gln Ala Gly Val Thr Pro Glu Ala Trp
                280                 285                 290 gcc caa ctg agc cct gcc ctg ctc caa cag cag ctg agt gga gcc tgc    1027
Ala Gln Leu Ser Pro Ala Leu Leu Gln Gln Gln Leu Ser Gly Ala Cys
        295                 300                 305 acc tcc cag tcc agg ccc ccc gtc cag gac cag ctc agc cag tca gag    1075
Thr Ser Gln Ser Arg Pro Pro Val Gln Asp Gln Leu Ser Gln Ser Glu
310                 315                 320                 325 agg tat ctg tac ggc tcc ctg gcc acg ctg ctc atc tgc ctc tgc gcg    1123
Arg Tyr Leu Tyr Gly Ser Leu Ala Thr Leu Leu Ile Cys Leu Cys Ala
                330                 335                 340 gtc ttt ggc ctc ctg ctg acc tgc act ggc tgc agg ggg gtc gcc    1171
Val Phe Gly Leu Leu Leu Thr Cys Thr Gly Cys Arg Gly Val Ala
                345                 350                 355 cac tac atc ctg cag acc ttc ctg agc ctg gca gtg ggt gca ctc act    1219
His Tyr Ile Leu Gln Thr Phe Leu Ser Leu Ala Val Gly Ala Leu Thr
                360                 365                 370 ggg gac gct gtc ctg cat ctg acg ccc aag gtg ctg ggg ctg cat aca    1267
Gly Asp Ala Val Leu His Leu Thr Pro Lys Val Leu Gly Leu His Thr
                375                 380                 385 cac agc gaa gag ggc ctc agc cca cag ccc acc tgg cgc ctc ctg gct    1315
His Ser Glu Glu Gly Leu Ser Pro Gln Pro Thr Trp Arg Leu Leu Ala
390                 395                 400                 405 atg ctg gcc ggg ctc tac gcc ttc ttc ctg ttt gag aac ctc ttc aat    1363
Met Leu Ala Gly Leu Tyr Ala Phe Phe Leu Phe Glu Asn Leu Phe Asn
                410                 415                 420 ctc ctg ctg ccc agg gac ccg gag gac ctg gag gac ggg ccc tgc ggc    1411
```

```
                    Leu Leu Leu Pro Arg Asp Pro Glu Asp Leu Glu Asp Gly Pro Cys Gly
                                425                 430                 435 cac agc agc cat agc cac ggg ggc cac agc cac ggt gtg tcc ctg cag           1459
His Ser Ser His Ser His Gly Gly His Ser His Gly Val Ser Leu Gln
            440                 445                 450 ctg gca ccc agc gag ctc cgg cag ccc aag ccc ccc cac gag ggc tcc           1507
Leu Ala Pro Ser Glu Leu Arg Gln Pro Lys Pro Pro His Glu Gly Ser
455                 460                 465 cgc gca gac ctg gtg gcg gag gag agc ccg gag ctg ctg aac cct gag           1555
Arg Ala Asp Leu Val Ala Glu Glu Ser Pro Glu Leu Leu Asn Pro Glu
470                 475                 480                 485 ccc agg aga ctg agc cca gag ttg agg cta ctg ccc tat atg atc act           1603
Pro Arg Arg Leu Ser Pro Glu Leu Arg Leu Leu Pro Tyr Met Ile Thr
                490                 495                 500 ctg ggc gac gcc gtg cac aac ttc gcc gac ggg ctg gcc gtg ggc gcc           1651
Leu Gly Asp Ala Val His Asn Phe Ala Asp Gly Leu Ala Val Gly Ala
                505                 510                 515 gcc ttc gcg tcc tcc tgg aag acc ggg ctg gcc acc tcg ctg gcc gtg           1699
Ala Phe Ala Ser Ser Trp Lys Thr Gly Leu Ala Thr Ser Leu Ala Val
            520                 525                 530 ttc tgc cac gag ttg cca cac gag ctg ggg gac ttc gcc gcc ttg ctg           1747
Phe Cys His Glu Leu Pro His Glu Leu Gly Asp Phe Ala Ala Leu Leu
535                 540                 545 cac gcg ggg ctg tcc gtg cgc caa gca ctg ctg ctg aac ctg gcc tcc           1795
His Ala Gly Leu Ser Val Arg Gln Ala Leu Leu Leu Asn Leu Ala Ser
550                 555                 560                 565 gcg ctc acg gcc ttc gct ggt ctc tac gtg gca ctc gcg gtt gga gtc           1843
Ala Leu Thr Ala Phe Ala Gly Leu Tyr Val Ala Leu Ala Val Gly Val
                570                 575                 580 agc gag gag agc gag gcc tgg atc ctg gca gtg gcc acc ggc ctg ttc           1891
Ser Glu Glu Ser Glu Ala Trp Ile Leu Ala Val Ala Thr Gly Leu Phe
                585                 590                 595 ctc tac gta gca ctc tgc gac atg ctc ccg gcg atg ttg aaa gta cgg           1939
Leu Tyr Val Ala Leu Cys Asp Met Leu Pro Ala Met Leu Lys Val Arg
            600                 605                 610 gac ccg cgg ccc tgg ctc ctc ttc ctg ctg cac aac gtg ggc ctg ctg           1987
Asp Pro Arg Pro Trp Leu Leu Phe Leu Leu His Asn Val Gly Leu Leu
615                 620                 625 ggc ggc tgg acc gtc ctg ctg ctg ctg tcc ctg tac gag gat gac atc           2035
Gly Gly Trp Thr Val Leu Leu Leu Leu Ser Leu Tyr Glu Asp Asp Ile
630                 635                 640                 645 acc ttc tga taccctgccc tagtccccca cctttgactt aagatcccac                   2084
Thr Phe * acctcacaaa cctacagccc agaaaccaga agcccctata gaggcccag tcccaactcc          2144 agtaaagaca ctcttgtcct tggaaaaaaa aaaaaaaaaa aaaaaaaa                      2192

<210> SEQ ID NO 30
<211> LENGTH: 647
<212> TYPE: PRT
<213> ORGANISM: Homo sapien

<400> SEQUENCE: 30

Met Ala Ser Leu Val Ser Leu Glu Leu Gly Leu Leu Leu Ala Val Leu
 1               5                  10                  15

Val Val Thr Ala Thr Ala Ser Pro Pro Ala Gly Leu Leu Ser Leu Leu
                20                  25                  30

Thr Ser Gly Gln Gly Ala Leu Asp Gln Glu Ala Leu Gly Gly Leu Leu
            35                  40                  45
```

```
Asn Thr Leu Ala Asp Arg Val His Cys Thr Asn Gly Pro Cys Gly Lys
 50                  55                  60

Cys Leu Ser Val Glu Asp Ala Leu Gly Leu Gly Glu Pro Glu Gly Ser
 65                  70                  75                  80

Gly Leu Pro Pro Gly Pro Val Leu Glu Ala Arg Tyr Val Ala Arg Leu
                 85                  90                  95

Ser Ala Ala Val Leu Tyr Leu Ser Asn Pro Glu Gly Thr Cys Glu
                100                 105                 110

Asp Thr Arg Ala Gly Leu Trp Ala Ser His Ala Asp His Leu Leu Ala
                115                 120                 125

Leu Leu Glu Ser Pro Lys Ala Leu Thr Pro Gly Leu Ser Trp Leu Leu
        130                 135                 140

Gln Arg Met Gln Ala Arg Ala Ala Gly Gln Thr Pro Lys Thr Ala Cys
145                 150                 155                 160

Val Asp Ile Pro Gln Leu Leu Glu Glu Ala Val Gly Ala Gly Ala Pro
                165                 170                 175

Gly Ser Ala Gly Gly Val Leu Ala Ala Leu Leu Asp His Val Arg Ser
                180                 185                 190

Gly Ser Cys Phe His Ala Leu Pro Ser Pro Gln Tyr Phe Val Asp Phe
        195                 200                 205

Val Phe Gln Gln His Ser Ser Glu Val Pro Met Thr Leu Ala Glu Leu
210                 215                 220

Ser Ala Leu Met Gln Arg Leu Gly Val Gly Arg Glu Ala His Ser Asp
225                 230                 235                 240

His Ser His Arg His Arg Gly Ala Ser Ser Arg Asp Pro Val Pro Leu
                245                 250                 255

Ile Ser Ser Asn Ser Ser Ser Val Trp Asp Thr Val Cys Leu Ser
                260                 265                 270

Ala Arg Asp Val Met Ala Ala Tyr Gly Leu Ser Glu Gln Ala Gly Val
        275                 280                 285

Thr Pro Glu Ala Trp Ala Gln Leu Ser Pro Ala Leu Leu Gln Gln Gln
        290                 295                 300

Leu Ser Gly Ala Cys Thr Ser Gln Ser Arg Pro Pro Val Gln Asp Gln
305                 310                 315                 320

Leu Ser Gln Ser Glu Arg Tyr Leu Tyr Gly Ser Leu Ala Thr Leu Leu
                325                 330                 335

Ile Cys Leu Cys Ala Val Phe Gly Leu Leu Leu Thr Cys Thr Gly
                340                 345                 350

Cys Arg Gly Val Ala His Tyr Ile Leu Gln Thr Phe Leu Ser Leu Ala
        355                 360                 365

Val Gly Ala Leu Thr Gly Asp Ala Val Leu His Leu Thr Pro Lys Val
        370                 375                 380

Leu Gly Leu His Thr His Ser Glu Glu Gly Leu Ser Pro Gln Pro Thr
385                 390                 395                 400

Trp Arg Leu Leu Ala Met Leu Ala Gly Leu Tyr Ala Phe Phe Leu Phe
                405                 410                 415

Glu Asn Leu Phe Asn Leu Leu Pro Arg Asp Pro Glu Asp Leu Glu
                420                 425                 430

Asp Gly Pro Cys Gly His Ser His Ser His Gly His Ser His
        435                 440                 445

Gly Val Ser Leu Gln Leu Ala Pro Ser Glu Leu Arg Gln Pro Lys Pro
450                 455                 460

Pro His Glu Gly Ser Arg Ala Asp Leu Val Ala Glu Glu Ser Pro Glu
```

-continued

```
                    465                 470                 475                 480
Leu Leu Asn Pro Glu Pro Arg Arg Leu Ser Pro Glu Leu Arg Leu Leu
                485                 490                 495
Pro Tyr Met Ile Thr Leu Gly Asp Ala Val His Asn Phe Ala Asp Gly
                500                 505                 510
Leu Ala Val Gly Ala Ala Phe Ala Ser Ser Trp Lys Thr Gly Leu Ala
                515                 520                 525
Thr Ser Leu Ala Val Phe Cys His Glu Leu Pro His Glu Leu Gly Asp
                530                 535                 540
Phe Ala Ala Leu Leu His Ala Gly Leu Ser Val Arg Gln Ala Leu Leu
545                 550                 555                 560
Leu Asn Leu Ala Ser Ala Leu Thr Ala Phe Ala Gly Leu Tyr Val Ala
                565                 570                 575
Leu Ala Val Gly Val Ser Glu Glu Ser Glu Ala Trp Ile Leu Ala Val
                580                 585                 590
Ala Thr Gly Leu Phe Leu Tyr Val Ala Leu Cys Asp Met Leu Pro Ala
                595                 600                 605
Met Leu Lys Val Arg Asp Pro Arg Pro Trp Leu Leu Phe Leu Leu His
                610                 615                 620
Asn Val Gly Leu Leu Gly Gly Trp Thr Val Leu Leu Leu Ser Leu
625                 630                 635                 640
Tyr Glu Asp Asp Ile Thr Phe
                645

<210> SEQ ID NO 31
<211> LENGTH: 1910
<212> TYPE: DNA
<213> ORGANISM: Homo sapien
<220> FEATURE:
<221> NAME/KEY: CDS
<222> LOCATION: (101)...(1762)

<400> SEQUENCE: 31
agtctggccc tggacaaccc cagcaaagcc gccctcagcc agcccagaag cactgggcct      60
tggccacagc aacacccact gagcacgctg ggagctgagt atg gcg tcc ctg gtc     115
                                                Met Ala Ser Leu Val
                                                  1               5 tcg ctg gag ctg gga ctg ctt ctg gct gtg ctg gtg gtg acg gcg acg    163
Ser Leu Glu Leu Gly Leu Leu Leu Ala Val Leu Val Val Thr Ala Thr
              10                  15                  20 gcg tcc ccg cct gct ggt ctg ctg agc ctg ctc acc tct ggc cag ggc    211
Ala Ser Pro Pro Ala Gly Leu Leu Ser Leu Leu Thr Ser Gly Gln Gly
          25                  30                  35 gct ctg gat caa gag gct ctg ggc ggc ctg tta aat acg ctg gcg gac    259
Ala Leu Asp Gln Glu Ala Leu Gly Gly Leu Leu Asn Thr Leu Ala Asp
      40                  45                  50 cgt gtg cac tgc gcc aac ggg ccg tgt gga aag gcc tgc gta gat atc    307
Arg Val His Cys Ala Asn Gly Pro Cys Gly Lys Ala Cys Val Asp Ile
  55                  60                  65 cct cag ctg ctg gag gag gcg gtg ggg gcg ggg gct ccg ggc agt gct    355
Pro Gln Leu Leu Glu Glu Ala Val Gly Ala Gly Ala Pro Gly Ser Ala
 70                  75                  80                  85 ggc ggc gtc ctg gct gcc ctg ctg gac cat gtc agg agc ggg tct tgc    403
Gly Gly Val Leu Ala Ala Leu Leu Asp His Val Arg Ser Gly Ser Cys
              90                  95                 100 ttc cac gcc ttg ccg agc cct cag tac ttc gtg gac ttt gtg ttc cag    451
Phe His Ala Leu Pro Ser Pro Gln Tyr Phe Val Asp Phe Val Phe Gln
             105                 110                 115
```

```
cag cac agc agc gag gtc cct atg acg ctg gcc gag ctg tca gcc ttg      499
Gln His Ser Ser Glu Val Pro Met Thr Leu Ala Glu Leu Ser Ala Leu
        120                 125                 130 atg cag cgc ctg ggg gtg ggc agg gag gcc cac agt gac cac agt cat      547
Met Gln Arg Leu Gly Val Gly Arg Glu Ala His Ser Asp His Ser His
135                 140                 145 cgg cac agg gga gcc agc agc cgg gac cct gtg ccc ctc atc agc tcc      595
Arg His Arg Gly Ala Ser Ser Arg Asp Pro Val Pro Leu Ile Ser Ser
150                 155                 160                 165 agc aac agc tcc agt gtg tgg gac acg gta tgc ctg agt gcc agg gac      643
Ser Asn Ser Ser Ser Val Trp Asp Thr Val Cys Leu Ser Ala Arg Asp
                170                 175                 180 gtg atg gct gca tat gga ctg tcg gaa cag gct ggg gtg acc ccg gag      691
Val Met Ala Ala Tyr Gly Leu Ser Glu Gln Ala Gly Val Thr Pro Glu
            185                 190                 195 gcc tgg gcc caa ctg agc cct gcc ctc caa cag cag ctg agt gga          739
Ala Trp Ala Gln Leu Ser Pro Ala Leu Leu Gln Gln Gln Leu Ser Gly
        200                 205                 210 gcc tgc acc tcc cag tcc agg ccc ccc gtc cag gac cag ctc agc cag      787
Ala Cys Thr Ser Gln Ser Arg Pro Pro Val Gln Asp Gln Leu Ser Gln
215                 220                 225 tca gag agg tat ctg tac ggc tcc ctg gcc acg ctg ctc atc tgc ctc      835
Ser Glu Arg Tyr Leu Tyr Gly Ser Leu Ala Thr Leu Leu Ile Cys Leu
230                 235                 240                 245 tgc gcg gtc ttt ggc ctc ctg ctg acc tgc act ggc tgc agg ggg          883
Cys Ala Val Phe Gly Leu Leu Leu Thr Cys Thr Gly Cys Arg Gly
                250                 255                 260 gtc acc cac tac atc ctg cag acc ttc ctg agc ctg gca gtg ggt gca      931
Val Thr His Tyr Ile Leu Gln Thr Phe Leu Ser Leu Ala Val Gly Ala
            265                 270                 275 gtc act ggg gac gct gtc ctg cat ctg acg ccc aag gtg ctg ggg ctg      979
Val Thr Gly Asp Ala Val Leu His Leu Thr Pro Lys Val Leu Gly Leu
        280                 285                 290 cat aca cac agc gaa gag ggc ctc agc cca cag ccc acc tgg cgc ctc     1027
His Thr His Ser Glu Glu Gly Leu Ser Pro Gln Pro Thr Trp Arg Leu
    295                 300                 305 ctg gct atg ctg gcc ggg ctc tac gcc ttc ttc ctg ttt gag aac ctc     1075
Leu Ala Met Leu Ala Gly Leu Tyr Ala Phe Phe Leu Phe Glu Asn Leu
310                 315                 320                 325 ttc aat ctc ctg ctg ccc agg gac ccg gag gac ctg gag gac ggg ccc     1123
Phe Asn Leu Leu Leu Pro Arg Asp Pro Glu Asp Leu Glu Asp Gly Pro
                330                 335                 340 tgc ggc cac agc agc cat agc cac ggg ggc cac agc cac ggt gtg tcc     1171
Cys Gly His Ser Ser His Ser His Gly Gly His Ser His Gly Val Ser
            345                 350                 355 ctg cag ctg gca ccc agc gag ctc cgg cag ccc aag ccc ccc cac gag     1219
Leu Gln Leu Ala Pro Ser Glu Leu Arg Gln Pro Lys Pro Pro His Glu
        360                 365                 370 ggc tcc cgc gca gac ctg gtg gcg gag gag agc ccg gag ctg ctg aac     1267
Gly Ser Arg Ala Asp Leu Val Ala Glu Glu Ser Pro Glu Leu Leu Asn
    375                 380                 385 cct gag ccc agg aga ctg agc cca gag ttg agg cta ctg ccc tat atg     1315
Pro Glu Pro Arg Arg Leu Ser Pro Glu Leu Arg Leu Leu Pro Tyr Met
390                 395                 400                 405 atc act ctg ggc gac gcc gtg cac aac ttc gcc gac ggg ctg gcc gtg     1363
Ile Thr Leu Gly Asp Ala Val His Asn Phe Ala Asp Gly Leu Ala Val
                410                 415                 420 ggc gcc gcc ttc gcg tcc tcc tgg aag acc ggg ctg gcc acc tcg ctg     1411
Gly Ala Ala Phe Ala Ser Ser Trp Lys Thr Gly Leu Ala Thr Ser Leu
```

-continued

```
                    425                 430                 435
gcc gtg ttc tgc cac gag ttg cca cac gag ctg ggg gac ttc gcc gcc     1459
Ala Val Phe Cys His Glu Leu Pro His Glu Leu Gly Asp Phe Ala Ala
            440                 445                 450 ttg ctg cac gcg ggg ctg tcc gtg cgc caa gca ctg ctg aac ctg         1507
Leu Leu His Ala Gly Leu Ser Val Arg Gln Ala Leu Leu Asn Leu
        455                 460                 465 gcc tcc gcg ctc acg gcc ttc gct ggt ctc tac gtg gca ctc gcg gtt     1555
Ala Ser Ala Leu Thr Ala Phe Ala Gly Leu Tyr Val Ala Leu Ala Val
470                 475                 480                 485 gga gtc agc gag gag agc gag gcc tgg atc ctg gca gtg gcc acc ggc     1603
Gly Val Ser Glu Glu Ser Glu Ala Trp Ile Leu Ala Val Ala Thr Gly
                490                 495                 500 ctg ttc ctc tac gta gca ctc tgc gac atg ctc ccg gcg atg ttg aaa     1651
Leu Phe Leu Tyr Val Ala Leu Cys Asp Met Leu Pro Ala Met Leu Lys
            505                 510                 515 gta cgg gac ccg cgg ccc tgg ctc ctc ttc ctg ctg cac aac gtg ggc     1699
Val Arg Asp Pro Arg Pro Trp Leu Leu Phe Leu Leu His Asn Val Gly
        520                 525                 530 ctg ctg ggc ggc tgg acc gtc ctg ctg ctg tcc ctg tac gag gat         1747
Leu Leu Gly Gly Trp Thr Val Leu Leu Leu Ser Leu Tyr Glu Asp
535                 540                 545 gac atc acc ttc tga taccctgccc tagtccccca cctttgactt aagatcccac     1802
Asp Ile Thr Phe *
550 acctcacaaa cctacagccc agaaaccaga agcccctata gaggcccag tcccaactcc   1862 agtaaagaca ctcttgtcct tggaaaaaaa aaaaaaaaaa aaaaaaaa              1910

<210> SEQ ID NO 32
<211> LENGTH: 553
<212> TYPE: PRT
<213> ORGANISM: Homo sapien

<400> SEQUENCE: 32

Met Ala Ser Leu Val Ser Leu Glu Leu Gly Leu Leu Leu Ala Val Leu
1               5                   10                  15

Val Val Thr Ala Thr Ala Ser Pro Pro Ala Gly Leu Leu Ser Leu Leu
            20                  25                  30

Thr Ser Gly Gln Gly Ala Leu Asp Gln Glu Ala Leu Gly Gly Leu Leu
        35                  40                  45

Asn Thr Leu Ala Asp Arg Val His Cys Ala Asn Gly Pro Cys Gly Lys
    50                  55                  60

Ala Cys Val Asp Ile Pro Gln Leu Leu Glu Glu Ala Val Gly Ala Gly
65                  70                  75                  80

Ala Pro Gly Ser Ala Gly Gly Val Leu Ala Leu Leu Asp His Val
            85                  90                  95

Arg Ser Gly Ser Cys Phe His Ala Leu Pro Ser Pro Gln Tyr Phe Val
        100                 105                 110

Asp Phe Val Phe Gln Gln His Ser Ser Glu Val Pro Met Thr Leu Ala
    115                 120                 125

Glu Leu Ser Ala Leu Met Gln Arg Leu Gly Val Gly Arg Glu Ala His
130                 135                 140

Ser Asp His Ser His Arg His Arg Gly Ala Ser Ser Arg Asp Pro Val
145                 150                 155                 160

Pro Leu Ile Ser Ser Asn Ser Ser Ser Val Trp Asp Thr Val Cys
            165                 170                 175
```

```
Leu Ser Ala Arg Asp Val Met Ala Ala Tyr Gly Leu Ser Glu Gln Ala
            180                 185                 190

Gly Val Thr Pro Glu Ala Trp Ala Gln Leu Ser Pro Ala Leu Leu Gln
        195                 200                 205

Gln Gln Leu Ser Gly Ala Cys Thr Ser Gln Ser Arg Pro Pro Val Gln
    210                 215                 220

Asp Gln Leu Ser Gln Ser Glu Arg Tyr Leu Tyr Gly Ser Leu Ala Thr
225                 230                 235                 240

Leu Leu Ile Cys Leu Cys Ala Val Phe Gly Leu Leu Leu Thr Cys
                245                 250                 255

Thr Gly Cys Arg Gly Val Thr His Tyr Ile Leu Gln Thr Phe Leu Ser
            260                 265                 270

Leu Ala Val Gly Ala Val Thr Gly Asp Ala Val Leu His Leu Thr Pro
        275                 280                 285

Lys Val Leu Gly Leu His Thr His Ser Glu Glu Gly Leu Ser Pro Gln
    290                 295                 300

Pro Thr Trp Arg Leu Leu Ala Met Leu Ala Gly Leu Tyr Ala Phe Phe
305                 310                 315                 320

Leu Phe Glu Asn Leu Phe Asn Leu Leu Leu Pro Arg Asp Pro Glu Asp
                325                 330                 335

Leu Glu Asp Gly Pro Cys Gly His Ser Ser His Ser His Gly Gly His
            340                 345                 350

Ser His Gly Val Ser Leu Gln Leu Ala Pro Ser Glu Leu Arg Gln Pro
        355                 360                 365

Lys Pro Pro His Glu Gly Ser Arg Ala Asp Leu Val Ala Glu Glu Ser
    370                 375                 380

Pro Glu Leu Leu Asn Pro Glu Pro Arg Arg Leu Ser Pro Glu Leu Arg
385                 390                 395                 400

Leu Leu Pro Tyr Met Ile Thr Leu Gly Asp Ala Val His Asn Phe Ala
                405                 410                 415

Asp Gly Leu Ala Val Gly Ala Ala Phe Ala Ser Ser Trp Lys Thr Gly
            420                 425                 430

Leu Ala Thr Ser Leu Ala Val Phe Cys His Glu Leu Pro His Glu Leu
        435                 440                 445

Gly Asp Phe Ala Ala Leu Leu His Ala Gly Leu Ser Val Arg Gln Ala
    450                 455                 460

Leu Leu Leu Asn Leu Ala Ser Ala Leu Thr Ala Phe Ala Gly Leu Tyr
465                 470                 475                 480

Val Ala Leu Ala Val Gly Val Ser Glu Glu Ser Glu Ala Trp Ile Leu
                485                 490                 495

Ala Val Ala Thr Gly Leu Phe Leu Tyr Val Ala Leu Cys Asp Met Leu
            500                 505                 510

Pro Ala Met Leu Lys Val Arg Asp Pro Arg Pro Trp Leu Leu Phe Leu
        515                 520                 525

Leu His Asn Val Gly Leu Leu Gly Gly Trp Thr Val Leu Leu Leu Leu
    530                 535                 540

Ser Leu Tyr Glu Asp Asp Ile Thr Phe
545                 550

<210> SEQ ID NO 33
<211> LENGTH: 598
<212> TYPE: DNA
<213> ORGANISM: Homo sapien
<220> FEATURE:
<221> NAME/KEY: CDS
```

<222> LOCATION: (23)...(421)

<400> SEQUENCE: 33

```
cagagtcact cctgccttca cc atg aag tcc agc ggc ctc ttc ccc ttc ctg        52
                         Met Lys Ser Ser Gly Leu Phe Pro Phe Leu
                          1               5                   10 gtg ctg ctt gcc ctg gga act ctg gca cct tgg gct gtg gaa ggc tct       100
Val Leu Leu Ala Leu Gly Thr Leu Ala Pro Trp Ala Val Glu Gly Ser
             15                  20                  25 gga aag tcc ttc aaa gct gga gtc tgt cct cct aag aaa tct gcc cag       148
Gly Lys Ser Phe Lys Ala Gly Val Cys Pro Pro Lys Lys Ser Ala Gln
         30                  35                  40 tgc ctt aga tac aag aaa cct gag tgc cag agt gac tgg cag tgt cca       196
Cys Leu Arg Tyr Lys Lys Pro Glu Cys Gln Ser Asp Trp Gln Cys Pro
     45                  50                  55 ggg aag aag aga tgt tgt cct gac act tgt ggc atc aaa tgc ctg gat       244
Gly Lys Lys Arg Cys Cys Pro Asp Thr Cys Gly Ile Lys Cys Leu Asp
 60                  65                  70 cct gtt gac acc cca aac cca aca agg agg aag cct ggg aag tgc cca       292
Pro Val Asp Thr Pro Asn Pro Thr Arg Arg Lys Pro Gly Lys Cys Pro
 75                  80                  85                  90 gtg act tat ggc caa tgt ttg atg ctt aac ccc ccc aat ttc tgt gag       340
Val Thr Tyr Gly Gln Cys Leu Met Leu Asn Pro Pro Asn Phe Cys Glu
                 95                 100                 105 atg gat ggc cag tgc aag cgt gac ttg aag tgt tgc atg ggc atg tgt       388
Met Asp Gly Gln Cys Lys Arg Asp Leu Lys Cys Cys Met Gly Met Cys
            110                 115                 120 ggg aaa tcc tgc gtt tcc cct gtg aaa gct tga ttcctgccat atggaggagg     441
Gly Lys Ser Cys Val Ser Pro Val Lys Ala  *
        125                 130 ctctggagtc ctgctctgtg tggtccaggt cctttccacc ctgagacttg gctccaccac     501
tgatatcctc ctttggggaa aggcttggca cacagcaggc tttcaagaag tgccagttga     561
tcaatgaata aataaacgag cctatttctc tttgcac                              598
```

<210> SEQ ID NO 34
<211> LENGTH: 132
<212> TYPE: PRT
<213> ORGANISM: Homo sapien

<400> SEQUENCE: 34

```
Met Lys Ser Ser Gly Leu Phe Pro Phe Leu Val Leu Leu Ala Leu Gly
 1               5                  10                  15

Thr Leu Ala Pro Trp Ala Val Glu Gly Ser Gly Lys Ser Phe Lys Ala
             20                  25                  30

Gly Val Cys Pro Pro Lys Lys Ser Ala Gln Cys Leu Arg Tyr Lys Lys
         35                  40                  45

Pro Glu Cys Gln Ser Asp Trp Gln Cys Pro Gly Lys Lys Arg Cys Cys
     50                  55                  60

Pro Asp Thr Cys Gly Ile Lys Cys Leu Asp Pro Val Asp Thr Pro Asn
 65                  70                  75                  80

Pro Thr Arg Arg Lys Pro Gly Lys Cys Pro Val Thr Tyr Gly Gln Cys
                 85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
```

-continued

```
                130

<210> SEQ ID NO 35
<211> LENGTH: 3079
<212> TYPE: DNA
<213> ORGANISM: Homo sapien
<220> FEATURE:
<221> NAME/KEY: CDS
<222> LOCATION: (25)...(2448)

<400> SEQUENCE: 35
ggcacaaagt tgggggccgc gaag atg agg ctg tcc ccg gcg ccc ctg aag         51
                          Met Arg Leu Ser Pro Ala Pro Leu Lys
                            1               5 ctg agc cgg act ccg gca ctg ctg gcc ctg gcg ctg ccc ctg gcc gcg        99
Leu Ser Arg Thr Pro Ala Leu Leu Ala Leu Ala Leu Pro Leu Ala Ala
 10              15                  20                  25 gcg ctg gcc ttc tcc gac gag acc ctg gac aaa gtg ccc aag tca gag       147
Ala Leu Ala Phe Ser Asp Glu Thr Leu Asp Lys Val Pro Lys Ser Glu
                 30                  35                  40 ggc tac tgt agc cgt atc ctg cgc gcc cag ggc acg cgg cgc gag ggc       195
Gly Tyr Cys Ser Arg Ile Leu Arg Ala Gln Gly Thr Arg Arg Glu Gly
             45                  50                  55 tac acc gag ttc agc ctc cgc gtg gag ggc gac ccc gac ttc tac aag       243
Tyr Thr Glu Phe Ser Leu Arg Val Glu Gly Asp Pro Asp Phe Tyr Lys
         60                  65                  70 ccg gga acc agc tac cgc gta aca ctt tca gct gct cct ccc tcc tac       291
Pro Gly Thr Ser Tyr Arg Val Thr Leu Ser Ala Ala Pro Pro Ser Tyr
     75                  80                  85 ttc aga gga ttc aca tta att gcc ctc aga gag aac aga gag ggt gat       339
Phe Arg Gly Phe Thr Leu Ile Ala Leu Arg Glu Asn Arg Glu Gly Asp
 90                  95                 100                 105 aag gaa gaa gac cat gct ggg acc ttc cag atc ata gac gaa gaa gaa       387
Lys Glu Glu Asp His Ala Gly Thr Phe Gln Ile Ile Asp Glu Glu Glu
                110                 115                 120 act cag ttt atg agc aat tgc cct gtt gca gtc act gaa agc act cca       435
Thr Gln Phe Met Ser Asn Cys Pro Val Ala Val Thr Glu Ser Thr Pro
            125                 130                 135 cgg agg agg acc cgg atc cag gtg ttt tgg ata gca cca cca gcg gga       483
Arg Arg Arg Thr Arg Ile Gln Val Phe Trp Ile Ala Pro Pro Ala Gly
        140                 145                 150 aca ggc tgc gtg att ctg aag gcc agc atc gta caa aaa cgc att att       531
Thr Gly Cys Val Ile Leu Lys Ala Ser Ile Val Gln Lys Arg Ile Ile
    155                 160                 165 tat ttt caa gat gag ggc tct ctg acc aag aaa ctt tgt gaa caa gat       579
Tyr Phe Gln Asp Glu Gly Ser Leu Thr Lys Lys Leu Cys Glu Gln Asp
170                 175                 180                 185 tcc aca ttt gat ggg gtg act gac aaa ccc atc tta gac tgc tgt gcc       627
Ser Thr Phe Asp Gly Val Thr Asp Lys Pro Ile Leu Asp Cys Cys Ala
                190                 195                 200 tgc gga act gcc aag tac aga ctc aca ttt tat ggg aat tgg tcc gag       675
Cys Gly Thr Ala Lys Tyr Arg Leu Thr Phe Tyr Gly Asn Trp Ser Glu
            205                 210                 215 aag aca cac cca aag gat tac cct cgt cgg gcc aac cac tgg tct gcg       723
Lys Thr His Pro Lys Asp Tyr Pro Arg Arg Ala Asn His Trp Ser Ala
        220                 225                 230 atc atc gga gga tcc cac tcc aag aat tat gta ctg tgg gaa tat gga       771
Ile Ile Gly Gly Ser His Ser Lys Asn Tyr Val Leu Trp Glu Tyr Gly
    235                 240                 245 gga tat gcc agc gaa ggc gtc aaa caa gtt gca gaa ttg ggc tca ccc       819
Gly Tyr Ala Ser Glu Gly Val Lys Gln Val Ala Glu Leu Gly Ser Pro
```

-continued

```
        250                 255                 260                 265 gtg aaa atg gag gaa gaa att cga caa cag agt gat gag gtc ctc acc       867
Val Lys Met Glu Glu Glu Ile Arg Gln Gln Ser Asp Glu Val Leu Thr
            270                 275                 280 gtc atc aaa gcc aaa gcc caa tgg cca gcc tgg cag cct ctc aac gtg       915
Val Ile Lys Ala Lys Ala Gln Trp Pro Ala Trp Gln Pro Leu Asn Val
                285                 290                 295 aga gca gca cct tca gct gaa ttt tcc gtg gac aga acg cgc cat tta       963
Arg Ala Ala Pro Ser Ala Glu Phe Ser Val Asp Arg Thr Arg His Leu
            300                 305                 310 atg tcc ttc ctg acc atg atg ggc cct agt ccc gac tgg aac gta ggc      1011
Met Ser Phe Leu Thr Met Met Gly Pro Ser Pro Asp Trp Asn Val Gly
        315                 320                 325 tta tct gca gaa gat ctg tgc acc aag gaa tgt ggc tgg gtc cag aag      1059
Leu Ser Ala Glu Asp Leu Cys Thr Lys Glu Cys Gly Trp Val Gln Lys
330                 335                 340                 345 gtg gtg caa gac ctg att ccc tgg gac gct ggc acc gac agc ggg gtg      1107
Val Val Gln Asp Leu Ile Pro Trp Asp Ala Gly Thr Asp Ser Gly Val
                350                 355                 360 acc tat gag tca ccc aac aaa ccc acc att ccc cag gag aaa atc cgg      1155
Thr Tyr Glu Ser Pro Asn Lys Pro Thr Ile Pro Gln Glu Lys Ile Arg
            365                 370                 375 ccc ctg acc agc ctg gac cat cct cag agt cct ttc tat gac cca gag      1203
Pro Leu Thr Ser Leu Asp His Pro Gln Ser Pro Phe Tyr Asp Pro Glu
        380                 385                 390 ggt ggg tcc atc act caa gta gcc aga gtt gtc atc gag aga atc gca      1251
Gly Gly Ser Ile Thr Gln Val Ala Arg Val Val Ile Glu Arg Ile Ala
    395                 400                 405 cgg aag ggt gaa caa tgc aat att gta cct gac aat gtc gat gat att      1299
Arg Lys Gly Glu Gln Cys Asn Ile Val Pro Asp Asn Val Asp Asp Ile
410                 415                 420                 425 gta gct gac ctg gct cca gaa gag aaa gat gaa gat gac acc cct gaa      1347
Val Ala Asp Leu Ala Pro Glu Glu Lys Asp Glu Asp Asp Thr Pro Glu
                430                 435                 440 acc tgc atc tac tcc aac tgg tcc cca tgg tcc gcc tgc agc tcc tcc      1395
Thr Cys Ile Tyr Ser Asn Trp Ser Pro Trp Ser Ala Cys Ser Ser Ser
            445                 450                 455 acc tgt gac aaa ggc aag agg atg cga cag cgc atg ctg aaa gca cag      1443
Thr Cys Asp Lys Gly Lys Arg Met Arg Gln Arg Met Leu Lys Ala Gln
        460                 465                 470 ctg gac ctc agc gtc ccc tgc cct gac acc cag gac ttc cag ccc tgc      1491
Leu Asp Leu Ser Val Pro Cys Pro Asp Thr Gln Asp Phe Gln Pro Cys
    475                 480                 485 atg ggc cct ggc tgc agt gac gaa gac ggc tcc acc tgc acc atg tcc      1539
Met Gly Pro Gly Cys Ser Asp Glu Asp Gly Ser Thr Cys Thr Met Ser
490                 495                 500                 505 gag tgg atc acc tgg tcg ccc tgc agc atc tcc tgc ggc atg ggc atg      1587
Glu Trp Ile Thr Trp Ser Pro Cys Ser Ile Ser Cys Gly Met Gly Met
                510                 515                 520 agg tcc cgg gag agg tat gtg aag cag ttc ccg gag gac ggc tcc gtg      1635
Arg Ser Arg Glu Arg Tyr Val Lys Gln Phe Pro Glu Asp Gly Ser Val
            525                 530                 535 tgc acg ctg ccc act gag gaa atg gag aag tgc acg gtc aac gag gag      1683
Cys Thr Leu Pro Thr Glu Glu Met Glu Lys Cys Thr Val Asn Glu Glu
        540                 545                 550 tgc tct ccc agc agc tgc ctg atg acc gag tgg ggc gag tgg gac gag      1731
Cys Ser Pro Ser Ser Cys Leu Met Thr Glu Trp Gly Glu Trp Asp Glu
    555                 560                 565 tgc agc gcc acc tgc ggc atg ggc atg aag aag cgg cac cgc atg atc      1779
```

```
                Cys Ser Ala Thr Cys Gly Met Gly Met Lys Lys Arg His Arg Met Ile
                570             575             580             585 aag atg aac ccc gca gat ggc tcc atg tgc aaa gcc gag aca tca cag         1827
Lys Met Asn Pro Ala Asp Gly Ser Met Cys Lys Ala Glu Thr Ser Gln
                        590             595             600 gca gag aag tgc atg atg cca gag tgc cac acc atc cca tgc ttg ctg         1875
Ala Glu Lys Cys Met Met Pro Glu Cys His Thr Ile Pro Cys Leu Leu
                605             610             615 tcc cca tgg tcc gag tgg agt gac tgc agc gtg acc tgc ggg aag ggc         1923
Ser Pro Trp Ser Glu Trp Ser Asp Cys Ser Val Thr Cys Gly Lys Gly
        620             625             630 atg cga acc cga cag cgg atg ctc aag tct ctg gca gaa ctt gga gac         1971
Met Arg Thr Arg Gln Arg Met Leu Lys Ser Leu Ala Glu Leu Gly Asp
    635             640             645 tgc aat gag gat ctg gag cag gtg gag aag tgc atg ctc cct gaa tgc         2019
Cys Asn Glu Asp Leu Glu Gln Val Glu Lys Cys Met Leu Pro Glu Cys
650             655             660             665 ccc att gac tgt gag ctc acc gag tgg tcc cag tgg tcg gaa tgt aac         2067
Pro Ile Asp Cys Glu Leu Thr Glu Trp Ser Gln Trp Ser Glu Cys Asn
                670             675             680 aag tca tgt ggg aaa ggc cac gtg att cga acc cgg atg atc caa atg         2115
Lys Ser Cys Gly Lys Gly His Val Ile Arg Thr Arg Met Ile Gln Met
            685             690             695 gag cct cag ttt gga ggt gca ccc tgc cca gag act gtg cag cga aaa         2163
Glu Pro Gln Phe Gly Gly Ala Pro Cys Pro Glu Thr Val Gln Arg Lys
        700             705             710 aag tgc cgc atc cga aaa tgc ctt cga aat cca tcc atc caa aag cca         2211
Lys Cys Arg Ile Arg Lys Cys Leu Arg Asn Pro Ser Ile Gln Lys Pro
    715             720             725 cgc tgg agg gag gcc cga gag agc cgg cgg agt gag cag ctg aag gaa         2259
Arg Trp Arg Glu Ala Arg Glu Ser Arg Arg Ser Glu Gln Leu Lys Glu
730             735             740             745 gag tct gaa ggg gag cag ttc cca ggt tgt agg atg cgc cca tgg acg         2307
Glu Ser Glu Gly Glu Gln Phe Pro Gly Cys Arg Met Arg Pro Trp Thr
                750             755             760 gcc tgg tca gaa tgc acc aaa ctg tgc gga ggt gga att cag gaa cgt         2355
Ala Trp Ser Glu Cys Thr Lys Leu Cys Gly Gly Gly Ile Gln Glu Arg
            765             770             775 tac atg act gta aag aag aga ttc aaa agc tcc cag ttt acc agc tgc         2403
Tyr Met Thr Val Lys Lys Arg Phe Lys Ser Ser Gln Phe Thr Ser Cys
        780             785             790 aaa gac aag aag gag atc aga gca tgc aat gtt cat cct tgt tag             2448
Lys Asp Lys Lys Glu Ile Arg Ala Cys Asn Val His Pro Cys  *
    795             800             805 caagggtacg agttccccag ggctgcactc tagattccag agtcaccaat ggctggatta       2508
tttgcttgtt taagacaatt taaattgtgt acgctagttt tcattttttgc agtgtggttc      2568 gcccagtagt cttgtggatg ccagagacat cctttctgaa tacttcttga tgggtacagg       2628
ctgagtgggg cgccctcacc tccagccagc ctcttcctgc agaggagtag tgtcagccac       2688
cttgtactaa gctgaaacat gtccctctgg agcttccacc tggccaggga ggacggagac       2748
tttgacctac tccacatgga gaggcaacca tgtctggaag tgactatgcc tgagtcccag       2808
ggtgcggcag gtaggaaaca ttcacagatg aagacagcag attccccaca ttctcatctt       2868
tggcctgttc aatgaaacca ttgtttgccc atctcttctt agtggaactt taggtctctt       2928
ttcaagtctc ctcagtcatc aatagttcct ggggaaaaac agagctggta gacttgaaga       2988
ggagcattga tgttgggtgg cttttgttct ttcactgaga aattcggaat acatttgtct       3048
```
cacccctgat attggttcct gatgccccag c 3079

<210> SEQ ID NO 36
<211> LENGTH: 807
<212> TYPE: PRT
<213> ORGANISM: Homo sapien

<400> SEQUENCE: 36

```
Met Arg Leu Ser Pro Ala Pro Leu Lys Leu Ser Arg Thr Pro Ala Leu
 1               5                  10                  15

Leu Ala Leu Ala Leu Pro Leu Ala Ala Ala Leu Ala Phe Ser Asp Glu
                20                  25                  30

Thr Leu Asp Lys Val Pro Lys Ser Glu Gly Tyr Cys Ser Arg Ile Leu
            35                  40                  45

Arg Ala Gln Gly Thr Arg Arg Glu Gly Tyr Thr Glu Phe Ser Leu Arg
        50                  55                  60

Val Glu Gly Asp Pro Asp Phe Tyr Lys Pro Gly Thr Ser Tyr Arg Val
 65                  70                  75                  80

Thr Leu Ser Ala Ala Pro Pro Ser Tyr Phe Arg Gly Phe Thr Leu Ile
                85                  90                  95

Ala Leu Arg Glu Asn Arg Glu Gly Asp Lys Glu Asp His Ala Gly
                100                 105                 110

Thr Phe Gln Ile Ile Asp Glu Glu Thr Gln Phe Met Ser Asn Cys
                115                 120                 125

Pro Val Ala Val Thr Glu Ser Thr Pro Arg Arg Thr Arg Ile Gln
    130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
        195                 200                 205

Leu Thr Phe Tyr Gly Asn Trp Ser Glu Lys Thr His Pro Lys Asp Tyr
    210                 215                 220

Pro Arg Arg Ala Asn His Trp Ser Ala Ile Ile Gly Gly Ser His Ser
225                 230                 235                 240

Lys Asn Tyr Val Leu Trp Glu Tyr Gly Gly Tyr Ala Ser Glu Gly Val
                245                 250                 255

Lys Gln Val Ala Glu Leu Gly Ser Pro Val Lys Met Glu Glu Glu Ile
            260                 265                 270

Arg Gln Gln Ser Asp Glu Val Leu Thr Val Ile Lys Ala Lys Ala Gln
        275                 280                 285

Trp Pro Ala Trp Gln Pro Leu Asn Val Arg Ala Ala Pro Ser Ala Glu
    290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
        355                 360                 365
```

```
Pro Thr Ile Pro Gln Glu Lys Ile Arg Pro Leu Thr Ser Leu Asp His
    370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
            405                 410                 415

Ile Val Pro Asp Asn Val Asp Asp Ile Val Ala Asp Leu Ala Pro Glu
        420                 425                 430

Glu Lys Asp Glu Asp Thr Pro Glu Thr Cys Ile Tyr Ser Asn Trp
        435             440                 445

Ser Pro Trp Ser Ala Cys Ser Ser Thr Cys Asp Lys Gly Lys Arg
    450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
            485                 490                 495

Glu Asp Gly Ser Thr Cys Thr Met Ser Glu Trp Ile Thr Trp Ser Pro
        500                 505                 510

Cys Ser Ile Ser Cys Gly Met Gly Met Arg Ser Arg Glu Arg Tyr Val
        515                 520                 525

Lys Gln Phe Pro Glu Asp Gly Ser Val Cys Thr Leu Pro Thr Glu Glu
    530                 535                 540

Met Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
                565                 570                 575

Gly Met Lys Lys Arg His Arg Met Ile Lys Met Asn Pro Ala Asp Gly
            580                 585                 590

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
        610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
    690                 695                 700

Pro Cys Pro Glu Thr Val Gln Arg Lys Lys Cys Arg Ile Arg Lys Cys
705                 710                 715                 720

Leu Arg Asn Pro Ser Ile Gln Lys Pro Arg Trp Arg Glu Ala Arg Glu
                725                 730                 735

Ser Arg Arg Ser Glu Gln Leu Lys Glu Ser Glu Gly Glu Gln Phe
            740                 745                 750

Pro Gly Cys Arg Met Arg Pro Trp Thr Ala Trp Ser Glu Cys Thr Lys
        755                 760                 765

Leu Cys Gly Gly Gly Ile Gln Glu Arg Tyr Met Thr Val Lys Lys Arg
    770                 775                 780

Phe Lys Ser Ser Gln Phe Thr Ser Cys Lys Asp Lys Lys Glu Ile Arg
```

| | |
|---|---|
| 785 790 795 800 | |
| Ala Cys Asn Val His Pro Cys<br>805 | |

```
<210> SEQ ID NO 37
<211> LENGTH: 2805
<212> TYPE: DNA
<213> ORGANISM: Homo sapien
<220> FEATURE:
<221> NAME/KEY: CDS
<222> LOCATION: (616)...(1587)

<400> SEQUENCE: 37
```

| | |
|---|---:|
| cgggtctgat agtccctacc tgtcaggact ggtgttagga tgagataatg tttgtgaact | 60 |
| gtaaacatat ataaacgtgt gctactgtga gaactgaaac aaagaagaga gggagtgaga | 120 |
| gaaatcaagg gagggctggg gctgggaaag aacgaaaagg gagtcgcgta tagaggagag | 180 |
| gcgacagtcg cgagccacac tttgcaatga aactctttag actttctgcc gggagagcgg | 240 |
| cccagacgcg ccaggtctgt agcaggaggc cgcgagggcg ggtccccaga agcctacagg | 300 |
| tgagtatcgg ttctcccctt ccggctttc ggtccgagg aggcgggagc agcttccctg | 360 |
| ttctgatcct atcgcgggcg gcgcagggcc ggcttggcct tccgtgggac ggggagggg | 420 |
| gcgggatgtg tcacccaaat accagtgggg acgtcggtg gtggaaccag ccgggcaggt | 480 |
| cgggtagagt ataagagccg gagggagcgg ccggggcgca gacgcctgca gaccatccca | 540 |
| gacgccggag cccgagcccc gacgagtccc cgcgcctcat ccgcccgcgt ccggtccgcg | 600 |
| ttcctccgcc ccacc atg gct cgg ggc ccc ggc ctc gcg ccg cca ccg ctg<br>                    Met Ala Arg Gly Pro Gly Leu Ala Pro Pro Leu<br>                     1           5                 10 | 651 |
| cgg ctg ccg ctg ctg ctg ctg gtg ctg gcg gcg gtg acc ggc cac acg<br>Arg Leu Pro Leu Leu Leu Leu Val Leu Ala Ala Val Thr Gly His Thr<br>       15                    20                   25 | 699 |
| gcc gcg cag gac aac tgc acg tgt ccc acc aac aag atg acc gtg tgc<br>Ala Ala Gln Asp Asn Cys Thr Cys Pro Thr Asn Lys Met Thr Val Cys<br>     30                    35                   40 | 747 |
| agc ccc gac ggc ccc ggc ggc cgc tgc cag tgc cgc gcg ctg ggc tcg<br>Ser Pro Asp Gly Pro Gly Gly Arg Cys Gln Cys Arg Ala Leu Gly Ser<br> 45                   50                   55                   60 | 795 |
| ggc atg gcg gtc gac tgc tcc acg ctg acc tcc aag tgt ctg ctg ctc<br>Gly Met Ala Val Asp Cys Ser Thr Leu Thr Ser Lys Cys Leu Leu Leu<br>               65                    70                   75 | 843 |
| aag gcg cgc atg agc gcc ccc aag aac gcc cgc acg ctg gtg cgg ccg<br>Lys Ala Arg Met Ser Ala Pro Lys Asn Ala Arg Thr Leu Val Arg Pro<br>            80                    85                   90 | 891 |
| agt gag cac gcg ctc gtg gac aac gat ggc ctc tac gac ccc gac tgc<br>Ser Glu His Ala Leu Val Asp Asn Asp Gly Leu Tyr Asp Pro Asp Cys<br>     95                    100                 105 | 939 |
| gac ccc gag ggc cgc ttc aag gcg cgc cag tgc aac cag acg tcg gtg<br>Asp Pro Glu Gly Arg Phe Lys Ala Arg Gln Cys Asn Gln Thr Ser Val<br>110                   115                  120 | 987 |
| tgc tgg tgc gtg aac tcg gtg ggc gtg cgc cgc acg gac aag ggc gac<br>Cys Trp Cys Val Asn Ser Val Gly Val Arg Arg Thr Asp Lys Gly Asp<br>125                   130                  135                  140 | 1035 |
| ctg agc cta cgc tgc gat gag ctg gtg cgc acc cac cac atc ctc att<br>Leu Ser Leu Arg Cys Asp Glu Leu Val Arg Thr His His Ile Leu Ile<br>                145                  150                155 | 1083 |
| gac ctg cgc cac cgc ccc acc gcc ggc gcc ttc aac cac tca gac ctg<br>Asp Leu Arg His Arg Pro Thr Ala Gly Ala Phe Asn His Ser Asp Leu<br>                    160                  165                170 | 1131 |

-continued

```
gac gcc gag ctg agg cgg ctc ttc cgc gag cgc tat cgg ctg cac ccc    1179
Asp Ala Glu Leu Arg Arg Leu Phe Arg Glu Arg Tyr Arg Leu His Pro
        175                 180                 185 aag ttc gtg gcg gcc gtg cac tac gag cag ccc acc atc cag atc gag    1227
Lys Phe Val Ala Ala Val His Tyr Glu Gln Pro Thr Ile Gln Ile Glu
    190                 195                 200 ctg cgg cag aac acg tct cag aag gcc gcc ggt gaa gtg gat atc ggc    1275
Leu Arg Gln Asn Thr Ser Gln Lys Ala Ala Gly Glu Val Asp Ile Gly
205                 210                 215                 220 gat gcc gcc tac tac ttc gag agg gac atc aag ggc gag tct cta ttc    1323
Asp Ala Ala Tyr Tyr Phe Glu Arg Asp Ile Lys Gly Glu Ser Leu Phe
                225                 230                 235 cag ggc cgc ggc ggc ctg gac ttg cgc gtg cgc gga gaa ccc ctg cag    1371
Gln Gly Arg Gly Gly Leu Asp Leu Arg Val Arg Gly Glu Pro Leu Gln
            240                 245                 250 gtg gag cgc acg ctc atc tat tac ctg gac gag att ccc ccg aag ttc    1419
Val Glu Arg Thr Leu Ile Tyr Tyr Leu Asp Glu Ile Pro Pro Lys Phe
        255                 260                 265 tcc atg aag cgc ctc acc gcc ggc ctc atc gcc gtc atc gtg gtg gtc    1467
Ser Met Lys Arg Leu Thr Ala Gly Leu Ile Ala Val Ile Val Val Val
    270                 275                 280 gtg gtg gcc ctc gtc gcc ggc atg gcc gtc ctg gtg atc acc aac cgg    1515
Val Val Ala Leu Val Ala Gly Met Ala Val Leu Val Ile Thr Asn Arg
285                 290                 295                 300 aga aag tcg ggg aag tac aag aag gtg gag atc aag gaa ctg ggg gag    1563
Arg Lys Ser Gly Lys Tyr Lys Lys Val Glu Ile Lys Glu Leu Gly Glu
                305                 310                 315 ttg aga aag gaa ccg agc ttg tag gtacccggcg gggcagggga tggggtgggg   1617
Leu Arg Lys Glu Pro Ser Leu  *
            320 taccggattt cggtatcgtc ccagacccaa gtgagtcacg cttcctgatt cctcggcgca   1677 aaggagacgt ttatccttc aaattcctgc cttcccctc ccttttgcgc acacaccagg    1737 tttaatagat cctggcctca gggtctcctt tctttctcac ttctgtcttg agggaagcat   1797 ttctaaaatg tatccccttt cggtccaaca acaggaaacc tgactgggc agtgaaggaa    1857 gggatggcac agcgttatgt gtaaaaaaca agtatctgta tgacaacccg ggatcgtttg   1917 caagtaacta atccattgc gacattgtga aggcttaaat gagtttagat gggaaatagc    1977 gttgttatcg ccttgggttt aaattatttg atgagttcca cttgtatcat ggcctacccg   2037 aggagaagag gagtttgtta actgggccta tgtagtagcc tcatttacca tcgtttgtat   2097 tactgaccac atatgcttgt cactgggaaa gaagcctgtt tcagctgcct gaacgcagtt   2157 tggatgtctt tgaggacaga cattgcccgg aaactcagtc tatttattct tcagcttgcc   2217 cttactgcca ctgatattgg taatgttctt ttttgtaaaa tgtttgtaca tatgttgtct   2277 ttgataatgt tgctgtaatt ttttaaaata aaacacgaat ttaataaaat atgggaaagg   2337 cacaaaccag aagtcggcat ttgtgaaaag tccctccaga tttctatcac tttggtctct   2397 aatttcccaa gacttgtatt ttttttttat ttcaaattat aacacttttt ttcccccag    2457 aagtgggtgt ttcatgttgc tactctggtg tgtcccaaga tatcctaact ggccagtgta   2517 aatgctattc tttctaaata agattatttg gaaacttcct tcaaactgca ggagggcgag   2577 ctctgagggc acgagaagct aaaactagct gcttttgatg aaaaagagtg ccagtctttg   2637 gtcatctcta aacaaggctt atcaccaatg gagacagaaa actctagttc aagagctgta   2697 cctcctttga atcccagccc tactcgaaat aagtggtact atttccattt agcctttgag   2757
```
caaatcactt aactcaaagg cgttgtggct ctaagattaa acgacttt            2805

<210> SEQ ID NO 38
<211> LENGTH: 323
<212> TYPE: PRT
<213> ORGANISM: Homo sapien

<400> SEQUENCE: 38

```
Met Ala Arg Gly Pro Gly Leu Ala Pro Pro Leu Arg Leu Pro Leu
 1               5                  10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Glu Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu
```

<210> SEQ ID NO 39
<211> LENGTH: 590
<212> TYPE: DNA
<213> ORGANISM: Homo sapien
<220> FEATURE:
<221> NAME/KEY: CDS

<222> LOCATION: (28)...(402)

<400> SEQUENCE: 39

```
acctgcaccc cgcccgggca tagcacc atg cct gct tgt cgc cta ggc ccg cta         54
                              Met Pro Ala Cys Arg Leu Gly Pro Leu
                                1               5 gcc gcc gcc ctc ctc ctc agc ctg ctg ctg ttc ggc ttc acc cta gtc         102
Ala Ala Ala Leu Leu Leu Ser Leu Leu Leu Phe Gly Phe Thr Leu Val
 10              15                  20                  25 tca ggc aca gga gca gag aag act ggc gtg tgc ccc gag ctc cag gct         150
Ser Gly Thr Gly Ala Glu Lys Thr Gly Val Cys Pro Glu Leu Gln Ala
             30                  35                  40 gac cag aac tgc acg caa gag tgc gtc tcg gac agc gaa tgc gcc gac         198
Asp Gln Asn Cys Thr Gln Glu Cys Val Ser Asp Ser Glu Cys Ala Asp
         45                  50                  55 aac ctc aag tgc tgc agc gcg ggc tgt gcc acc ttc tgc tct ctg ccc         246
Asn Leu Lys Cys Cys Ser Ala Gly Cys Ala Thr Phe Cys Ser Leu Pro
     60                  65                  70 aat gat aag gag ggt tcc tgc ccc cag gtg aac att aac ttt ccc cag         294
Asn Asp Lys Glu Gly Ser Cys Pro Gln Val Asn Ile Asn Phe Pro Gln
 75                  80                  85 ctc ggc ctc tgt cgg gac cag tgc cag gtg gac agc cag tgt cct ggc         342
Leu Gly Leu Cys Arg Asp Gln Cys Gln Val Asp Ser Gln Cys Pro Gly
 90                  95                 100                 105 cag atg aaa tgc tgc cgc aat ggc tgt ggg aag gtg tcc tgt gtc act         390
Gln Met Lys Cys Cys Arg Asn Gly Cys Gly Lys Val Ser Cys Val Thr
                 110                 115                 120 ccc aat ttc tga gctccagcca ccaccaggct gagcagtgag gagagaaagt            442
Pro Asn Phe * ttctgcctgg ccctgcatct ggttccagcc cacctgccct ccccttttc gggactctgt        502 attccctctt gggctgacca cagcttctcc ctttcccaac caataaagta accactttca       562
gcaaaaaaaa aaaaaaaaaa aaaaaaaa                                          590
```

<210> SEQ ID NO 40
<211> LENGTH: 124
<212> TYPE: PRT
<213> ORGANISM: Homo sapien

<400> SEQUENCE: 40

```
Met Pro Ala Cys Arg Leu Gly Pro Leu Ala Ala Ala Leu Leu Leu Ser
 1               5                  10                  15

Leu Leu Leu Phe Gly Phe Thr Leu Val Ser Gly Thr Gly Ala Glu Lys
                 20                  25                  30

Thr Gly Val Cys Pro Glu Leu Gln Ala Asp Gln Asn Cys Thr Gln Glu
             35                  40                  45

Cys Val Ser Asp Ser Glu Cys Ala Asp Asn Leu Lys Cys Cys Ser Ala
         50                  55                  60

Gly Cys Ala Thr Phe Cys Ser Leu Pro Asn Asp Lys Glu Gly Ser Cys
 65                  70                  75                  80

Pro Gln Val Asn Ile Asn Phe Pro Gln Leu Gly Leu Cys Arg Asp Gln
                 85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
            115                 120
```

<210> SEQ ID NO 41

<211> LENGTH: 450
<212> TYPE: DNA
<213> ORGANISM: Homo sapien
<220> FEATURE:
<221> NAME/KEY: CDS
<222> LOCATION: (67)...(288)

<400> SEQUENCE: 41

```
cccaagatgg actcaggcag gcagctctgc tgtatgtgaa gcccagtgag gggcagtggg      60 gggggcc atg ctg cag gta caa gtt aat ctc cct gta tcg cct ctg ccc       108
        Met Leu Gln Val Gln Val Asn Leu Pro Val Ser Pro Leu Pro
          1               5                  10 act tac cct tac tcc ttt ttc tac cca gat aag gag ggt tcc tgc ccc       156
Thr Tyr Pro Tyr Ser Phe Phe Tyr Pro Asp Lys Glu Gly Ser Cys Pro
 15              20                  25                  30 cag gtg aac att aac ttt ccc cag ctc ggc ctc tgt cgg gac cag tgc       204
Gln Val Asn Ile Asn Phe Pro Gln Leu Gly Leu Cys Arg Asp Gln Cys
                 35                  40                  45 cag gtg gac agc cag tgt cct ggc cag atg aaa tgc tgc cgc aat ggc       252
Gln Val Asp Ser Gln Cys Pro Gly Gln Met Lys Cys Cys Arg Asn Gly
             50                  55                  60 tgt ggg aag gtg tcc tgt gtc act ccc aat ttc tga ggtccagcca            298
Cys Gly Lys Val Ser Cys Val Thr Pro Asn Phe  *
         65                  70 ccaccaggct gagcagtgag gagagaaagt ttctgcctgg ccctgcatct ggttccagcc     358
cacctgccct cccctttttc gggactctgt attccctctt gggctgacca cagcttctcc     418
ctttcccaac caataaagta accactttca gc                                   450
```

<210> SEQ ID NO 42
<211> LENGTH: 73
<212> TYPE: PRT
<213> ORGANISM: Homo sapien

<400> SEQUENCE: 42

```
Met Leu Gln Val Gln Val Asn Leu Pro Val Ser Pro Leu Pro Thr Tyr
  1               5                  10                  15

Pro Tyr Ser Phe Phe Tyr Pro Asp Lys Glu Gly Ser Cys Pro Gln Val
             20                  25                  30

Asn Ile Asn Phe Pro Gln Leu Gly Leu Cys Arg Asp Gln Cys Gln Val
         35                  40                  45

Asp Ser Gln Cys Pro Gly Gln Met Lys Cys Cys Arg Asn Gly Cys Gly
     50                  55                  60

Lys Val Ser Cys Val Thr Pro Asn Phe
 65                  70
```

<210> SEQ ID NO 43
<211> LENGTH: 705
<212> TYPE: DNA
<213> ORGANISM: Homo sapien
<220> FEATURE:
<221> NAME/KEY: CDS
<222> LOCATION: (339)...(626)

<400> SEQUENCE: 43

```
ctgccgcccg cccagacgcc agcaagcccc cctcccacga cagggctgct ccgggagctt     60
cggagacccg cccccgggcct gagcgcaggc tgcctccggg accccacggc tgtccggacg    120
tgccatgggc gcgcagctgc cgggcaacgt gttgtgtaag tgaacatctg ggaggtaaac    180
actacacgtg aagagtggtg aaagggaaca ttgattactg aagtgccctg gagagggaaa   240
```

```
                                                              -continued
gcactggtca acatcacatg gacaaatttc attgttttct aaagatggcc tggaagtagt    300
ctttgccact gcttcctcca caaacagctc ttcataac atg ggc tgc atg aaa tca   356
                                          Met Gly Cys Met Lys Ser
                                          1               5 aag caa act ttc cca ttt cct acc ata tat gaa ggt gag aag cag cat     404
Lys Gln Thr Phe Pro Phe Pro Thr Ile Tyr Glu Gly Glu Lys Gln His
         10                  15                  20 gag agt gaa gaa ccc ttt atg cca gaa gag aga tgt cta cct agg atg     452
Glu Ser Glu Glu Pro Phe Met Pro Glu Glu Arg Cys Leu Pro Arg Met
             25                  30                  35 gct tct cca gtt aat gtc aaa gag gaa gtg aag gaa cct cca ggg acc     500
Ala Ser Pro Val Asn Val Lys Glu Glu Val Lys Glu Pro Pro Gly Thr
     40                  45                  50 aat att gtg atc ttg gaa tat gca cac cgc ctg tct cag gat atc ttg     548
Asn Ile Val Ile Leu Glu Tyr Ala His Arg Leu Ser Gln Asp Ile Leu
 55                  60                  65                  70 tgt gat gcc ttg cag caa tgg gca tgc aat aac atc aag tac cat gac     596
Cys Asp Ala Leu Gln Gln Trp Ala Cys Asn Asn Ile Lys Tyr His Asp
                 75                  80                  85 att cca tac att gag agt gag ggg cct tga ggctgtagga tgacaacact       646
Ile Pro Tyr Ile Glu Ser Glu Gly Pro *
                 90                  95 ttgactgtgg aggtgctagt ttgaataaat gtgacaaaag caaaaaaaaa aaaaaaaaa    705

<210> SEQ ID NO 44
<211> LENGTH: 95
<212> TYPE: PRT
<213> ORGANISM: Homo sapien

<400> SEQUENCE: 44

Met Gly Cys Met Lys Ser Lys Gln Thr Phe Pro Phe Pro Thr Ile Tyr
1               5                   10                  15

Glu Gly Glu Lys Gln His Glu Ser Glu Glu Pro Phe Met Pro Glu Glu
            20                  25                  30

Arg Cys Leu Pro Arg Met Ala Ser Pro Val Asn Val Lys Glu Glu Val
        35                  40                  45

Lys Glu Pro Pro Gly Thr Asn Ile Val Ile Leu Glu Tyr Ala His Arg
    50                  55                  60

Leu Ser Gln Asp Ile Leu Cys Asp Ala Leu Gln Gln Trp Ala Cys Asn
65                  70                  75                  80

Asn Ile Lys Tyr His Asp Ile Pro Tyr Ile Glu Ser Glu Gly Pro
                85                  90                  95
```